United States Patent
Houchen et al.

(10) Patent No.: US 8,198,255 B2
(45) Date of Patent: Jun. 12, 2012

(54) SIRNA-MEDIATED INHIBITION OF DOUBLECORTIN AND CA2+/CALMODULIN-DEPENDENT KINASE-LIKE-1

(75) Inventors: Courtney Houchen, Edmond, OK (US); Randal May, Oklahoma City, OK (US); Shrikant Anant, Edmond, OK (US); Sripathi M. Sureban, Oklahoma City, OK (US)

(73) Assignee: The Board of Regents of the University of Oklahoma, Norman, OK (US)

( * ) Notice: Subject to any disclaimer, the term of this patent is extended or adjusted under 35 U.S.C. 154(b) by 221 days.

(21) Appl. No.: 12/454,355

(22) Filed: May 15, 2009

(65) Prior Publication Data

US 2009/0285883 A1    Nov. 19, 2009

Related U.S. Application Data

(60) Provisional application No. 61/128,063, filed on May 16, 2008.

(51) Int. Cl.
*A61K 31/70* (2006.01)
*C07H 21/04* (2006.01)
*C12Q 1/70* (2006.01)
*C12N 5/00* (2006.01)
*C07H 21/02* (2006.01)

(52) U.S. Cl. ........ 514/44 A; 435/6.1; 435/325; 435/375; 536/23.1; 536/24.5

(58) Field of Classification Search ........................ None
See application file for complete search history.

(56) References Cited

U.S. PATENT DOCUMENTS

| 7,345,027 | B2 | 3/2008 | Tolentino et al. |
| 7,511,025 | B2 | 3/2009 | Wyatt et al. |
| 7,511,132 | B2 | 3/2009 | Khvorova et al. |
| 2005/0255487 | A1 * | 11/2005 | Khvorova et al. ............ 435/6 |

FOREIGN PATENT DOCUMENTS

WO    WO 2007/086738    *    8/2007

OTHER PUBLICATIONS

May, et al., "DCAMKL-1 and LGR5 Mark Quiescent and Cycling Intestinal Stem Cells Respectively", Stem Cell, pp. 1-38 (2009).
Sureban et al., "Knockdown of RNA Binding Portein Musashi-1 Leads to Tumor Regression in Vivo", Gastroenterology 134:1448-1458, (2008).

* cited by examiner

*Primary Examiner* — Doug Schultz
(74) *Attorney, Agent, or Firm* — Dunlap Codding, P.C.

(57) ABSTRACT

DCAMKL-1 has been identified as a biomarker for stem cells, as well as cancer stem cells. Methods of detecting the presence of at least one stem cell, methods of isolating stem cells, and methods of inhibiting growth of cancer cells utilizing DCAMKL-1 are disclosed herein.

12 Claims, 29 Drawing Sheets
(26 of 29 Drawing Sheet(s) Filed in Color)

Figure 26
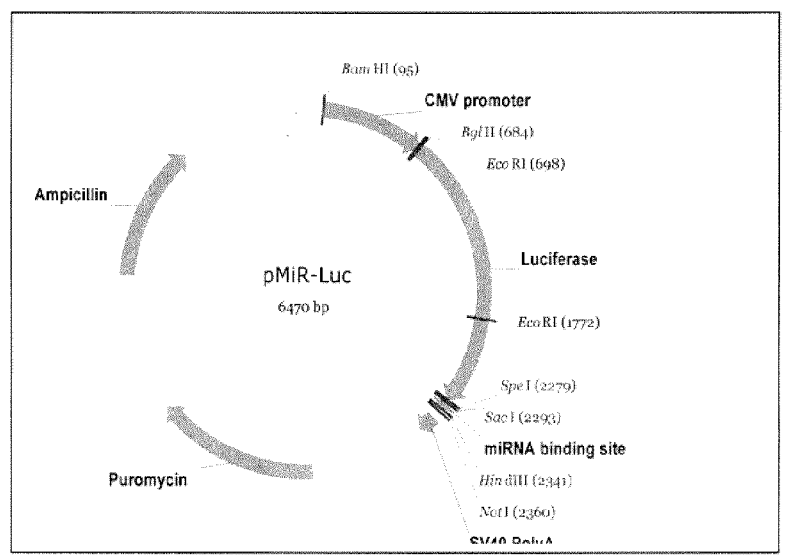
SEQ ID
NO:
16  5' ---AGAAAAATCAGAGAGATCCTCATAA--AGGCCAAGAAGGGCGGAAAGTCCAAATTGCTCGAG
           Luciferase Gene
17  TGATGAAAGCTGCGCACTAGT-- AACTATACAACCTACTACCTCA--AAGCTTAATAAAGGAT
           (SpeI)    let7a Binding Site    (HindIII)
18  CTTTTATTTT CATTGGATCT GTGTGTTGGT TTTTTGTATG CGGCCGCTA--- 3'
                                                  (NotI)
Signosis

Figure 28
A
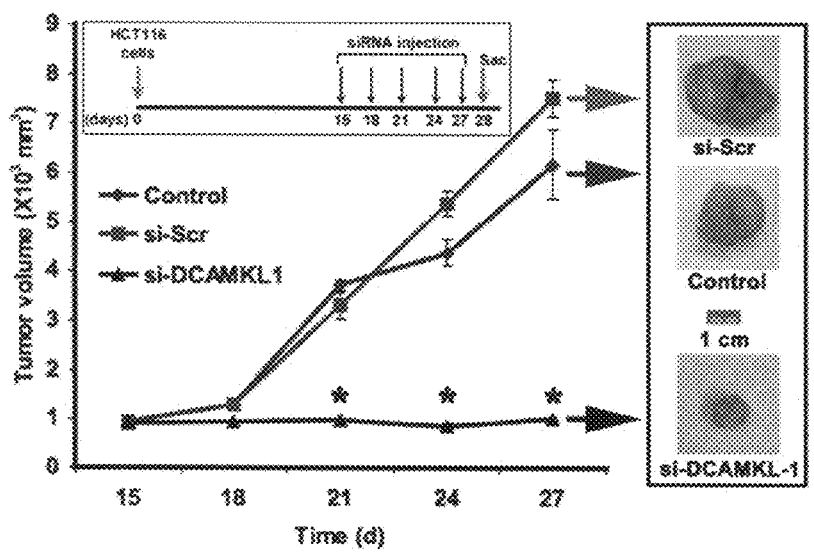
B
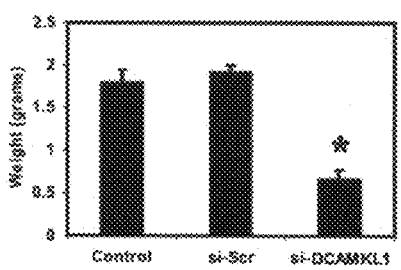
C
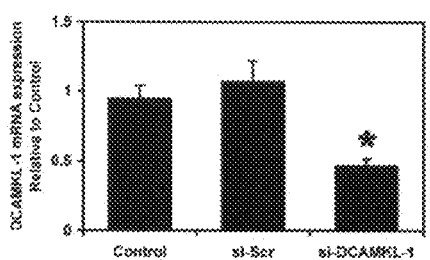
D
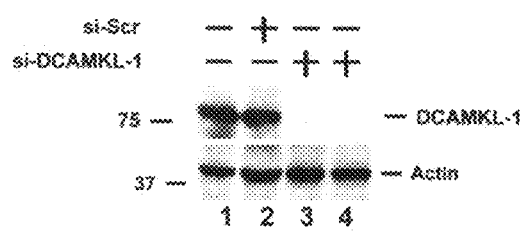

Figure 29
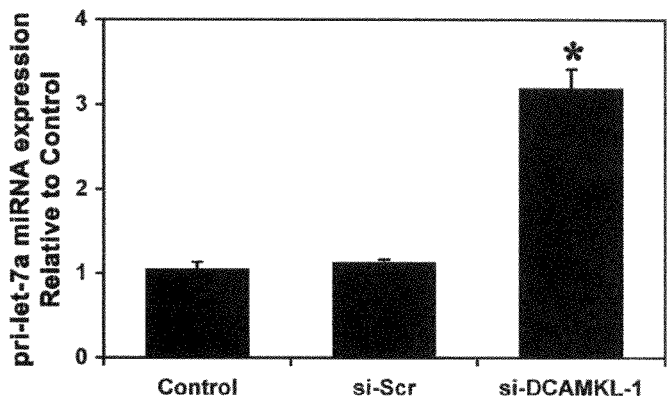
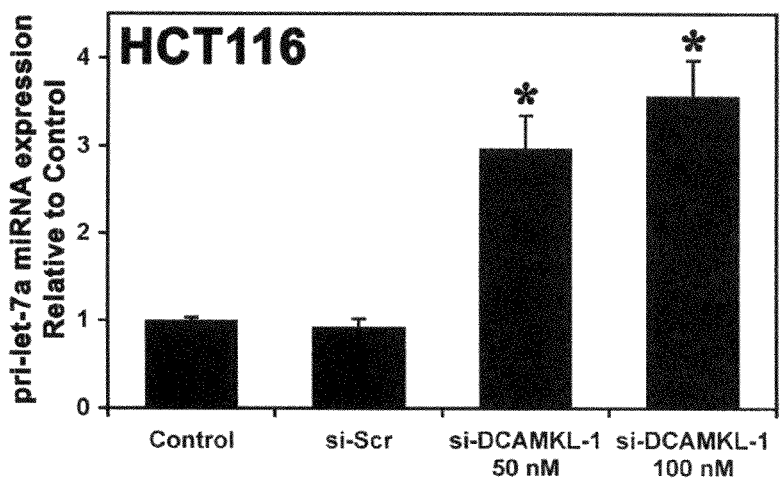
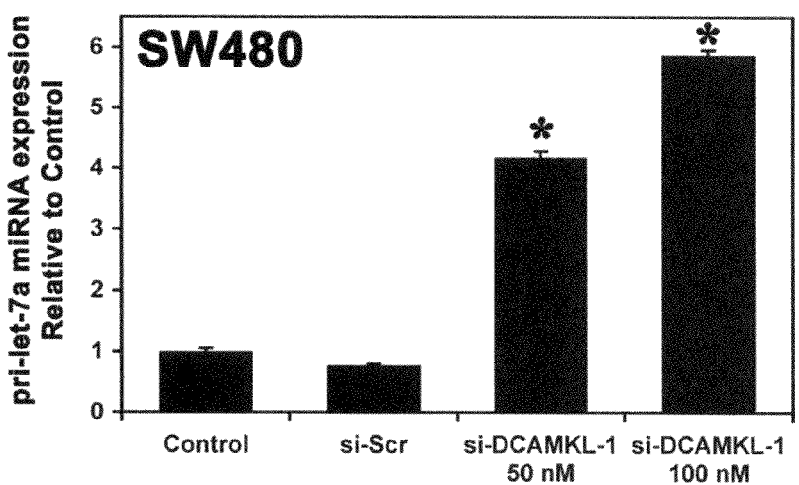

Figure 31
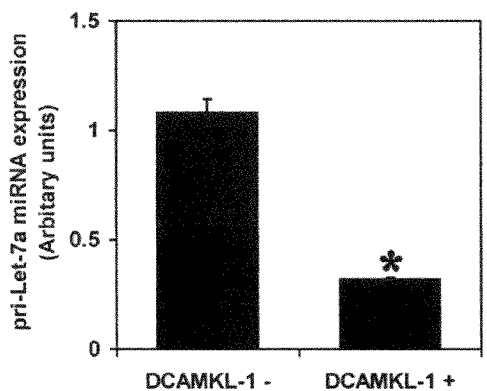
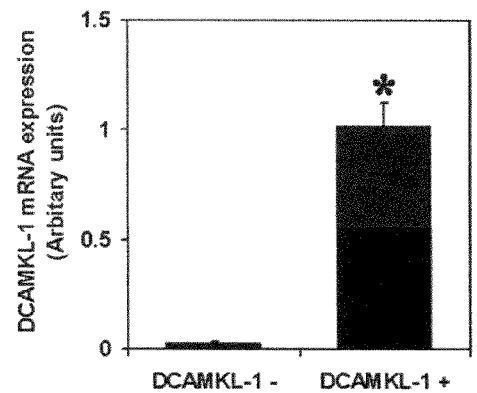
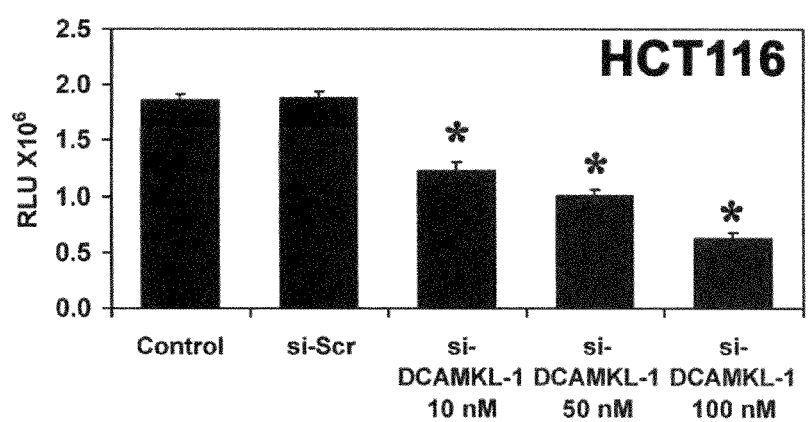
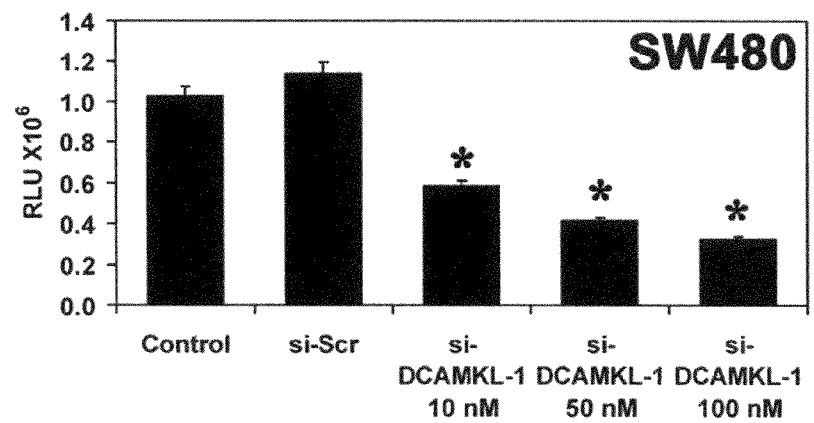

SEQUENCE LISTING

<160> NUMBER OF SEQ ID NOS: 18

<210> SEQ ID NO 1
<211> LENGTH: 8082
<212> TYPE: RNA
<213> ORGANISM: Homo sapiens

<400> SEQUENCE: 1

```
uuucaaugag gacgggccga ggcacauccc ugcacuagug gccgcaaccg aggcgccgcg      60
cuccagcagc ugcugccgcc cagcccggcc ccgccgccgc ccccagccc ugcagccccg      120 cagccccggc cgcgcccagc ccggcgagga cagcaccagg aggcggcccc cagcgcggcc     180
acaaagaccc ccggcggcgu cucuccgcgg accguccua cuugaaguuc aucauguccu     240
ucggcagaga cauggagcug gagcacuucg acgagcggga uaaggcgcag agauacagcc     300
gagggucgcg ggugaacggc cugccgagcc cgacgcacag cgcccacugc agcuucuacc     360
gcacccgcac gcugcagacg cucagcuccg agaagaaggc caagaaaguu cguuucuauc     420
gaaacggaga ucgauacuuc aaagggauug uguaugccau cuccccagac cgguuccgau     480
cuuuugaggc ccugcuggcu gauuugaccc gaacucuguc ggauaacgug aauuugcccc     540
agggagugag aacaaucuac accauugaug ggcucaagaa gauuccagc cuggaccaac     600 ugguggaagg agagaguuau guaugugcu ccauagagcc cuucaagaaa cuggaguaca     660
ccaagaaugu gaaccccaac ggucggguga acgucaagac caccucggcu ucucgggcag     720
ugucuucacu ggccacugcc aaaggaagcc cuucagaggu gcgagagaau aaggauuuca     780
uucggcccaa gcuggucacc aucaucgaaa guggcgugaa gccacggaaa gcugucagga     840
uucugcugaa caagaaaacg gcucauuccu uugagcaggu ccucaccgau aucaccgaug     900
ccaucaagcu ggacucggga guggugaaac gccuguacac guuggaugg aaacagguga     960 uguccuuca ggacuuuuuu ggugaugaug acauuuuuau ugcaugugga ccggagaagu    1020
uccguuacca ggaugauuuc uugcuagaug aaagugaaug ucgaguggua aaguccacuu    1080
cuuacaccaa aauagcuuca ucaucccgca ggagcaccac caagagccca ggaccguccea   1140 ggcguagcaa gucccctgcc uccaccagcu caguuaaugg aacccccuggu agucagcucu    1200 cuacuccgcg cucaggcaag ucgccaagcc caucacccac cagcccagga agccugcgga    1260
agcagaggag cucucagcau ggcggcuccu cuacgucacu ugcguccacc aaagucuga    1320
```

```
gcucgaugga ugagaacgau ggcccuggag aagaaguguc ggaggaaggc uuccagauuc   1380
cagcuacaau aacagaacga uauaaagucg gaagaacaau aggagaugga auuuugcug    1440 uugucaagga auguguagaa agaucgacug cuagagagua ugcucugaaa auuaucaaga   1500
aaagcaaaug ucgaggcaaa gagcacauga uccagaauga agucuauu uuaagaagag    1560 ugaagcaucc caauaucguu cuucugauug aggaugauga ugugccaacu gaacuguauc   1620
uugucaugga auuaguaaag gggggagacc uuuuugaugc cauuacuucc acuaacaaau   1680
acaccgagag agacgccagu gggaugcugu acaaccuagc cagcgccauc aaauaccugc   1740
auagccugaa caucguccac cgugauauca agccagagaa ccugcggug uaugagcacc    1800 aagauggcag caaaucacug aagcugggug acuuuggacu ggccaccauu guagacggcc   1860
cccuguacac agucugugc accccaacau acgggcucc agaaaucauu gcagagacug     1920
gauacggccu caagguggac aucugggcag cagguguaau cacuuauauc cugcugugug   1980
guuuccuucc auccgugga agugugaug accaggaggu gcuuuugau cagauuuuga      2040 ugggggcaggu ggacuuuccu ucuccauacu gggauaaugu uccgauucu gcaaaggagc   2100 ucauuaccau gaugcuguug gucgaugag aucagcgauu uucugcuguu caaguacuug    2160
agcaucccug gguuaaugau gauggccucc cagaaaauga acaucagcug ucaguagcug   2220
gaaagauaaa gaagcauuuc aacacaggcc ccaagccgaa uagcacagca gcuggaguuu   2280
cugucauagc acuggaccac ggguuuacca ucaagagauc agggucuuug gacuacuacc   2340
agcaaccagg aauguauugg auaagaccac cgcucuugau aaggagaggc agguuuuccg   2400
acgaagacgc aaccaggaug ugaggagccg guacaaggcg cagccagcuc uccccgaacu   2460
caacucggaa ucggaagacu acuccccaag cuccuccgag acuguucgcu ccccuaacuc   2520
gcccuuuuaa uaagacccuu uuacucaaag uccuagcuua acccuuugag acucugauau   2580 uuuuucccc caaauuugug uaaaacaguu caucugauc uaucuagcgc ucaaugcuug     2640
aauggcagaa cugaaagugu uucagguau cuuuguagcg guucccuuu acugaauaag     2700 augacacgug gugauguga agauggcuau uugcugcuaa uagagccuc aaagggguuaa    2760 ggccaauuug caauuuuuuu uuaaacuuag aagcaaugaa uguuucauc agucaagcua    2820 ggaucugcag uaguaauau agcacuuguu aacccucuga gugcauagaa uuuauugag     2880 aauucuuguu uggaauuuu ucaggccuu ggauguauac acacauguuu cuugauuuua     2940
cugcagauca aggggguguug uuagaugcug aaauguccag aaaagaagga cauuuagaau  3000
gauaucuugu uuguccuuu cugugggguu agaacggggc agguuuauaa cuucgacaca    3060
cgcacgguuc uuucuucuuc acaauccuau ucagaaacag auuuuuuu ucauuagaga     3120 uaugacuguc aguugcagug aguucugcau cccaagugga gggaauuggg uuuguggcaa  3180
agagcuugac ccaggaauaa gauggugccc cccaaauugu cuccacauga agauguacug   3240
augacgcccc agaaaugcug cuuccauauc agcugcugcu agcgccagcg cagacucuca   3300
gggagucacc acagcuuguc uugugcuugg ugagugaggg ucucucuacu caguguagaca 3360 caucuacagg aaagaaacaa cugguggaaa agagcaauaa auugcccggu gcucugcagg  3420
gcuggaauuu caaacagaaa gagggaauaa gauccuguga uuuucucac cugcuuuucc   3480 acgcacugug gucaucacug ugcaaucuac aucuaguaug aaauccacac auaggagagc  3540
uggggcacaa ggggacugga ggcaguugcu uugcaagaug gcugaggaga aagcacacug   3600
ggaacacaau ccagauguuu cuaacaauaa guuucagug aauaaaccac uggcaagaca    3660
auuccaugug caccuuuagg uuaccuauau agucuccuag gaagaucagg augaaagacc   3720
```

```
uagaugauac cccugaggau aaaaccucca uccccuaaaa ugauuuuuu uaaauaccac    3780 ugucuuuagc uguccaggag gucagagugu uuuuucuguc uuugggccaa guccugucug   3840
agaccuguau uuucacucuu guuaccaaau cuaucaaccu agugcagugu cuccaggccu   3900
gaguuucuuc uggaacagau uccauuuuag aaugggggauu cacagguucu gugcaucacc  3960
acagugcuca gagaggauuc uccuggggug ucuuagaggc aggugcccaa cucaaaugua   4020
uucccaaggu uugcugggcu cugggauacca cgagacaacc agagagggau aucucaugaa  4080
auuugcaucu gguggcugaa caguaccuau guucucuguu uugaauauac uuuaauaccu   4140
gagagucuua aaauuuguga acaacguuuc auaguccuu uauuucaaaa ugcacauuga    4200
ucuucacuug cugcauuuuu acucuucaac ccugaaacua ggucuacau uaauauggau    4260 uuuuaaauca caugucauua cuuuugcaac accaucacca aaauuuuuug ucuuuuuaca   4320
uuuagguuca ucucuguggu cuguguuguc cugacaugua aaaagcauau cguuuauuga   4380
gguuuuuuuc cccccuuuu agagcauccg gaagugauaa cacgcaaaaau cacaaaguag   4440 cauaaaucag uaaauuaguu gaguuguuuu uggggggggag ugggggguag ggggcacaga  4500
acaccagaaa gaguguuggu guguaggag auuccauauu aaugaggaac acugaacuag    4560
uuggaaauua cugcuuucuc uagaaauaua aagcaaagca cuauuccaag gcuauggagu   4620
agcucuacag ccuggccuca acucuaaaag ugugaagaau gcaauggggca gagaccuacc  4680 ugcaguggac ugucauuuuc cuucucuu cugaauuacu gcuuuuucug ugggcauuaa    4740
cuauauugcu acagcaucua guguacgag ccugcggugc auggcucagg ccuuucccca    4800
ucgacgucua gggggacucu ggaccgugug aagcuagggg guguuucuca gcacaacugca  4860 gaagggcagc ucagaagaau gcaggggccca uucagcaugg ggaucccagc acaucacugu  4920
agaauuugag ugaucuaugc ugaauaaaca guggaaugug accagucaag uagaaaucuu   4980
gaguaaucag auggaaugca aucuuucaa cauuaagcua ccaagauccu gaaugcaga    5040 gauguacuca gaggguuaac agacaagcac aaggcaugcu gacuacauug guguauccag  5100
auugcuuugc uuuuagccag ugcuuucaa uuuuuucucu gacauucuug ggauaguuca    5160
aguuugaaau aauuaagugg uggguucuu uaaggaauuu cuauaaccaa auugaucuua   5220
uuuuugauuu cacuuaucau agaacaaaua uguacauua uggcagugua ucuauguaau   5280
uaucaauuua aucaucacca ccgguugguuuc cauauuuuuu cccaaguauu uaauauagcu  5340
cucuuauggu ggugccuggg ugauggggac cgucuuuuu uuacugacac augaccaauc   5400
auaugguauu uucaaggggaa uuuuaagauu caucuuuca guuugauagu agacuaguua   5460
aggaagaacu cuuucauuac uugcaucgug uaaaucaucu cuguagacau guguucauau   5520
uauugaacac auuuuuuucu aacauuguag cagaaaucau uuuauucguc augaucaaug   5580
aauaugugau uugcuccaga ucguuagaag gaaaaguaag auuucaguca ucaaaaaugu   5640
uuuuaccgua gcccucaucu aacuuacacg uggugcauau uaaaauaagc agagaaaaaa    5700
aaaugugaau aaacuacuga aaacacuugg guuuguguu ucaugagac cuuccugcaa    5760 ccugcucccc auggugggcca guuaacaggc ccaucagaua uuguugaaag aaagcaauau  5820
auccaugaau gaaggcuaaa auugcaaucc uuuacccuuu gaggcauauu ucaguugaaa    5880
acaaaaagaa aagaaaauuu gggcuuagagg gucacagagc ucccauauga ccaagucuca  5940
agcacauuaa aucaugguug uuuacuggcc aagggcgucc acuagacaac ucuauccuu    6000 gcgcugaagc ucaacgugc ugagggggagag cuuucuaauu auuacuguguuu ugcucuuagc 6060 ccuucucugg guuaggaucu gucagcauuu cuaugauaaaa cuccuauucu caaagguuuuu  6120
```

```
uaauuugacc auaaaaaugu gccccaggcu gaaguuugcu auacagggcu guaccaaaga    6180
gugaagguuu acuuccuucu cuuuccaacu ucuucccau ucuccaagga aaagaacaac     6240
aaaaaaaucu gguauggucc cuccuuaaua gugauuucag aauuuggaa agcaccaaga     6300 uccaagaugg uaguuuuaau guaguuacuc auucgcacac auuuuuaaa uuuaaugggu     6360 caccuggcau auauuguaga uaacauaucu uuucuauaau uguaaguca auaauuuuuu     6420 uaacugcuac augauauuuu uuuuugccca aagauuuuaa aagacuugaa guggucagu     6480 ucaaaacuca gauuuuucua cacauugucu gccaugucca uuaggaguuu ggggaaaaua    6540
cucucacaca gacccuuacu uugcaugcag uuuagagggu aagauacgug cuucuuuugg    6600
ggauaaagau uccuuacuu aauugucaaa uucauggag ccauucuagu cuguuuggga      6660
aaauagugua uaaaagcacu uccaaaauua acauuuuuug acaauucaga augaaaaga     6720 agcaggggaa aauaauacac uuuacucuuu ucuugcuuaa aggcaaacaa aucaaugaaa    6780
cuugaggaca cacuaaacau uugauaacug caaaugugcu uuaaaaauug guucaauggu    6840
gcuuacacau gaaacgguaa caaaugggu uccuaggacg ucagaaggaa ucuuuaguuu     6900
guauguaauu acacacuaga ggaggaggug cuuuuaagcc agucuuuau uuuuaaucau     6960 cucaaauaug caaccauaca ugcaguaaca uuaagggucg uaaacuggug gaaacagga     7020 acuucagugg agaggcuuaa augccucugg uuagaguggg gguuuugu uguuuguuua      7080 uuguggguu ucaacacuga gcaucauuuc ugugaucaag uuucuaacug gcaugugauu     7140
ugaucaugag guuaccaua ucuugcccau acagacaaau gagagaucua guuucauuuu     7200
guucccuaaa gaaagaacac ucucuaaaau uaaaucauac cuguaaauuu cuucagcauu    7260
uguuucuguu caaugaaauu gagacccuua auguugcuuu aauguaaaau ugaauauuuu    7320
gucugugaua uacuuuaaua auuuaaagua aguaauaguu cuaaagucuu cacuguugcu    7380
acuaagagaa aauagaauuu uaaaggugau gauaaagaug cuauaaugc aguucacucc     7440 aguccaauca aauguaguaa gaaaaagucc uugaauaguu cucuagggac aauuucucac    7500
uugccauuga cauuaaucuu uggguauauc ucagaaaaaa uaaaaagaaa uugaaacugg    7560
uccaagguua uagucauauc cucgauaacu uugaaaaaa aauuuauua ggaauuaau       7620 acuagccuuu uucauucugg cugaaagaaa auuauuaaag gauuaguuga gugugaaauu    7680
caacaguauu uugcucauac auacuaaaaa ggugcguagg gacuuggcgc auuuaaacaa    7740
guuucugaaa gguuucaauu ugacucaaga aaaaaauuca auauuucuuu ugaaaauacu    7800
gaauuuauca cuugcugcau ggaucagaug gcauagguua aucuuugauu uucagaaucc    7860
uaaugaaaua acuuucaaac aauuugaguc cuuaauuaaa ggaggauga gauccaauuu     7920 uuccccuaa uccuucaguu uaagcugaua caugagguu aaugaggaau gaaaaucaucu     7980 gugauauauu augaucauuu aucaacugag cuuuuugau guugccuguu uuuauguaaa    8040
acauguucuu aaaguuaaua aaauaauagu acuuggugua aa                     8082
```

<210> SEQ ID NO 2
<211> LENGTH: 729
<212> TYPE: PRT
<213> ORGANISM: Homo sapiens

<400> SEQUENCE: 2

Met Ser Phe Gly Arg Asp Met Glu Leu Glu His Phe Asp Glu Arg Asp
1               5                   10                  15

Lys Ala Gln Arg Tyr Ser Arg Gly Ser Arg Val Asn Gly Leu Pro Ser
            20                  25                  30

```
Pro Thr His Ser Ala His Cys Ser Phe Tyr Arg Thr Arg Thr Leu Gln
         35                  40                  45

Thr Leu Ser Ser Glu Lys Lys Ala Lys Lys Val Arg Phe Tyr Arg Asn
     50                  55                  60

Gly Asp Arg Tyr Phe Lys Gly Ile Val Tyr Ala Ile Ser Pro Asp Arg
 65                  70                  75                  80

Phe Arg Ser Phe Glu Ala Leu Leu Ala Asp Leu Thr Arg Thr Leu Ser
                 85                  90                  95

Asp Asn Val Asn Leu Pro Gln Gly Val Arg Thr Ile Tyr Thr Ile Asp
             100                 105                 110

Gly Leu Lys Lys Ile Ser Ser Leu Asp Gln Leu Val Glu Gly Glu Ser
             115                 120                 125

Tyr Val Cys Gly Ser Ile Glu Pro Phe Lys Lys Leu Glu Tyr Thr Lys
             130                 135                 140

Asn Val Asn Pro Asn Trp Ser Val Asn Val Lys Thr Thr Ser Ala Ser
145                 150                 155                 160

Arg Ala Val Ser Ser Leu Ala Thr Ala Lys Gly Ser Pro Ser Glu Val
                 165                 170                 175

Arg Glu Asn Lys Asp Phe Ile Arg Pro Lys Leu Val Thr Ile Ile Arg
             180                 185                 190

Ser Gly Val Lys Pro Arg Lys Ala Val Arg Ile Leu Leu Asn Lys Lys
             195                 200                 205

Thr Ala His Ser Phe Glu Gln Val Leu Thr Asp Ile Thr Asp Ala Ile
             210                 215                 220

Lys Leu Asp Ser Gly Val Val Lys Arg Leu Tyr Thr Leu Asp Gly Lys
225                 230                 235                 240

Gln Val Met Cys Leu Gln Asp Phe Phe Gly Asp Asp Ile Phe Ile
                 245                 250                 255

Ala Cys Gly Pro Glu Lys Phe Arg Tyr Gln Asp Asp Phe Leu Leu Asp
                 260                 265                 270

Glu Ser Glu Cys Arg Val Val Lys Ser Thr Ser Tyr Thr Lys Ile Ala
             275                 280                 285

Ser Ser Ser Arg Arg Ser Thr Thr Lys Ser Pro Gly Pro Ser Arg Arg
             290                 295                 300

Ser Lys Ser Pro Ala Ser Thr Ser Ser Val Asn Gly Thr Pro Gly Ser
305                 310                 315                 320

Gln Leu Ser Thr Pro Arg Ser Gly Lys Ser Pro Ser Pro Ser Pro Thr
                 325                 330                 335

Ser Pro Gly Ser Leu Arg Lys Gln Arg Ser Ser Gln His Gly Gly Ser
                 340                 345                 350

Ser Thr Ser Leu Ala Ser Thr Lys Val Cys Ser Ser Met Asp Glu Asn
                 355                 360                 365

Asp Gly Pro Gly Glu Glu Val Ser Glu Glu Gly Phe Gln Ile Pro Ala
         370                 375                 380

Thr Ile Thr Glu Arg Tyr Lys Val Gly Arg Thr Ile Gly Asp Gly Asn
385                 390                 395                 400

Phe Ala Val Val Lys Glu Cys Val Glu Arg Ser Thr Ala Arg Glu Tyr
                 405                 410                 415

Ala Leu Lys Ile Ile Lys Lys Ser Lys Cys Arg Gly Lys Glu His Met
             420                 425                 430

Ile Gln Asn Glu Val Ser Ile Leu Arg Arg Val Lys His Pro Asn Ile
         435                 440                 445

Val Leu Leu Ile Glu Glu Met Asp Val Pro Thr Glu Leu Tyr Leu Val
450                 455                 460
```

Met Glu Leu Val Lys Gly Gly Asp Leu Phe Asp Ala Ile Thr Ser Thr
465                 470                 475                 480

Asn Lys Tyr Thr Glu Arg Asp Ala Ser Gly Met Leu Tyr Asn Leu Ala
            485                 490                 495

Ser Ala Ile Lys Tyr Leu His Ser Leu Asn Ile Val His Arg Asp Ile
                500                 505                 510

Lys Pro Glu Asn Leu Leu Val Tyr Glu His Gln Asp Gly Ser Lys Ser
            515                 520                 525

Leu Lys Leu Gly Asp Phe Gly Leu Ala Thr Ile Val Asp Gly Pro Leu
        530                 535                 540

Tyr Thr Val Cys Gly Thr Pro Thr Tyr Val Ala Pro Glu Ile Ile Ala
545                 550                 555                 560

Glu Thr Gly Tyr Gly Leu Lys Val Asp Ile Trp Ala Ala Gly Val Ile
                565                 570                 575

Thr Tyr Ile Leu Leu Cys Gly Phe Pro Pro Phe Arg Gly Ser Gly Asp
            580                 585                 590

Asp Gln Glu Val Leu Phe Asp Gln Ile Leu Met Gly Gln Val Asp Phe
        595                 600                 605

Pro Ser Pro Tyr Trp Asp Asn Val Ser Asp Ser Ala Lys Glu Leu Ile
610                 615                 620

Thr Met Met Leu Leu Val Asp Val Asp Gln Arg Phe Ser Ala Val Gln
625                 630                 635                 640

Val Leu Glu His Pro Trp Val Asn Asp Asp Gly Leu Pro Glu Asn Glu
                645                 650                 655

His Gln Leu Ser Val Ala Gly Lys Ile Lys Lys His Phe Asn Thr Gly
            660                 665                 670

Pro Lys Pro Asn Ser Thr Ala Ala Gly Val Ser Val Ile Ala Leu Asp
        675                 680                 685

His Gly Phe Thr Ile Lys Arg Ser Gly Ser Leu Asp Tyr Tyr Gln Gln
690                 695                 700

Pro Gly Met Tyr Trp Ile Arg Pro Pro Leu Leu Ile Arg Arg Gly Arg
705                 710                 715                 720

Phe Ser Asp Glu Asp Ala Thr Arg Met
                725

<210> SEQ ID NO 3
<211> LENGTH: 19
<212> TYPE: RNA
<213> ORGANISM: Homo sapiens

<400> SEQUENCE: 3
gggagugaga acaaucuac                                                  19

<210> SEQ ID NO 4
<211> LENGTH: 21
<212> TYPE: DNA
<213> ORGANISM: Homo sapiens

<400> SEQUENCE: 4
ggtgatccac atctgctgga a                                               21

<210> SEQ ID NO 5
<211> LENGTH: 20
<212> TYPE: DNA
<213> ORGANISM: Homo sapiens

<400> SEQUENCE: 5

```
atcattgctc ctcctcaggg                                           20

<210> SEQ ID NO 6
<211> LENGTH: 22
<212> TYPE: DNA
<213> ORGANISM: Homo sapiens

<400> SEQUENCE: 6
agtcttccga ttccgagttg ag                                        22

<210> SEQ ID NO 7
<211> LENGTH: 22
<212> TYPE: DNA
<213> ORGANISM: Homo sapiens

<400> SEQUENCE: 7
cagcaaccag gaatgtattg ga                                        22

<210> SEQ ID NO 8
<211> LENGTH: 22
<212> TYPE: DNA
<213> ORGANISM: Homo sapiens

<400> SEQUENCE: 8
cacacatcag cacaactacg ca                                        22

<210> SEQ ID NO 9
<211> LENGTH: 19
<212> TYPE: DNA
<213> ORGANISM: Homo sapiens

<400> SEQUENCE: 9
ttgaccctct tggcagcag                                            19

<210> SEQ ID NO 10
<211> LENGTH: 20
<212> TYPE: DNA
<213> ORGANISM: Homo sapiens

<400> SEQUENCE: 10
cagcctggac gagctggtgg                                           20

<210> SEQ ID NO 11
<211> LENGTH: 20
<212> TYPE: DNA
<213> ORGANISM: Homo sapiens

<400> SEQUENCE: 11
tgaccagttg gggttcacat                                           20

<210> SEQ ID NO 12
<211> LENGTH: 17
<212> TYPE: DNA
<213> ORGANISM: Homo sapiens

<400> SEQUENCE: 12
ctcgcttcgg cagcaca                                              17

<210> SEQ ID NO 13
<211> LENGTH: 20
<212> TYPE: DNA
<213> ORGANISM: Homo sapiens

<400> SEQUENCE: 13
```

```
aacgcttcac gaatttgcgt                                                    20

<210> SEQ ID NO 14
<211> LENGTH: 26
<212> TYPE: DNA
<213> ORGANISM: Homo sapiens

<400> SEQUENCE: 14
gaggtagtag gttgtatagt ttagaa                                             26

<210> SEQ ID NO 15
<211> LENGTH: 19
<212> TYPE: DNA
<213> ORGANISM: Homo sapiens

<400> SEQUENCE: 15
aaagctagga ggctgtaca                                                     19

<210> SEQ ID NO 16
<211> LENGTH: 61
<212> TYPE: DNA
<213> ORGANISM: Artificial sequence
<220> FEATURE:
<223> OTHER INFORMATION: pLet7a-Luc reporter vector from Signosis, Inc.
<220> FEATURE:
<221> NAME/KEY: misc_feature
<222> LOCATION: (25)..(26)
<223> OTHER INFORMATION: n is a, c, g, or t

<400> SEQUENCE: 16
gaaaaatcag agagatcctc ataannaggc caagaagggc ggaaagtcca aattgctcga        60
g                                                                        61

<210> SEQ ID NO 17
<211> LENGTH: 63
<212> TYPE: DNA
<213> ORGANISM: Artificial Sequence
<220> FEATURE:
<223> OTHER INFORMATION: pLet7a-Luc reporter vector from Signosis, Inc.
<220> FEATURE:
<221> NAME/KEY: misc_feature
<222> LOCATION: (22)..(23)
<223> OTHER INFORMATION: n is a, c, g, or t
<220> FEATURE:
<221> NAME/KEY: misc_feature
<222> LOCATION: (46)..(47)
<223> OTHER INFORMATION: n is a, c, g, or t

<400> SEQUENCE: 17
tgatgaaagc tgcgcactag tnnaactata caacctacta cctcannaag cttaataaag        60
gat                                                                      63

<210> SEQ ID NO 18
<211> LENGTH: 49
<212> TYPE: DNA
<213> ORGANISM: Artificial Sequence
<220> FEATURE:
<223> OTHER INFORMATION: pLet7a-Luc reporter vector from Signosis, Inc.

<400> SEQUENCE: 18
cttttatttt cattggatct gtgtgttggt tttttgtatg cggccgcta                    49
```

SIRNA-MEDIATED INHIBITION OF DOUBLECORTIN AND CA2+/CALMODULIN-DEPENDENT KINASE-LIKE-1

CROSS REFERENCE TO RELATED APPLICATIONS

This application claims benefit under 35 U.S.C. 119(e) of provisional application U.S. Ser. No. 61/128,063, filed May 16, 2008. The entire contents of the above-referenced patent application are hereby expressly incorporated herein by reference.

STATEMENT REGARDING FEDERALLY SPONSORED RESEARCH OR DEVELOPMENT

Not Applicable.

BACKGROUND OF THE INVENTION

1. Field of the Invention

The present invention relates generally to methods of identification of stem cells, and more particularly, but not by way of limitation, to methods of identification of stem cells using a novel stem cell marker, as well as other methods of use of the novel stem cell marker in anti-cancer agents.

2. Brief Description of the Art

Cancer of the colon is the second most frequently diagnosed malignancy in the United States, as well as the third leading cause of cancer death. Colon cancer is a highly treatable and often curable disease when localized to the bowel. Surgery is the primary treatment and results in cure in approximately 50% of patients. However, recurrence and metastases following surgery is a major problem and often is the ultimate cause of death.

Due to its proximity, cancer of the colon often metastasizes to the small intestine. The prognosis of the cancer spreading to the small intestine is related to the degree of penetration of the tumor through the bowel wall and the presence or absence of nodal involvement. These two characteristics form the basis for all staging systems developed for colon cancer. Various characteristics also assist in prognosticating colon cancer and its spread to the small intestines. For example, bowel obstruction and bowel perforation are indicators of poor prognosis. Elevated pretreatment serum levels of carcinoembryonic antigen (CEA) and of carbohydrate antigen 19-9 (CA 19-9) also have a negative prognostic significance. However, age greater than 70 years at presentation is not a contraindication to standard therapies; acceptable morbidity and mortality, as well as long-term survival, are achieved in this patient population.

Cancer cells can also originate in the small intestine. However, this is a much rarer type of cancer. Symptoms of cancer of the small intestine typically include pain or cramps in the middle of the abdomen, weight loss without dieting, a lump in the abdomen, or blood in the stool.

Cancer of the stomach, also referred to as gastric cancer, also frequently metastasizes to the small intestine due to its proximity. This cancer is often difficult to diagnose in early stages and can be in the stomach for a long time, growing to a large size before symptoms arise. In the early stages of cancer of the stomach, an individual may experience indigestion and stomach discomfort, a bloated feeling after eating, mild nausea, loss of appetite or heartburn. In more advanced stages of stomach cancer, there may be blood in the stool, vomiting, weight loss or more severe pain.

Because of the frequency of these types of cancer (approximately 160,000 new cases of colon and rectal cancer per year alone), the identification of high-risk groups, the demonstrated slow growth of primary lesions, and the better survival of early-stage lesions, screening for gastrointestinal cancers should be a part of routine care for all adults starting at age 50, especially those with first-degree relatives with colorectal cancer.

Procedures used for detecting, diagnosing, monitoring, treating and preventing cancer of the colon, small intestine and/or stomach are of critical importance to the outcome of the patient. Patients diagnosed with early stage cancer generally have a much greater five-year survival rate as compared to the survival rate for patients diagnosed with distant metastasized cancers. New diagnostic methods which are more sensitive and specific for detecting early cancer of the stomach, small intestine and colon are clearly needed.

Patients with gastrointestinal cancers are closely monitored following initial therapy and during adjuvant therapy to determine response to therapy and to detect persistent or recurrent disease of metastasis. There is clearly a need for a cancer marker which is more sensitive and specific in detecting recurrence of these types of cancer.

Defining the mechanisms that regulate stem cell fate is critical in increasing our understanding of the neoplastic process. Tumorigenesis in the gut arises specifically in the stem cell (Clarke, 2005; de Lau, 2007; and He, 2007) population located at or near the base of the intestinal and colonic crypts, while transit cell populations originating from the stem cell zone become fully differentiated and are eventually sloughed into the lumen. The short life span of transit cells, whether they are mutated or not, limits their deleterious influence in the intestinal or colonic crypt (Potten, 2003; and Booth, 2002). Because no specific gut stem cell markers have been identified definitively (Bjerknes, 2005; and Kayahara, 2003), recognizing and assaying resident intestinal stem cells is quite difficult and has raised contentious argument; however, the microcolony assay following γ-irradiation is by definition a functional evaluation of intestinal stem cell fate (Withers, 1970) and can provide a mechanism for examining the early events of tumorigenesis. Because homeostatic mechanisms of stem cell proliferation are the same processes that become dysregulated in carcinogenesis (Sancho, 2003), a complete examination of these proliferation mechanisms holds medical significance in targeting future cancer treatments; therefore, a more detailed understanding of the pathways that regulate stem cell behavior is essential.

Recently, MSI-1 (Musashi-1) has been identified as a putative stem cell marker (Potten et al., (2003) Differentiation, 71:28-41). Musashi-1 was identified as an RNA binding protein that is a translational repressor of p21. Musashi-1 regulates asymmetric division in neural precursor cells, and is expressed in intestinal crypts in the stem cell zone. Its increased expression has also been observed in tumors in APC/Min mice. However, it has not been shown to be a reliable intestinal stem cell marker.

Pancreatic adenocarcinoma has the worst prognosis of any major malignancy with a 3% 5-year survival (Hoyer et al., 2006). Major obstacles in treating pancreatic cancer include extensive local tumor invasion and early metastasis. Recently, it has been proposed that pancreatic tumors arise specifically in the stem cell population located in these tissues. There is increasing evidence that a small subset of cells termed cancer stem cells (CSCs) or cancer initiating cells (CICs) are capable of initiating and sustaining tumor growth in transplantation assays (Diehn and Clarke, 2006). CSCs share unique properties with normal adult stem cells, including the ability to self-renew and differentiate. CSCs are often refractory to current standard chemotherapeutic agents and radiation therapies, as they are designed to eradicate actively cycling cells, not slowly cycling cancer stem cells. Thus novel therapies that specifically target the cancer stem cell population, either alone or in conjunction with current strategies, may be more effective in obliterating solid tumors.

The existence of CSCs was first demonstrated in acute myelogenous leukemia (Bonnet and Dick, 1997) and subsequently verified in breast (Al-Hajj et al., 2003), pancreatic (Li et al., 2007) and brain tumors (Singh et al., 2004a; Singh et al., 2003; Singh et al., 2004b). The CD133+ subpopulations from brain tumors could initiate clonally derived neurospheres in vitro showing self-renewal, differentiation, and proliferative characteristics similar to normal brain stem cells (Singh et al., 2004a; Singh et al., 2003; Singh et al., 2004b). Furthermore, transplantation of CD133+, but not CD133−, cells into NOD/SCID mice was sufficient to induce tumor growth in vivo. In a recent study, primary human pancreatic adenocarcinomas were implanted in immunocompromised mice to assess the ability of specific cell surface markers to identify a subpopulation of pancreatic cancer cells with enhanced tumorigenic potential (Li et al., 2007). A subpopulation of CD44+CD24+ ESA+ cells was identified as putative pancreatic cancer stem cells.

Tumor cell heterogeneity present in most solid tumors creates an enormous challenge for cancer eradication. Current strategies for inducing cell death generally target only the most rapidly proliferating cells within a tumor. Indeed, radiation therapy targets proliferating cells, which are the most sensitive to ionizing radiation (Cohn et al., 1997; Houchen et al., 2000; Riehl et al., 2000; Tessner et al., 1998); however, it is clear that effective tumor-eradication strategies must address the potential survival mechanisms unique to each particular cell type within the malignant population (i.e., quiescent stem cells). Currently, most traditional cancer therapies are based on their ability to kill most of the tumor population (i.e., log kill assays), but these treatments often fail to destroy cancer stem cells, which have been shown in several tumor types to be more resistant to standard chemotherapeutic agents (Li et al., 2007). This may explain why standard chemotherapy is effective in causing tumor shrinkage but often fails to prevent tumor recurrence, possibly due to the surviving cancer stem cell's ability to regenerate the tumor even after chemotherapeutic insult. This is not an unreasonable inference when one considers the gastrointestinal tract, where a single surviving intestinal stem cell is able to reconstitute an entire gastrointestinal crypt following severe genotoxic or cytotoxic injury (Bach et al., 2000).

Characterization of stem cells from the hematopoietic system, neural stem cells from the central nervous system and neural crest stem cells have emphasized the importance of specific cell surface antigens that permit the isolation of stem cells by fluorescence activated cell sorting (FACS). A candidate pancreatic stem cell, which is characterized by its expression of the neural stem-cell marker nestin and lack of established islet- and duct-cell markers, has been described in published reports (Abraham et al., 2004; Lechner et al., 2002; Zulewski et al., 2001). Furthermore, the basic helix-loop-helix transcription factor neurogenin 3 (NGN3) controls endocrine cell fate specification in uncommitted pancreatic progenitor cells. In the pancreas, NGN3-positive cells co-express neither insulin nor glucagon, demonstrating that NGN3 marks early precursors of pancreatic endocrine cells. Moreover, NGN3-deficient mice do not develop any islet cells and are diabetic. These data taken together demonstrate that NGN-3 and nestin are critical components of the pancreatic stem/progenitor cell compartment. A convincing recent study demonstrates that the adult mouse pancreas contains islet cell progenitors and that expansion of the β cell mass following injury induced by ligation of the pancreatic duct results in NGN3 gene expression and the ensuing differentiation of endogenous progenitor cells in a cell-autonomous, fusion-independent manner (Xu et al., 2008). These data demonstrate that functional islet progenitor cells can be induced in pancreatic ducts following injury.

Therefore, there is a need in the art for new and improved methods for detecting, diagnosing, monitoring, staging, prognosticating, imaging and treating gastrointestinal and pancreatic cancers. The present invention overcomes the disadvantages and defects of the prior art by providing such methods via a newly identified gastrointestinal and pancreatic stem cell marker.

BRIEF DESCRIPTIONS OF THE DRAWINGS

The patent or application file contains at least one drawing executed in color. Copies of this patent or patent application publication with color drawing(s) will be provided by the Office upon request and payment of the necessary fee.

FIG. 1 illustrates the expression pattern of DCAMKL-1 in normal mouse small intestine. (A) Immunohistochemical staining of normal small intestine for DCAMKL-1, arrow indicates the cell positive for DCAMKL-1 in the stem cell zone. (B) Pre-incubation with blocking peptide completely abolishes DCAMKL-1 immunoreactivity. (C) Immunohistochemical staining of normal small intestine for DCAMKL-1, brown color indicates the cells positive for DCAMKL-1 (indicated by the arrows).

FIG. 2 illustrates co-localization of Musashi-1 and DCAMKL-1 in mouse intestine. (A) Immunohistochemical staining of normal small intestine for DCAMKL-1 (brown color indicated by the arrow). (B) Immunohistochemical staining of normal small intestine for Musashi-1, brown color indicates the cells positive for Musashi-1 at the base of the crypts. (C) The cell positive for DCAMKL-1 stained red (indicated by the arrow) appears at the base of the crypt. (D) Intestinal section stained for Musashi-1 green. (E) Co-localization of DCAMKL-1 and Musashi-1 (yellow indicated by the arrow). The magnified inset image represents the single cell positive for both DCAMKL-1 and Musashi-1. (F) Co-staining of DCMAKL-1 (red color indicated by the arrow) with nuclear Hoechst 33342 (blue) staining. (G) Co-staining of Musashi-1 (green) with nuclear Hoechst 33342 (blue) staining. (H) Colocalization of DCAMKL-1 and Musashi-1 (yellow indicated by the arrow), co-stained with nuclear Hoechst 33342 (blue) staining. The magnified inset image represents the single cell positive for both DCAMKL-1 and Musashi-1 (yellow color).

FIG. 3 illustrates the fate of DCAMKL-1 positive cell following ionizing radiation (IR). (A) 6 h after whole body 6 Gy IR, morphologically appearing apoptotic cells were observed in the lower third of the intestinal crypt, but apoptosis is not observed in any of the DCAMKL-1 positive cells indicated by the arrow. (B) The small intestine stained for DCAMKL-1 (red) and TUNEL (green) to demonstrate apoptosis in the crypts 6 h following radiation. (C) Small intestine of unirradiated mice demonstrating no staining for phospho-H2AX. The crypt area is magnified in the inset. (D) 6 h post IR; small intestine demonstrates DNA damage by positive phospho-H2AX staining (DAB brown). The crypt area is magnified in the inset. (E) 6 h post IR; small intestine demonstrates DNA damage in the DCAMKL-1 positive cell indicated by the arrow. The magnified inset image represents the single cell positive for both DCAMKL-1 and phospho-H2AX. (F) After 24 h after IR, the appearance of multiple DCAMKL-1 immunoreactive mitotic figures indicated by 'M' were noted adjacent to morphologically appearing apoptotic cells indicated by arrows that were also expressing DCAMKL-1.

FIG. 4 illustrates DCAMKL-1 expression in the regenerative crypts post IR. (A) 84 h following IR, no DCAMKL-1 expression could be detected in regenerative crypts. (B) Staining at 144 h after IR demonstrates restoration of DCAMKL-1 expression in the intestinal crypt indicated by arrows.

FIG. 5 illustrates the histological evaluation of small intestine of APC/min mice. (A) Scattered single cells were immunoreactive for DCAMKL-1 in the intestinal crypts (arrow) and a trend towards increased expression on villi (arrow head). (B) DCAMKL-1 staining within adenomas of APC/min mice indicated by the arrows. DCAMKL-1 was also immunoreactive in the cells within the villus epithelium surrounding the adenoma (arrow head). (C) APC/min intestinal adenoma immunostained with anti-PCNA (red) and co-stained with DCAMKL-1 (brown). The cells immunoreactive for DCAMKL-1 are indicated by the arrows. (D) Portion of (A) magnified to demonstrate the cell positive for DCAMKL-1 is not immunoreactive for PCNA. (E) Double staining of PCNA and DCAMKL-1 in putative stem cell zone of wild-type mouse demonstrates the quiescent state of the DCAMKL-1 expression cell indicated by the arrow.

FIG. 6 illustrates β-Catenin expression in the small intestine of APC/min mice localized with DCAMKL-1. (A) Normal appearing APC/min mice intestine immunostained for membrane β-Catenin (brown) and cytoplasmic DCAMKL-1 (red) co-immunostaining indicated by arrow. (B) Magnified image of (A) demonstrating the cell positive for DCAMKL-1 and β-Catenin indicated by arrow. (C) DCAMKL-1 expressing cell (arrow) along with other cells demonstrating nuclear translocation of β-Catenin within an APC/min adenoma indicated by the arrow, just adjacent to normal membrane β-Catenin staining epithelium. (D) Magnified image of (C) demonstrating the DCAMKL-1 positive cell indicated by the arrow.

FIG. 7 illustrates the colonic distribution of DCAMKL-1 and structure of cell positive for DCAMKL-1. (A) The cell positive for DCAMKL-1 appears at the midpoint of the colonic crypt in the proximal colon. (B) In distal colon, the distribution of DCAMKL-1 expression appears at the base of the colonic crypt. (C) The close views of DCAMKL-1 expressing cells within the colon and distal jejunum (D) demonstrates the axonal-like process.

FIG. 8 illustrates pancreatic DCAMKL-1 expression and specific islet cell type differentiation in adult mice. (A) DCAMKL-1 expression (brown) in the main pancreatic duct (left—arrows) and in the periphery of pancreatic islets (middle—arrows). No DCAMKL-1 expression was observed in acinar cells or accessory ducts (right). (B) Immunofluorescence demonstrating DCAMKL-1 (red) and somatostatin (green) staining of pancreatic islets. Co-localization is demonstrated with arrows in the merged image. (C) DCAMKL-1 (red) and glucagon (green) immunofluorescence staining of pancreatic islets. No colocalization is observed in the merged image. (D) Immunofluorescence demonstrating DCAMKL-1 (red) and insulin (green) staining of pancreatic islets. No co-localization is observed in the merged image. In the immunofluorescence staining: Nuclei were stained blue with Hoechst in the merged images.

FIG. 9 illustrates DCAMKL-1 and other putative pancreatic stem cell markers. (A) The pancreatic tissue of newborn mice shows distinct DCAMKL-1 staining (left—arrows) and NGN3 (right—arrows). (B) Immunofluorescence staining for DCAMKL-1 (red) and NGN3 (green) are indicated with arrows in the pancreas of newborn mice. Merged image reveals distinct co-localization of DCAMKL-1 and NGN3. Representative cells are indicated by arrows and nuclei are stained blue with Hoechst dye. (C) Adult mouse pancreatic tissue serial sections stained with DCAMKL-1 (left—arrows), NGN3 (middle—arrows) and nestin (right—arrows). (D) Immunoperoxidase staining for DCAMKL-1 (purple) and nestin (brown) in pancreatic islet of an adult mouse (left). Magnified images of the left panel show distinctly separate staining for DCAMKL-1 (red arrow) and nestin (black arrow) (middle panel), and co-localization of DCAMKL-1 and nestin (right panel), as indicated by the arrow.

FIG. 10 illustrates DCAMKL-1 and 14-3-3 σ expression in human pancreatic adenocarcinoma. (A) DCAMKL-1 expression (brown) in histologically normal appearing tissue from pancreatic cancer resection specimen (top left). Spindle-shaped cytoplasmic staining of DCAMKL-1 in neoplastic pancreatic islet tissue (top right). DCAMKL-1 expression in ductal epithelial cells of pancreatic adenocarcinoma (bottom left). Intervening stromal elements demonstrate fibrillar DCAMKL-1 immunoreactivity (bottom right). Representative cells are indicated by arrows. (B) Staining for 14-3-3 σ (purple) and DCAMKL-1 (brown) at the islet periphery in normal appearing pancreatic tissue (left). In a magnified portion of the left image, a representative cell demonstrating the cytoplasmic expression of 14-3-3 σ is indicated with arrow (right). (C) 14-3-3 σ (purple) and DCAMKL-1 (brown) expression in pancreatic adenocarcinoma (left). In a magnified portion of the left image, nuclear localized 14-3-3 σ (purple) in individual cells co-localized with cytoplasmic DCAMKL-1 (brown) indicated by arrowhead (right). Fibrillar DCAMKL-1 staining in the intervening stroma is indicated by arrows. (D) Left image demonstrates DCAMKL-1 (brown) expression in ductal epithelium of a PanIN type lesion, a representative cell is indicated by arrow. Image on the right demonstrates intense cytoplasmic and nuclear staining of 14-3-3 σ (purple) and cytoplasmic DCAMKL-1 (brown) in a PanIN lesion. Representative cell demonstrating nuclear 14-3-3 σ co-localized with DCAMKL-1 is indicated by arrow. Insets in the images on the right in the panel B, C and D are magnified images.

FIG. 11 illustrates DCAMKL-1 and vimentin expression in human pancreatic adenocarcinoma. (A) Arrow in the left image indicates a single slender DCAMKL-1 expressing cell in a PanIN type lesion. A single elongated vimentin expressing cell in the ductal epithelium of a PanIN type lesion as indicated by arrow (right). (B) Immunofluorescence staining for DCAMKL-1 (red) and vimentin (green) in a PanIN lesion. Merged images reveal distinct co-localization of DCAMKL-1 and vimentin as indicated by arrows with nuclei stained blue with Hoechst dye. (C) Immunofluorescence staining for DCAMKL-1 (red) and vimentin (green) in stromal compartment of pancreatic adenocarcinoma. Merged images demonstrate immunolocalization of DCAMKL-1 and vimentin with nuclei stained blue with Hoechst dye.

FIG. 12 illustrates DCAMKL-1 expression in $Pdx48^{Cre}$-activated $KRAS^{G12D}$ pancreatic cancer mouse model. Pancreatic tissues from 5-month-old WT littermate (A) and from 5-month-old (B) $Pdx48^{Cre}$ activated $KRAS^{G12D}$ mouse were immunostained for DCAMKL-1. (C) A magnified portion of the image (B) demonstrating cells positive for DCAMKL-1 in the pancreatic duct. (D) A magnified portion of the image (B) demonstrating cells positive for DCAMKL-1 in the islets. Brown colored cells (arrows) indicate cells positive for DCAMKL-1. These data demonstrate an increased expression of DCAMKL-1 correlated with progressive neoplastic changes.

FIG. 13 illustrates FACS-based isolation of DCAMKL-1 cells from mouse pancreas. FACS-based isolation of cells from mouse pancreas using anti-DCAMKL-1 antibody. FACS plot of sorted cells. (A) side scatter oval gate R1. (B) Polygon gate R2 represents sorted fluorescent cells from gate R1 (0.36% of total cells). (C) Single cells following FACS with brightfield overlay.

FIG. 14 illustrates that DCAMKL-1 sorted cells demonstrate growth in vitro and in vivo. (A) FACS isolated DCAMKL-1 cells in suspension culture at day 1 (left) and demonstrating spheroid formation at day 21 (right). (B) Athymic nude mice 4 weeks after subcutaneous injection with either matrigel alone (left) or spheroid with matrigel, arrow indicates nodular growth (right). (C) Image demonstrates a tan grey soft tissue outgrowth with blood vessel formation under the skin of the DCAMKL-1 spheroid-injected mouse as indicated by the arrows. (D) Image on the left demonstrates soft tissue from DCAMKL-1 spheroid injection stained with H&E for histological evaluation. Cells which appeared to be epithelial in nature formed early islet-like structures, as indicated by arrows. Image on the right demonstrates groups of cells, which lined up around central spaces and appeared to be poorly formed glands (arrow). (E) Cells around the central spaces were positive for cytokeratin-14, indicating glandular epithelial origin (top left—arrow) and PDX-1, a marker of early pancreatic development (top right—arrow). Islet formations expressed the endocrine markers somatostatin (bottom left—arrow) and secretin (bottom right—arrow).

FIG. 15 illustrates a schematic representation of cell surface expression of DCAMKL-1. The C-terminus of DCAMKL-1 is predicted to be outside the cell surface and thus allows for recognition with antibody directed to this domain, which facilitates the isolation of DCAMKL-1 cells by FACS.

FIG. 16 illustrates the expression of DCAMKL-1 in the mouse small intestine. (A): Brown indicates DCAMKL-1+ cells (arrows). (B): Quantitative representation of DCAMKL-1 expressing cells as measured by cell position in intestinal crypts. (C): Co-immunofluorescence staining for DCAMKL-1 (red—arrow, left panel) and ChrA (green—arrow head, middle panel) in crypts. No co-localization was observed in the merged image (right panel). (D): DCAMKL-1 (red—arrow, left panel) and pPTEN (green—arrow head, middle panel) in crypts. No co-localization was observed in the merged image (right panel). (E): DCAMKL-1 (red—arrow, left panel) and pAKT (green—arrow head, middle panel) in crypts. No co-localization was observed in the merged image (right panel). (F): DCAMKL-1 (red—arrow, left panel) and somatostatin (green—arrow head, middle panel) in crypts. No co-localization was observed in the merged image (right panel). (G): DCAMKL-1 (red—arrow, left panel) and secretin (green—arrow head, middle panel) on villus. No co-localization was observed in the merged image (right panel).*Nuclei in all merged images are stained blue with Hoechst 33342 DNA dye.

FIG. 17 illustrates LGR5 and DCAMKL-1 in the mouse small intestine. (A): Brown indicates LGR5+ cells (arrowheads). (B): Brown indicates DCAMKL-1+ cell (arrow). (C and D): Co-immunostaining for LGR5 (purple—arrowhead) and DCAMKL-1 (brown—arrow). No co-localization of LGR5 and DCAMKL-1 was observed in the putative stem cell zone (C) or CBC cells (D). Black box in (C) demonstrates a cell negative for both LGR5 and DCAMKL-1. (E-H): Co-immunofluorescence staining for LGR5 (green) (E) and DCAMKL-1 (red—arrow) (F). No co-localization of LGR5 and DCAMKL-1 was observed in merged images (G) and (H). *Nuclei in merged image (H) are stained blue with Hoechst 33342 DNA dye.

FIG. 18 illustrates that LGR5 and DCAMKL-1 mark proliferative and non-proliferative cells respectively in the mouse small intestine. Co-immunofluorescence staining for PCNA (green) (A) and LGR5 (red—arrowheads) (B). PCNA+LGR5+ cells are indicated with arrowheads in the merged image (C). PCNA (green) (D) and DCAMKL-1 (red—arrow) (E). A PCNA-DCAMKL-1+ cell is indicated by the arrow in the merged image (F). *Nuclei in all merged images (C and F) are stained blue with Hoechst 33342 DNA dye.

FIG. 19 illustrates that DCAMKL-1 identifies the quiescent anchored stem cell. Following mLRA, mouse intestines (distal jejunum) were immunostained for BrdUrd (brown) at day 7 (A) magnified in (B) and at day 10 (C) magnified in (D). (E-F): Mouse intestines 10 days post 8 Gy IR were co-immunostained for DCAMKL-1 (brown) and BrdUrd (purple) or PCNA (purple). (E): Arrow indicates a BrdUrd+ (label retaining) and DCAMKL-1+ cell. (F): Arrow indicates a PCNA- (quiescent) and DCAMKL-1+ cell.

FIG. 20 illustrates the isolation of intestinal stem cells using DCAMKL-1 based FACS. (A): Schematic diagram depicting the predicted cell surface expression and extracellular C-terminal domain of DCAMKL-1. (B): Western blot analyses demonstrating cell surface expression of DCAMKL-1 following biotinylation (Pierce Cell Surface Protein Isolation Kit). Biotinylated cell surface protein extract from intact cells (see FIG. 21) demonstrated the presence of DCAMKL-1 (Lane B), but not in the unbound non-biotinylated intracellular protein extract fraction (Lane N). As a positive control, EGFR a known cell surface expressing protein was detected only in the bound fraction. (C): A representative Alexa Fluor® 568 conjugated DCAMKL-1+ cell following FACS (red); nucleus is stained blue with Hoechst 33342 DNA dye post-sorting. (D): A single DCAMKL-1 sorted cell in suspension culture at day 0. (E): A spheroid containing 50-100 cells at day 21. Isotransplantation assays: (F): Matrigel alone injected control mouse, (G): spheroid injected mouse demonstrating nodular growth on the flank (arrow), H&E staining of excised nodules from (H) control mouse and (I) spheroid injected mouse (arrow indicates glandular formation). Spheroid injected nodule stained for (J): cytokeratin-14, (K): Msi-1, (L): Math1 and (M): L-FABP, with representative cells indicated by arrows.

FIG. 21 illustrates confocal imaging of biotinylated extracellular membrane proteins in SW480 cells. Biotinylation of intact SW480 cells (used to isolate cell surface proteins) as demonstrated by incubation with streptavidin conjugated Cy3™ (red) (A) and co-localized with the transmembrane protein E-cadherin (FITC—green) (B). Merged images with Hoechst DNA stain (blue) demonstrate that biotinylation is restricted to the extracellular membrane surface (C). Control cells without biotinylation reagent do not show staining for streptavidin conjugated Cy3™ (red) (D), but do exhibit staining for E-cadherin (green) and Hoechst (blue) (E and F).

FIG. 22 illustrates FACS-based isolation of DCAMKL-1 cells from the mouse intestine. (A): FACS plot of side scatter (chosen based on previous sorting experiments) of cells stained with Alexa Fluor® 568 conjugated DCAMKL-1 antibody. Gate R1 indicates localization of the DCAMKL-1+ fluorescing cell population. (B): These cells were further gated through R2 based on fluorescence intensity. (C): FACS plot of side scatter of unstained control cells. (D): No cells were detected within gate R2.

Figure 25:
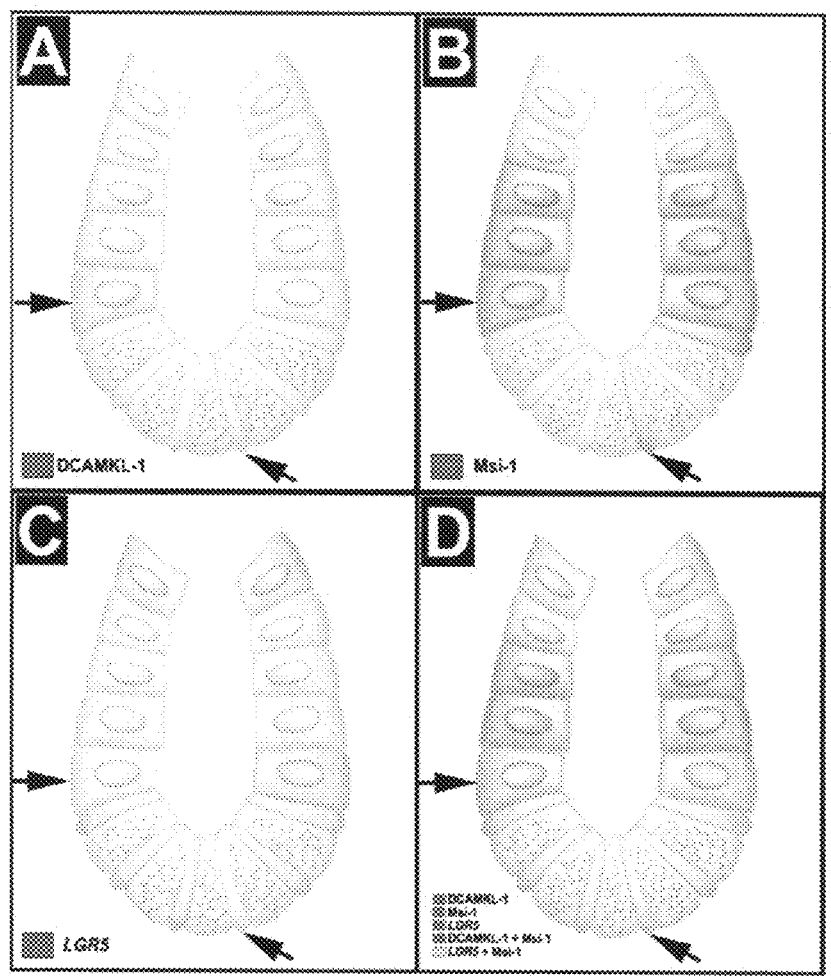

FIG. 25 provides a schematic illustration of the location of putative stem and progenitor cell markers in the mouse small intestine. (A): DCAMKL-1 (red), (B): Msi-1 (green) and (C): LGR5 (blue). (D): Merged image represents areas of predicted co-localization. Arrows indicate the position of DCAMKL-1 expressing cells.

FIG. 26 graphically illustrates a map of pLet7a-Luc Reporter Vector (LR-0037) (Signosis, Inc. CA) demonstrating the presence of the let7a binding site at the 3'UTR of Luciferase gene.

Figure 27:
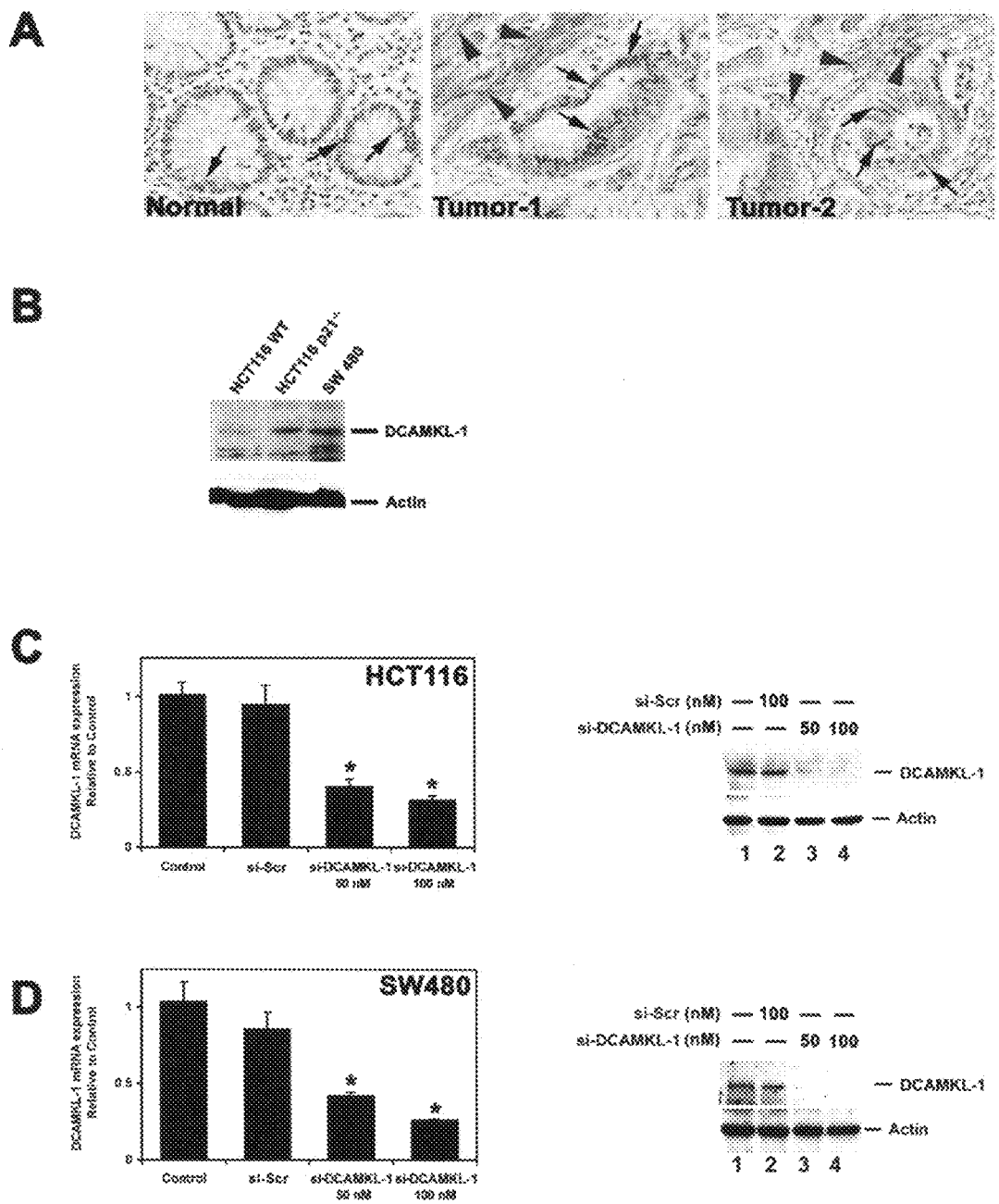

FIG. 27 illustrates that DCAMKL-1 is overexpressed in colorectal cancer. (A) Immunohistochemistry for DCAMKL-1 (brown) in normal (left panel) and two different colon cancer tissues (middle and right panels). Black arrow indicates representative epithelial cells positive for DCAMKL-1. Blue arrow head indicates the presence of DCAMKL-1 in the stromal compartment. (B) Western blot demonstrating the expression of DCAMKL-1 in three different colon cancer cell lines. Actin serves as control. (C) DCAMKL-1 specific siRNA (si-DCAMKL-1) decreases DCAMKL-1 mRNA (left panel) and protein expression (right panel) in HCT116 colon cancer cells compared to controls. (D) Similar decrease in DCAMKL-1 mRNA (left panel) and protein (right panel) observed following si-DCAMKL-1 transfection in SW480 colon cancer cells. For C and D, values in the bar graphs are given as average±SEM and * denote statistically significant differences (*p<0.01) compared to control. All the experiments were performed in triplicates and were repeated 3 times.

FIG. 28 illustrates that DCAMKL-1 is essential for tumor growth. (A) HCT116 cells were injected into the flanks of athymic nude mice (n=5 per group) to generate tumors. At day 15 siRNAs (si-DCAMKL-1 and si-Scr) were injected directly into the tumors and followed by injections every third day (inset). After 5 injections, tumors were excised at day 28 and are represented above. Tumor sizes with standard error are shown from data collected at the time of every injection. (B) si-DCAMKL-1 treatment resulted in significantly decreased tumor weight when compared to controls. (C) The expression of DCAMKL-1 mRNA in the tumors quantitated by real-time RT-PCR. (D) Western blot analysis for DCAMKL-1 was performed on tumors samples as indicated. For A-C, values are given as average±SEM and * denote statistically significant differences (*p<0.01) compared to control.

FIG. 29 illustrates that knockdown of DCAMKL-1 induces pri-let-7a miRNA. (A) Quantitative real-time RT-PCR analysis for pri-let-7a miRNA in tumor xenografts. siRNA mediated knockdown of DCAMKL-1 results in increased expression of pri-let-7a miRNA. (B) si-DCAMKL-1 treated HCT116 cells demonstrate increased expression of pri-let-7a miRNA. (C) Similar induction of pri-let-7a miRNA was observed in SW480 cells. For A-C, values are given as average±SEM and * denote statistically significant differences (p<0.01) compared to control.

Figure 30:
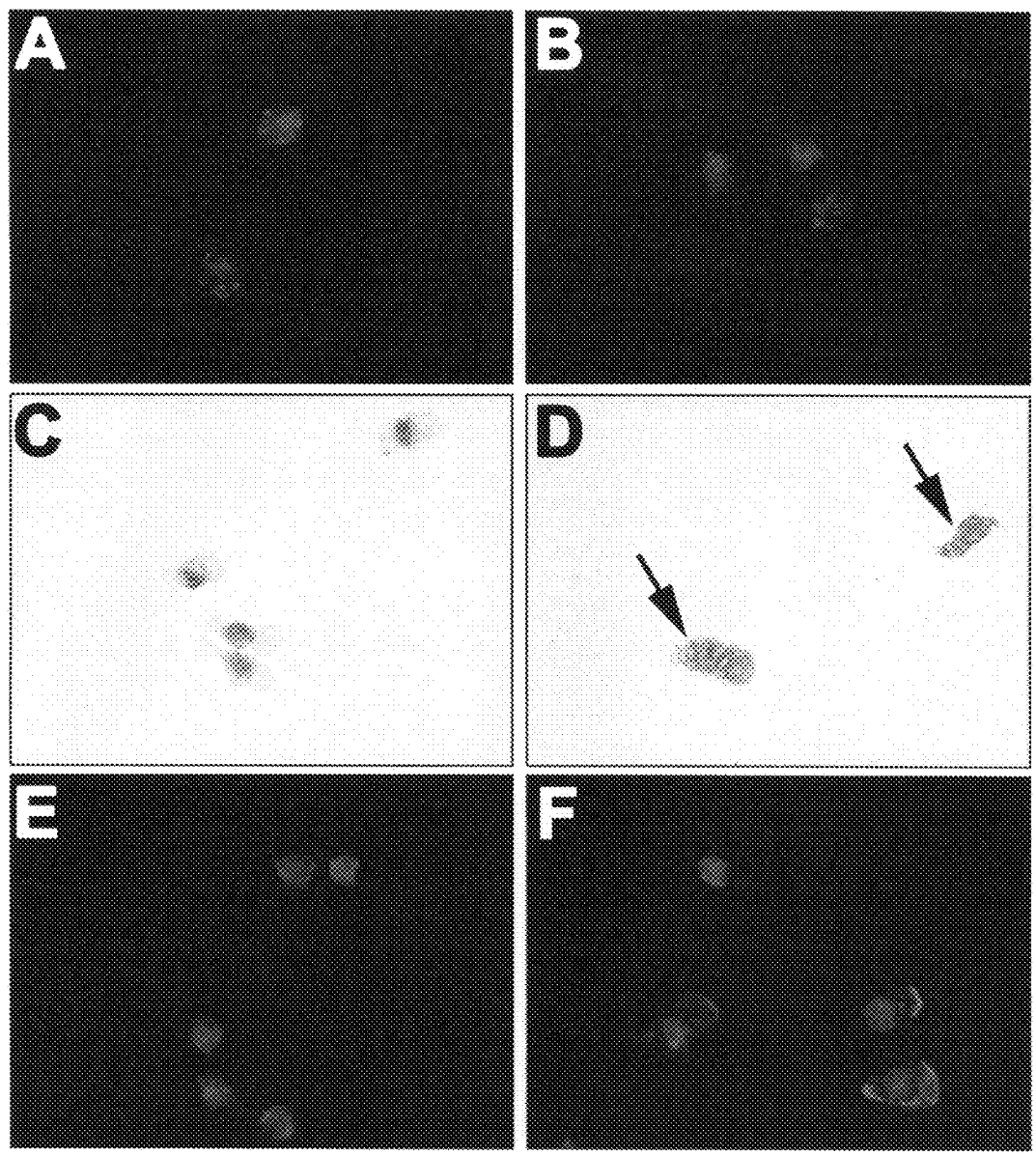

FIG. 30 illustrates that DCAMKL-1 positive cells are less differentiated. A representative image of Alexa Fluor® 568 conjugated DCAMKL-1 positively sorted cells (A) (red) and negatively sorted cells (B) following FACS. (C) Brightfield image of L-FABP immunostaining. DCAMKL-1 positive cells do not express L-FABP. (D) DCAMKL-1 negative cells express L-FABP (brown—arrows). (E) Fluorescent image of L-FABP immunostaining. DCAMKL-1 positive cells do not express L-FABP. (F) L-FABP was found in DCAMKL-1 negative cells (green). Nuclei in A, B, E and F are stained blue with Hoechst 33342 DNA dye post-sorting.

FIG. 31 illustrates that DCAMKL-1 inhibits let-7a miRNA. (A) Intestinal stem cells (DCAMKL-1+) isolated from normal mouse intestine demonstrate decreased pri-let-7a compared to more differentiated cells (DCAMKL-1-). (B) Real-time RT-PCR data demonstrate an increased expression of DCAMKL-1 mRNA in DCAMKL-1+ sorted stem cells compared to more differentiated (DCAMKL-1-) cells. siRNA mediated knockdown of DCAMKL-1 decreases luciferase activity (Relative Luciferase Units—RLU) following transfection with plasmid encoding luciferase containing let-7a binding site in HCT116 (C) and SW480 cells (D). For A-D, values are given as average±SEM and * denote statistically significant differences (p<0.01) compared to control.

Figure 32:
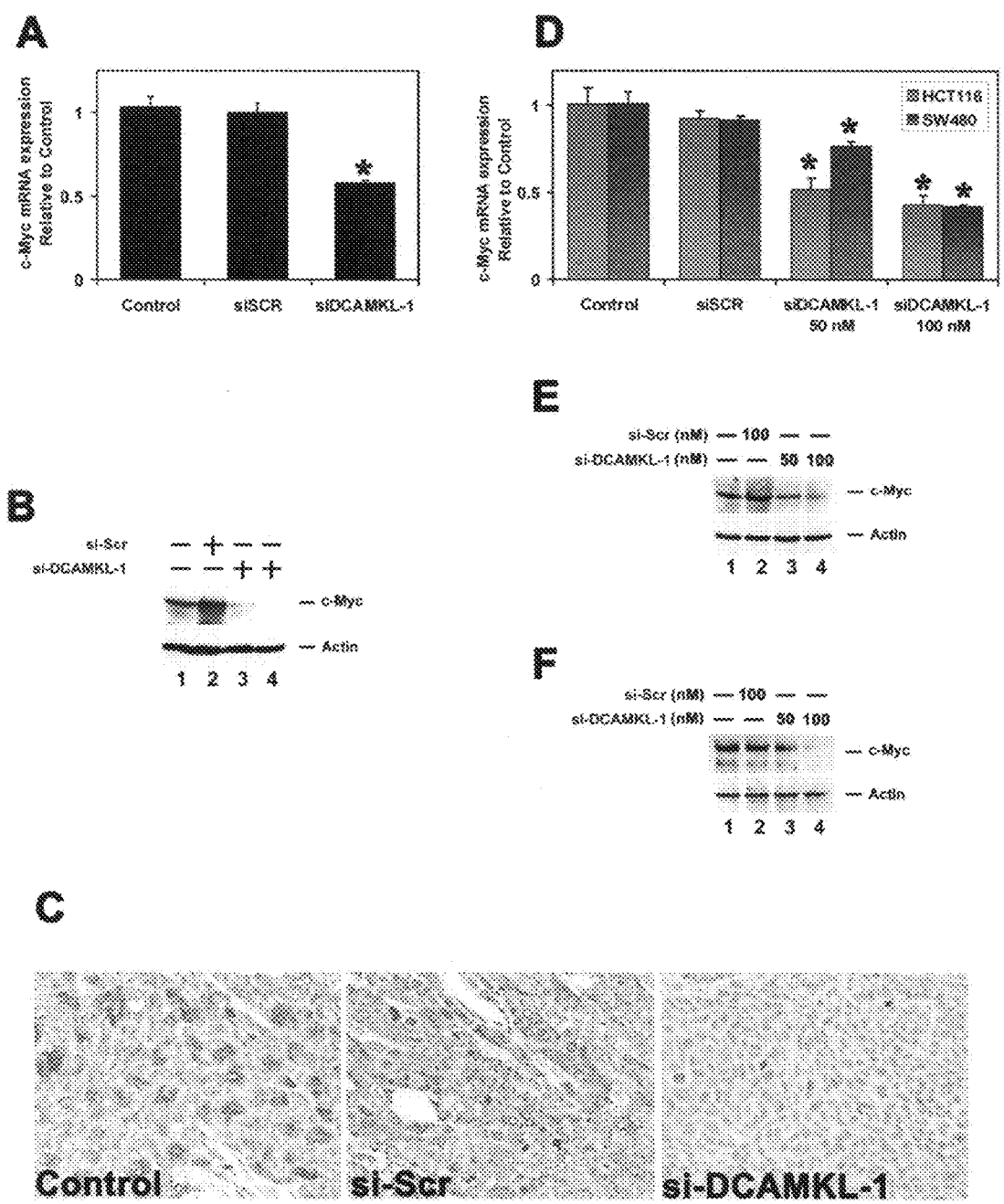

FIG. 32 illustrates that downregulation of DCAMKL-1 results in decreased expression of a let-7a downstream target. A decreased expression of c-Myc mRNA (A) and protein (B) was observed in HCT116 tumor xenografts following the knockdown of DCAMKL-1. (C) Decreased c-Myc expression (brown) in si-DCAMKL-1 treated tumors compared to controls by immunohistochemical analysis. siRNA mediated knockdown of DCAMKL-1 results in decreased c-Myc mRNA (D) and protein (E) in HCT116 cells. (D and F) Similar decrease was observed in SW480 cells. For bar graph in A and D, values are given as average±SEM and * denote statistically significant differences (*p<0.01) compared to control.

DETAILED DESCRIPTION OF THE INVENTION

Before explaining at least one embodiment of the invention in detail by way of exemplary drawings, experimentation, results, and laboratory procedures, it is to be understood that the invention is not limited in its application to the details of construction and the arrangement of the components set forth in the following description or illustrated in the drawings, experimentation and/or results. The invention is capable of other embodiments or of being practiced or carried out in various ways. As such, the language used herein is intended to be given the broadest possible scope and meaning; and the embodiments are meant to be exemplary—not exhaustive. Also, it is to be understood that the phraseology and terminology employed herein is for the purpose of description and should not be regarded as limiting.

Unless otherwise defined herein, scientific and technical terms used in connection with the present invention shall have the meanings that are commonly understood by those of ordinary skill in the art. Further, unless otherwise required by context, singular terms shall include pluralities and plural terms shall include the singular. Generally, nomenclatures utilized in connection with, and techniques of, cell and tissue culture, molecular biology, and protein and oligo- or polynucleotide chemistry and hybridization described herein are those well known and commonly used in the art. Standard techniques are used for recombinant DNA, oligonucleotide synthesis, and tissue culture and transformation (e.g., electroporation, lipofection). Enzymatic reactions and purification techniques are performed according to manufacturer's specifications or as commonly accomplished in the art or as described herein. The foregoing techniques and procedures are generally performed according to conventional methods well known in the art and as described in various general and more specific references that are cited and discussed throughout the present specification. See e.g., Sambrook et al. Molecular Cloning: A Laboratory Manual (2nd ed., Cold Spring Harbor Laboratory Press, Cold Spring Harbor, N.Y. (1989) and Coligan et al. Current Protocols in Immunology (Current Protocols, Wiley Interscience (1994)), which are incorporated herein by reference. The nomenclatures utilized in connection with, and the laboratory procedures and techniques of, analytical chemistry, synthetic organic chemistry, and medicinal and pharmaceutical chemistry described herein are those well known and commonly used in the art. Standard techniques are used for chemical syntheses, chemical analyses, pharmaceutical preparation, formulation, and delivery, and treatment of patients.

As utilized in accordance with the present disclosure, the following terms, unless otherwise indicated, shall be understood to have the following meanings:

The terms "DCAMKL-1", "Doublecortin-like and CAM kinase kinase-like 1", "doublecortin and $Ca^{2+}$/calmodulin-dependent kinase-like-1" and "Gene Ontogeny (GO)-enriched transcript" will be used herein interchangeably and will be understood to refer to a microtubule-associated kinase expressed in post-mitotic neurons. See for example, Shu et al. (Neuron (2006) 49:25-39; and Biol. Chem. (2006) 281:11292-300). Its presence was identified from cDNA libraries prepared from laser capture microdissected small intestinal and gastric epithelial progenitor populations.

RNA interference (hereinafter "RNAi") is a method of post-transcriptional gene regulation that is conserved throughout many eukaryotic organisms. RNAi is induced by short (i.e., <30 nucleotide) double stranded RNA ("dsRNA") molecules which are present in the cell. These short dsRNA molecules, called "short interfering RNA" or "siRNA," cause the destruction of messenger RNAs ("mRNAs") which share sequence homology with the siRNA. It is believed that the siRNA and the targeted mRNA bind to an "RNA-induced silencing complex" or "RISC", which cleaves the targeted mRNA. The siRNA is apparently recycled much like a multiple-turnover enzyme, with 1 siRNA molecule capable of inducing cleavage of approximately 1000 mRNA molecules. siRNA-mediated RNAi degradation of an mRNA is therefore more effective than currently available technologies for inhibiting expression of a target gene.

Specific methods of using siRNAs are described in detail in U.S. Pat. Nos. 7,345,027, issued to Tolentino et al. on Mar. 18, 2008; 7,148,342, issued to Tolentino et al. on Dec. 12, 2006; 7,511,025, issued to Wyatt et al. on Mar. 31, 2009; and 7,511,132, issued to Khvorova et al. on Mar. 31, 2009; the entire contents of such patents are expressly incorporated herein by reference. These patents describe siRNAs which specifically target and cause RNAi-induced degradation of mRNA, such as RNA from VEGF and VEGF receptors, MMP-1 and BCL-2, respectively, and such siRNA compounds may be used to suppress invasion and/or metastasis of tumor cells and/or inhibit angiogenesis, in particular for the treatment of cancerous tumors, age-related macular degeneration, and other angiogenic diseases. The methods of these patents may be applied to the production and use of siRNAs in accordance with the presently disclosed and claimed invention.

The term "biological sample" as used herein will be understood to refer to a sample of biological tissue or fluid. Biological samples include, but are not limited to, sections of tissues such as biopsy and autopsy samples, frozen sections taken for histological purposes, blood, plasma, serum, sputum, stool, tears, mucus, hair, skin, explants and primary and/or transformed cell cultures derived from patient tissues.

The phrase "providing a biological sample" as used herein refers to obtaining a biological sample for use in methods described in this invention. Most often, this will be done by removing a sample of cells from an animal, but can also be accomplished by using previously isolated cells (e.g., isolated by another person, at another time and/or for another purpose), or by performing at least a portion of the methods of the invention in vivo.

As used herein, a "conjugate" refers to a molecule that contains at least one receptor-binding ligand and at least one anticancer agent that are coupled directly or via a linker and that are produced by chemical coupling methods or by recombinant expression of chimeric DNA molecules to produce fusion proteins.

As used herein, the term "covalently coupled", "linked", "bonded", "joined", and the like, with reference to the ligand and anticancer agent components of the conjugates of the present invention, mean that the specified components are either directly covalently bonded to one another or indirectly covalently bonded to one another through an intervening moiety or components, such as a bridge, spacer, linker or the like. For example but not by way of limitation, the ligand and the anticancer agent may be chemically coupled together via a thioether linkage as described in Mickisch et al. (1993).

As used herein, the term "anticancer agent" refers to a molecule capable of inhibiting cancer cell function. The agent may inhibit proliferation or may be cytotoxic to cells. A variety of anticancer agents can be used and include those that inhibit protein synthesis and those that inhibit expression of certain genes essential for cellular growth or survival. Anticancer agents include those that result in cell death and those that inhibit cell growth, proliferation and/or differentiation. In one embodiment, the anticancer agent is selectively toxic against certain types of cancer cells but does not affect or is less effective against other normal cells.

The term "antineoplastic agent" is used herein to refer to agents that have the functional property of inhibiting a development or progression of a neoplasm in a human or animal, particularly a malignant (cancerous) lesion, such as a carcinoma, sarcoma, lymphoma, or leukemia. Inhibition of metastasis is frequently a property of antineoplastic agents.

The term "effective amount" refers to an amount of a biologically active molecule or conjugate or derivative thereof sufficient to exhibit a detectable therapeutic effect without undue adverse side effects (such as toxicity, irritation and allergic response) commensurate with a reasonable benefit/risk ratio when used in the manner of the invention. The therapeutic effect may include, for example but not by way of limitation, inhibiting the growth of undesired tissue or malignant cells. The effective amount for a subject will depend upon the type of subject, the subject's size and health, the nature and severity of the condition to be treated, the method of administration, the duration of treatment, the nature of concurrent therapy (if any), the specific formulations employed, and the like. Thus, it is not possible to specify an exact effective amount in advance. However, the effective amount for a given situation can be determined by one of ordinary skill in the art using routine experimentation based on the information provided herein.

As used herein, the term "concurrent therapy" is used interchangeably with the terms "combination therapy" and "adjunct therapy", and will be understood to mean that the patient in need of treatment is treated or given another drug for the disease in conjunction with the pharmaceutical compositions of the presently disclosed and claimed invention. This concurrent therapy can be sequential therapy where the patient is treated first with one drug and then the other, or the two drugs are given simultaneously.

The terms "administration" and "administering", as used herein will be understood to include all routes of administration known in the art, including but not limited to, oral, topical, transdermal, parenteral, subcutaneous, intranasal, mucosal, intramuscular and intravenous routes, including both local and systemic applications. In addition, the methods of administration may be designed to provide delayed or controlled release using formulation techniques which are well known in the art.

The term "pharmaceutically acceptable" refers to compounds and compositions which are suitable for administration to humans and/or animals without undue adverse side effects such as toxicity, irritation and/or allergic response commensurate with a reasonable benefit/risk ratio.

By "biologically active" is meant the ability to modify the physiological system of an organism. A molecule can be biologically active through its own functionalities, or may be biologically active based on its ability to activate or inhibit molecules having their own biological activity.

The term "receptor" as used herein will be understood to include any peptide, protein, glycoprotein, polycarbohydrate, or lipid that is uniquely expressed or overexpressed on the surface of cancer cells and is exposed on the surface of cancer cells in a manner that will allow interaction with a circulating targeting agent, such as the conjugate.

As used herein, "substantially pure" means an object species is the predominant species present (i.e., on a molar basis it is more abundant than any other individual species in the composition), and preferably a substantially purified fraction is a composition wherein the object species comprises at least about 50 percent (on a molar basis) of all macromolecular species present. Generally, a substantially pure composition will comprise more than about 80 percent of all macromolecular species present in the composition, more preferably more than about 85%, 90%, 95%, and 99%. Most preferably, the object species is purified to essential homogeneity (contaminant species cannot be detected in the composition by conventional detection methods) wherein the composition consists essentially of a single macromolecular species.

A "liposome" is a small vesicle composed of various types of lipids, phospholipids and/or surfactant. The components of the liposome are commonly arranged in a bilayer formation, similar to the lipid arrangement of biological membranes.

The terms "cancer" and "cancerous" refer to or describe the physiological condition in mammals that is typically characterized by unregulated cell growth. Examples of cancer include but are not limited to, carcinoma, lymphoma, blastoma, sarcoma, and leukemia. More particular examples of such cancers include squamous cell cancer, small-cell lung cancer, non-small cell lung cancer, gastrointestinal cancer, pancreatic cancer, glioblastoma, cervical cancer, ovarian cancer, liver cancer, bladder cancer, hepatoma, breast cancer, colon cancer, colorectal cancer, endometrial carcinoma, salivary gland carcinoma, kidney cancer, renal cancer, prostate cancer, vulval cancer, thyroid cancer, hepatic carcinoma and various types of head and neck cancer.

The term "metastasis" as used herein will be understood to refer to the spread of cancer from a primary tumor to other parts of the body. Metastasis is a sequential, multistep process in which tumor cells detach from a primary tumor, migrate through the basement membrane and extracellular matrix, and invade the lymphatic and/or blood systems. This is followed by the establishment of secondary tumors at distant sites.

The term patient includes human and veterinary subjects. "Mammal" for purposes of treatment refers to any animal classified as a mammal, including human, domestic and farm animals, nonhuman primates, and any other animal that has mammary tissue.

The term "healthy patient" as used herein will be understood to refer to a patient who is free of cancer.

The terms "treat", "treating" and "treatment", as used herein, will be understood to include both inhibition of tumor growth as well as induction of tumor cell death.

As used herein, the term "treating cancer" or "treatment of cancer" means to inhibit the spread of cancer, decrease tumor size, lessen or reduce the number of cancerous cells in the body, or ameliorate or alleviate the symptoms associated with the cancer. The treatment is considered therapeutic if there is a decrease in mortality and/or morbidity, or a decrease in disease burden manifested by reduced numbers of malignant cells in the body.

"Preventing cancer" or "prevention of cancer" is intended to mean preventing the occurrence or recurrence of the disease state of cancer. As such, a treatment that impedes, inhibits, or interferes with metastasis, tumor growth, or cancer proliferation is deemed preventive.

As used herein, "managing cancer" encompasses preventing the recurrence of cancer in a patient who had suffered from cancer, lengthening the time a patient remains in remission, preventing the occurrence of cancer in patients at risk of suffering from cancer (e.g., patients who had been exposed to high amounts of radiation or carcinogenic materials; patients infected with viruses associated with the occurrence of cancer; and patients with genetic predispositions to cancer), and preventing the occurrence of malignant cancer in patients suffering from pre-malignant or non-malignant cancers.

Administering a therapeutically effective amount or prophylactically effective amount is intended to provide a therapeutic benefit in the treatment, prevention, or management of cancer. The specific amount that is therapeutically effective can be readily determined by the ordinary medical practitioner, and can vary depending on factors known in the art, such as the type of cancer, the patient's history and age, the stage of cancer, the co-administration of other anti-cancer agents, including radiation therapy.

The presently disclosed and claimed invention is related to methods of inhibiting tumor growth. Such methods involve an inhibition of doublecortin and $Ca^{2+}$/calmodulin-dependent kinase-like-1 (DCAMKL-1) protein in the tumor cells. Such method results in a decrease in cancer cell proliferation and apoptosis, as well as $G_2$/M arrest, coupled with mitotic catastrophe. Inhibition of DCAMKL-1 may also result in a decrease in mRNA stability and/or translation for the gene products of at least one of c-Myc, KRAS, and combinations thereof, and may also result in an increase in miRNA expression, such as but not limited to, pri-let-7a miRNA expression. The expression of DCAMKL-1 protein can be inhibited using any well known method that targets the RNA binding protein's gene or its mRNA. These methods include, but are not limited to, the use of antisense oligonucleotides, ribozymes, nucleic acid molecules that promote triple helix formation, and short-interfering RNAs (siRNAs) or co-repression of a target gene by introducing a homologous gene fragment into the cell that harbors the target gene. In particular embodiments, the methods of the presently disclosed and claimed invention employ siRNAs that specifically reduce expression of DCAMKL-1 protein.

In one embodiment, the expression of DCAMKL-1 protein is inhibited by the use of an RNA interference technique referred to as RNAi. RNAi allows for the selective knockout of a target gene in a highly effective and specific manner. This technique involves introducing into a cell double-stranded RNA (dsRNA), having a sequence corresponding to the exon portion of the target gene. The dsRNA causes a rapid destruction of the target gene's mRNA.

RNAi can be performed, for example, using chemically-synthesized RNA. Alternatively, suitable expression vectors can be used to transcribe such RNA either in vitro or in vivo. In vitro transcription of sense and antisense strands (encoded by sequences present on the same vector or on separate vectors) can be effected using for example T7 RNA polymerase, in which case the vector can contain a suitable coding sequence operably-linked to a T7 promoter. The in vitro-transcribed RNA can, in certain embodiments, be processed (e.g., using E. coli RNase III) in vitro to a size conducive to RNAi. The sense and antisense transcripts are combined to form an RNA duplex which is introduced into a target cell of interest. Other vectors can be used, which express small hairpin RNAs (shRNAs) which can be processed into siRNA-like molecules. Various vector-based methods are described in, for example, Brummelkamp et al. (Science (2002) 296:550-3); Lee et al. (Nat. Biotechnol. (2002) 20:500-5); Miyagashi and Taira (Nat. Biotechnol. (2002) 20:497-500); Paddison et al. (Proc. Natl. Acad. Sci. USA (2002) 99:1443-8); Paul et al. (2002); and Sui et al. (Proc. Natl. Acad. Sci. USA (2002) 99:5515-20). Various methods for introducing such vectors into cells, either in vitro or in vivo (e.g., gene therapy), are known in the art.

Kits for production of dsRNA for use in RNAi are available commercially, e.g., from New England Biolabs, Inc. and Ambion Inc. (Austin, Tex., USA). Methods of transfection of dsRNA or plasmids engineered to make dsRNA are routine in the art.

The methods described herein may be utilized for treatment of any cancer, including but not limited to, cancers of the gastrointestinal tract, colon, pancreas, breast, prostate, lung and ovaries. Particular cancers that can be treated and managed by the methods of the presently disclosed and claimed invention include, but are not limited to, those associated with an increase in the expression of DCAMKL-1 protein.

In one embodiment, the presently disclosed and claimed invention is directed to a short-interfering ribonucleic acid (siRNA) molecule effective at silencing DCAMKL-1 expression. The siRNA molecule comprises a sense RNA strand and an antisense RNA strand, wherein the sense and antisense RNA strands form an RNA duplex, and wherein the sense RNA strand comprises a nucleotide sequence identical to a target sequence of about 15 to about 25 contiguous nucleotides in DCAMKL-1 mRNA (or a homolog thereof). The DCAMKL-1 target sequence that binds the siRNA can be selected experimentally or empirically. In certain embodiments, the DCAMKL-1 mRNA may be in accordance with SEQ ID NO:1, or the DCAMKL-1 mRNA may encode the amino acid sequence of SEQ ID NO:2; in particular embodiments, the sense RNA strand may comprise SEQ ID NO:3.

Alternatively, depending on the conditions under which binding is sufficient to disrupt the function of the DCAMKL-1 gene, a sequence complementary to a target sequence within the DCAMKL-1 nucleic acid sequences need not be 100 percent identical to the target sequence. For example, a sequence can be complementary to its target sequence when at least about 80 or 90 percent of its nucleotides bind via matched base pairings with nucleotides of the target sequence.

Therefore, the sense RNA strand may comprise a sequence homologous to a portion of SEQ ID NO:1 (or a mRNA encoding SEQ ID NO:2) that is capable of hybridizing to its target sequence under stringent conditions. In general, for complementary sequences to hybridize under stringent conditions, said sequences are at least 80 or 90 percent identical to each other. One non-limiting example of stringent hybridization conditions includes 6× sodium chloride/sodium citrate (SSC) at about 45° C., followed by 0.2×SSC, 0.1% SDS at 50-65° C. Thus, the presently disclosed and claimed invention also includes siRNAs having a sense RNA strand that comprises a nucleotide sequence that is at least 90% identical to a target sequence of about 15 to about 25 contiguous nucleotides in DCAMKL-1 mRNA (or a homolog thereof).

The siRNAs of the presently disclosed and claimed invention may include modifications to their sugar-phosphate backbone or nucleosides. These modifications can be tailored to promote selective genetic inhibition, while avoiding a general panic response reported to be generated by siRNA in some cells. Moreover, modifications can be introduced in the bases to protect siRNAs from the actin of one or more endogenous degradative enzymes.

The presently disclosed and claimed invention also includes a pharmaceutical composition comprising any of the siRNA molecules described herein above. The pharmaceutical composition may further comprise at least one additional chemotherapeutic agent, as described in detail herein. In addition, the pharmaceutical composition may also further comprise a delivery agent, such as but not limited to, a liposome.

Certain pharmaceutical compositions are single unit dosage forms suitable for oral, mucosal (e.g., nasal, sublingual, vaginal, buccal, or rectal), parenteral (e.g., subcutaneous, intravenous, bolus injection, intramuscular, or intraarterial), or transdermal administration to a patient. Examples of dosage forms include, but are not limited to, tablets; caplets; capsules, such as soft elastic gelatin capsules; cachets; troches; lozenges; dispersions; suppositories; ointments; cataplasms (poultices); pastes; powders; dressings; creams; plasters; solutions; patches; aerosols (e.g., nasal sprays or inhalers); gels; liquid dosage forms suitable for oral or mucosal administration to a patient, including suspensions (e.g., aqueous or non-aqueous liquid suspensions, oil-in-water emulsions, or a water-in-oil liquid emulsions), solutions, and elixirs; liquid dosage forms suitable for parenteral administration to a patient; and sterile solids (e.g., crystalline or amorphous solids) that can be reconstituted to provide liquid dosage forms suitable for parenteral administration to a patient.

The formulation should suit the mode of administration. For example, oral administration requires enteric coatings to protect the agents of the invention from degradation within the gastrointestinal tract. In another example, the agents of the invention may be administered in a liposomal formulation to shield the agents from degradative enzymes, facilitate transport in circulatory system, and effect delivery across cell membranes to intracellular sites.

The composition, shape, and type of dosage forms of the pharmaceutical compositions of the presently disclosed and claimed invention will typically vary depending on their use. For example, a dosage form used in the acute treatment of a disease may contain larger amounts of one or more of the active ingredients it comprises than a dosage form used in the chronic treatment of the same disease. Similarly, a parenteral dosage form may contain smaller amounts of one or more of the active ingredients it comprises than an oral dosage form used to treat the same disease. These and other ways in which specific dosage forms encompassed by the invention will vary from one another and will be readily apparent to those skilled in the art. See, e.g., Remington: The Science and Practice of Pharmacy, Alfonso R. Gennaro, editor, 20th ed. Lippincott Williams & Wilkins: Philadelphia, Pa., 2000.

In one embodiment, the presently disclosed and claimed invention also includes a method of inhibiting expression of DCAMKL-1 protein. Said method includes providing a cell expressing DCAMKL-1 and providing the siRNA molecule described herein above; the cell is then contacted with the siRNA, thereby specifically inhibiting the expression of DCAMKL-1.

The presently disclosed and claimed invention also includes a method of inhibiting expression of DCAMKL-1 protein in a subject. In said method an effective amount of the pharmaceutical composition described herein above is administered to the subject, thereby specifically inhibiting the expression of DCAMKL-1.

The presently disclosed and claimed invention further includes a method of inhibiting tumor growth. In said method, at least one of the siRNAs described herein above is provided and contacted with the tumor, thereby specifically inhibiting the expression of DCAMKL-1 in the tumor and thus inhibiting growth of the tumor. Said method may result in at least one of (1) a decrease in cancer cell proliferation, apoptosis, $G_2/M$ arrest, mitotic catastrophe; (2) a decrease in at least one of mRNA stability and mRNA translation for at least one protein selected from the group consisting of c-Myc, KRAS and combinations thereof; and (3) an increase in miRNA expression, such as pri-let-7α miRNA expression.

The presently disclosed and claimed invention also includes a method of inhibiting tumor growth in a subject, which includes providing at least one of the pharmaceutical compositions described herein above and administering an effective amount thereof to the subject, thereby specifically inhibiting the expression of DCAMKL-1 in the tumor and thus inhibiting growth of the tumor. Said method may result in at least one of (1) a decrease in cancer cell proliferation, apoptosis, $G_2/M$ arrest, mitotic catastrophe; (2) a decrease in at least one of mRNA stability and mRNA translation for at least one protein selected from the group consisting of c-Myc, KRAS and combinations thereof; and (3) an increase in miRNA expression, such as pri-let-7α miRNA expression.

Delivery of the agents of the presently disclosed and claimed invention (e.g., siRNAs) into a patient can either be direct, i.e., the patient is directly exposed to an agent of the invention or agent-carrying vector, or indirect, i.e., cells are first transformed with the nucleic acid sequences encoding an agent of the invention in vitro, then transplanted into the patient for cell replacement therapy. These two approaches are known as in vivo and ex vivo therapy, respectively.

The presently disclosed and claimed invention is also directed to a method of generating a tumor cell. Such method includes providing at least one of a primary cell and an immortalized cell, and introducing a gene encoding DCAMKL-1 into the cell such that the cell overexpresses the DCAMKL-1 protein and exhibits increased cell proliferation and induction of anchorage independent growth. Such generated tumor cell may then be utilized as a model system for identifying novel therapeutics for cancer therapy.

The presently disclosed and claimed invention is also directed to a diagnostic method for cancer detection, progression and/or prognosis. Such diagnostic method involves the detection of DCAMKL-1 protein as a marker. The method may also include detection of the specific level of DCAMKL-1 protein present and comparison thereof to known levels of DCAMKL-1 protein present in normal cells and in cells at various stages of tumor progression and/or metastasis.

The present invention is also related to a method for the detection of at least one cancer cell to aid in the diagnosis of neoplastic diseases, such as but not limited to, cancers of the gastrointestinal tract, colon, pancreas, breast, prostate, lung and ovaries. The method includes the steps of providing a biological sample from a patient, providing a composition comprising an agent that specifically binds to DCAMKL-1 protein, contacting the biological sample with the composition under conditions appropriate for formation of a complex between the composition and DCAMKL-1 protein present on a surface of at least one cancer cell, detecting the presence of any complex formed, and determining that at least one cancer cell is present in the biological sample if complex is detected. The method may further include measuring the amount of complex formed, and correlating the amount of complex formed to the diagnosis of neoplastic disease. The present invention further relates to an immunological kit comprising at least one specific binding agent for DCAMKL-1 protein and auxiliary reagents for measurement of DCAMKL-1 protein.

The above-described method could also be utilized to determine the effect of chemopreventive strategies on the development of early neoplastic lesions.

The term "specific binding agent" as used herein will be understood to include any compound or agent that binds specifically to DCAMKL-1 protein, including but not limited to, a receptor for DCAMKL-1 protein, a lectin binding to DCAMKL-1 protein, or an antibody to DCAMKL-1 protein. As the skilled artisan will appreciate, the term "specific" is used to indicate that other biomolecules present in the sample do not significantly bind to the binding agent specific for DCAMKL-1 protein. A level of less than 5% cross-reactivity is considered not significant.

In one embodiment, the specific binding agent is an antibody reactive with DCAMKL-1 protein. The term antibody refers to a polyclonal antibody, a monoclonal antibody, fragments of such antibodies, as well as to genetic constructs comprising the binding domain of an antibody.

The monoclonal antibody or other specific binding agent may further comprise a label, such as but not limited to, a radiolabel or fluorescent label, to aid in visualization of tumor cells with an external imaging source, such as but not limited to, an MRI or PET scan.

The present invention also relates to a method of treating a neoplastic disease by targeting an anticancer agent, such as but not limited to a cytotoxic agent, to a gastrointestinal and/or pancreatic stem cell in a patient with a gastrointestinal and/or pancreatic tumor. The method includes providing a conjugate of the anticancer agent attached to a specific binding agent for DCAMKL-1 protein, and administering an effective amount of such conjugate to the patient, thereby inhibiting growth of the tumor. The anticancer agent may be a chemotherapeutic agent. In addition, the conjugate could also be attached to an implantable biodegradable agent.

The above-described method of treating a neoplastic disease could also be utilized to prevent neoplastic diseases, by administering the conjugate (or any of the other compositions disclosed herein) to a patient not experiencing a cancer. Depletion of gastrointestinal and/or pancreatic stem cells in the patient will act to deplete the potential for neoplasia and tumor formation.

The present invention also relates to a method for diagnosing at least one of (1) the severity of a gut and/or pancreatic injury following exposure to a DNA damaging agent, and (2) the severity of colitis (colonic ulceration and inflammation). The method includes the steps of providing a biological sample from a patient, identifying stem cells present in the biological sample using a specific binding agent that recognizes DCAMKL-1 protein, and measuring an effect on at least one of stem cell apoptosis, senescence, proliferation and cell division of the DCAMKL-1 positive cells when compared to DCAMKL-1 positive cells not exposed to the conditions listed under (1) or (2). This technique could also be used to measure the response to anti-inflammatory therapies for IBD and other non-specific collitidies.

While the above-described methods have been disclosed as useful with gastrointestinal (GI) and pancreatic tumors, such methods are not specifically limited to use with GI and pancreatic tumors. For example, targeted depletion of a cancer or adenoma-initiating stem cell, as described herein, would also be useful with solid tumors of both GI and non-GI origin (such as but not limited to, lung cancer).

The present invention is also related to methods of isolating GI and/or pancreatic stem cells in non-cancerous patients. The method includes the steps of providing a biological sample of gastrointestinal and/or pancreatic tissue from a patient and providing the composition comprising an agent that specifically binds to DCAMKL-1 as described herein above. The biological sample is then contacted with the composition under conditions appropriate for formation of a complex between the composition and DCAMKL-1 present on a surface of at least one cancer cell. Cells having the composition attached thereto are then isolated, followed by separating the composition from the cells. The isolated GI and/or pancreatic stem cells could be used for sorting experiments, and these multipotent cells could be cultured and their differentiation directed into other gut and/or pancreatic cell types. Optionally, the GI and/or pancreatic stem cells can be cultured and used to re-populate damaged intestinal and/or pancreatic epithelial cells exposed to severe injury.

Examples are provided hereinbelow. However, the present invention is to be understood to not be limited in its application to the specific experimentation, results and laboratory procedures. Rather, the Examples are simply provided as one of various embodiments and are meant to be exemplary, not exhaustive.

Example 1

Colorectal cancer is a major cause of cancer death in the western world. Mutational activation of oncogenes joins with inactivation of tumor suppressor genes to produce colorectal tumors [Clark, 2006]. The transformation of normal mucosal epithelial cells into invasive colorectal carcinoma occurs via a synchronized accumulation of mutations in a series of critical genes [Fearon, 1990]. The long time span between initiation and gross development of tumors presents an enormous challenge in dissecting the critical molecular mechanisms that regulate neoplastic change.

Defining the mechanisms that regulate stem cell fate is critical in increasing our understanding of the neoplastic process. Tumorigenesis in the gut is thought to arise specifically in the stem cell [Sansom et al., 2005; de Lau et al., 2007] population located at or near the base of the intestinal and colonic crypts. Transit cell populations originating from the stem cell zone become fully differentiated and are eventually sloughed into the lumen. Transit cells' short life span, whether they are mutated or not, limits their deleterious influence in the intestinal or colonic crypt [Potten, 2003]. Because no specific gut stem cell markers have been identified definitively [Bjerknes et al., 2005; Kayahara et al., 2003], recognizing and assaying resident intestinal stem cells is quite difficult and has raised contentious argument; however, the microcolony assay following γ-irradiation (IR) is by definition a functional evaluation of intestinal stem cell fate [Withers et al., 1970] and can potentially provide a mechanism for examining the early events of tumorigenesis. Because homeostatic mechanisms of stem cell proliferation are the same processes that become dysregulated in carcinogenesis [Sancho et al., 2003], a complete examination of these proliferation mechanisms holds medical significance in targeting future cancer treatments; therefore, a more detailed understanding of the pathways that regulate stem cell behavior is essential.

As we work toward a complete understanding of these pathways that regulate stem cell behavior, one major obstacle in the study of gastrointestinal stem cell biology has been the lack of definitive markers to identify gastrointestinal stem cells. The presently disclosed and claimed invention confirms that DCAMKL-1 a microtubule-associated kinase expressed in post-mitotic neurons [Lin et al., 2000] is an intestinal stem cell marker. This discovery allows one to assay resident intestinal stem cells and their response to genotoxic injury. DCAMKL-1 was identified as a Gene Ontogeny-enriched (or GO-enriched) transcript expressed in comparison with GEP (gastric epithelial progenitor) and whole stomach libraries [Giannakis et al., 2006]. Immunohistochemical analysis using antibodies directed at DCAMKL-1 revealed single cell staining in scattered intestinal crypt cross-sections at or near position 4 and in gastric isthmus cells in the putative stem cell location. The radiation-injury model was chosen to investigate its effects on stem cell fate for several reasons: (1) the kinetics of radiation injury has been extensively characterized in the small intestine in mice [Potten, 1990; Wright, 2000]; (2) radiation injury can be induced uniformly throughout the gut at discreet points in time; and (3) the extent of radiation injury on crypt clonogenic survival can be varied with the dose of radiation. In this Example, immunohistochemical analysis was employed in order to visualize crypt epithelial stem cells and to determine the cell specific DCAMKL-1 expression at baseline and in response to radiation injury in adult mice.

Materials and Methods for Example 1

Immunohistochemistry: (a) Brightfield: Heat Induced Epitope Retrieval (HIER) was performed on 4 mm paraffin-embedded mouse small intestine and colon sections utilizing a pressurized de-cloaking chamber (Biocare Medical, LLC) and incubated in citrate buffer (pH 6.0) at 99° C. for 18 min. The sections were then washed three times with PBS (Sigma), and endogenous biotin activity was blocked using Avidin/Biotin blocking kit (Vector Lab) and/or with DCAMKL-1 blocking peptide (ABGENT) wherever indicated according to manufacturer's instructions. Further, endogenous peroxidase activity was quenched with 3% hydrogen peroxide. After washing, the slides were then incubated in horse normal serum (2%) and BSA (1%) at room temperature for 20 min to block non-specific binding. The sections were then exposed to primary antibodies rabbit anti-DCAMKL-1 (ABGENT), rabbit anti-Musashi-1 (ABCAM), rabbit PCNA (proliferating cell nuclear antigen) (Santa Cruz), goat β-catenin (Santa Cruz), rabbit anti phospho H2AX (Cell Signaling) overnight at refrigerator temperature. Slides were then washed three times with PBS and incubated in the appropriate secondary antibody biotinylated donkey anti-rabbit, donkey anti-goat (Jackson Immuno Research Lab) 30 min at room temperature. Slides were washed again and then incubated in SA-HRP (Dako) at room temperature for 12 min. After final wash in PBS, chromogenic development was performed utilizing DAB (brown) and/or AEC (red) substrate (Sigma). All slides were counterstained with hematoxylin (Biocare Medical), dehydrated in graded alcohols, cleared in xylene, and permanently mounted with cryoseal (Richard-Allen).

(b) Fluorescence: HIER was performed on 4 mm paraffin-embedded tissue sections utilizing a pressurized de-cloaking chamber (Biocare Medical, LLC) and incubated in citrate buffer (pH 6.0) at 99° C. for 18 min. After washing three times with PBS, the slides were then incubated in horse normal serum (2%) and BSA (1%) at room temperature for 20 min to block nonspecific binding. Sections were then sequentially exposed to rabbit anti-DCAMKL-1 (ABGENT) for 1 hr at 30° C. and its appropriate secondary Cy3 conjugated donkey anti-rabbit (Jackson Immuno Research Lab) for 30 min at room temperature. Finally fluorescein conjugated TUNEL staining was performed using "In situ Cell Death Kit" (Roche diagnostics), according to manufactures instructions. The slides were then wet-mounted and counterstained utilizing Vectashield with DAPI (Vector). For co-staining of DCAMKL-1 with Musashi-1, the slides were incubated with normal goat serum after decloaking and exposed to rabbit anti-DCAMKL-1 (ABGENT) for 1 hr at 30° C. and its appropriate secondary goat anti-rabbit Alexa Fluoro 568 (Invitrogen) for 30 min at room temperature. Further, the slides were blocked with normal goat and normal donkey serum and exposed to rabbit anti-Musashi-1 (ABCAM) for 1 hr at 30° C. and its appropriate secondary donkey anti-rabbit Alexa Fluoro 488 (Invitrogen) for 30 min at room temperature. Then the slides are washed with Hoechst 33342 for staining of the nucleus.

(c) Microscopic Examination: Slides were examined using Nikon 80i microscope base. For brightfield, 60× digital images were taken with PlanAPO objective and DXM1200C camera (Nikon). Fluorescent images were taken with 60× PlanFluoro objective and 2× optical converter for a final magnification of 120×, utilizing CoolSnap ES2 camera (Photometrics). Filter sets were used employing excitation ranges for Cy3, FITC, and DAPI. All images were captured utilizing NIS-Elements software (Nikon) and further processed using Adobe Photoshop 8.0 software.

Results for Example 1

Localization of DCAMKL-1, a putative intestinal stem cell marker. In wild-type (WT) adult mouse intestine (FIG. 1A), it was confirmed that immunoreactive DCAMKL-1 is expressed primarily in single cells in the putative stem cell zone in adult conventionally housed C57 Bl/6 mice. In rare sections villus staining was observed, particularly at the crypt villus junction (data not shown). Distinct cytoplasmic staining was observed at baseline while DCAMKL-1 expression was a rare event. Staining was present in approximately one in six intestinal crypt cross-sections on average. Immunostaining of the proposed columnar longitudinal epithelial cell interspersed between paneth cells is also observed. These columnar longitudinal epithelial cells have been previously shown to the putative stem cell marker musashi-1 (MSI-1) [Kayahara et al., 2003; Potten et al., 2003]. Preincubation with DCAMKL-1 blocking peptide (Abcam) completely abolished DCAMKL-1 immunoreactivity (FIG. 1B).

Figure 2:
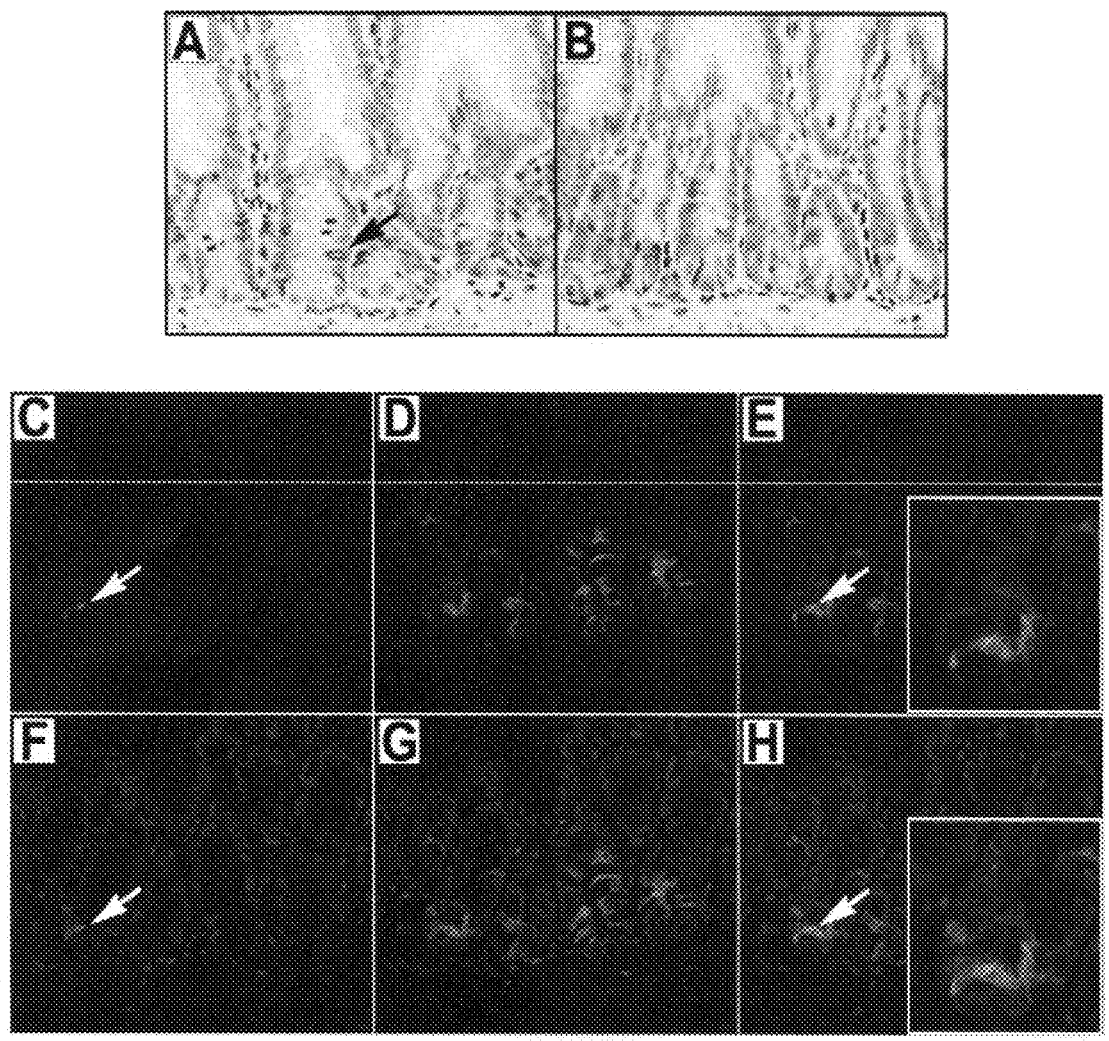

Colocalization of DCAMKL-1 and MSI-1. In order to determine whether DCAMKL-1 was expressed in the same cells that expressed the putative stem cell marker MSI-1, immunostaining for MSI-1 was performed using the intestines of adult WT uninjured mice. In FIG. 2A, distinct DCAMKL-1 staining was once again observed in the crypt. In FIG. 2B crypt epithelial staining for MSI-1 was observed in several cells at the base of the crypt including cell position 4 just above the paneth cell zone, consistent with its reported stem cell localization. Furthermore immunofluorescence microscopy and double immunostaining were used for DCAMKL-1 and MSI-1. Single cell staining for DCAMKL-1 was again observed in the stem cell zone (FIG. 2C). MSI-1 staining was also observed in the crypts (FIG. 2D). Distinct colocalization was observed however (FIG. 2H) with DCAMKL-1 and MSI-1 (orange). These data demonstrate that DCAMKL-1 is expressed in the same cell as MSI-1, but likely represents a subset of MSI-1 expressing cells. Nuclei stained with Hoechst 33342 (blue) is demonstrated in FIGS. 2F-G.

Figure 3:
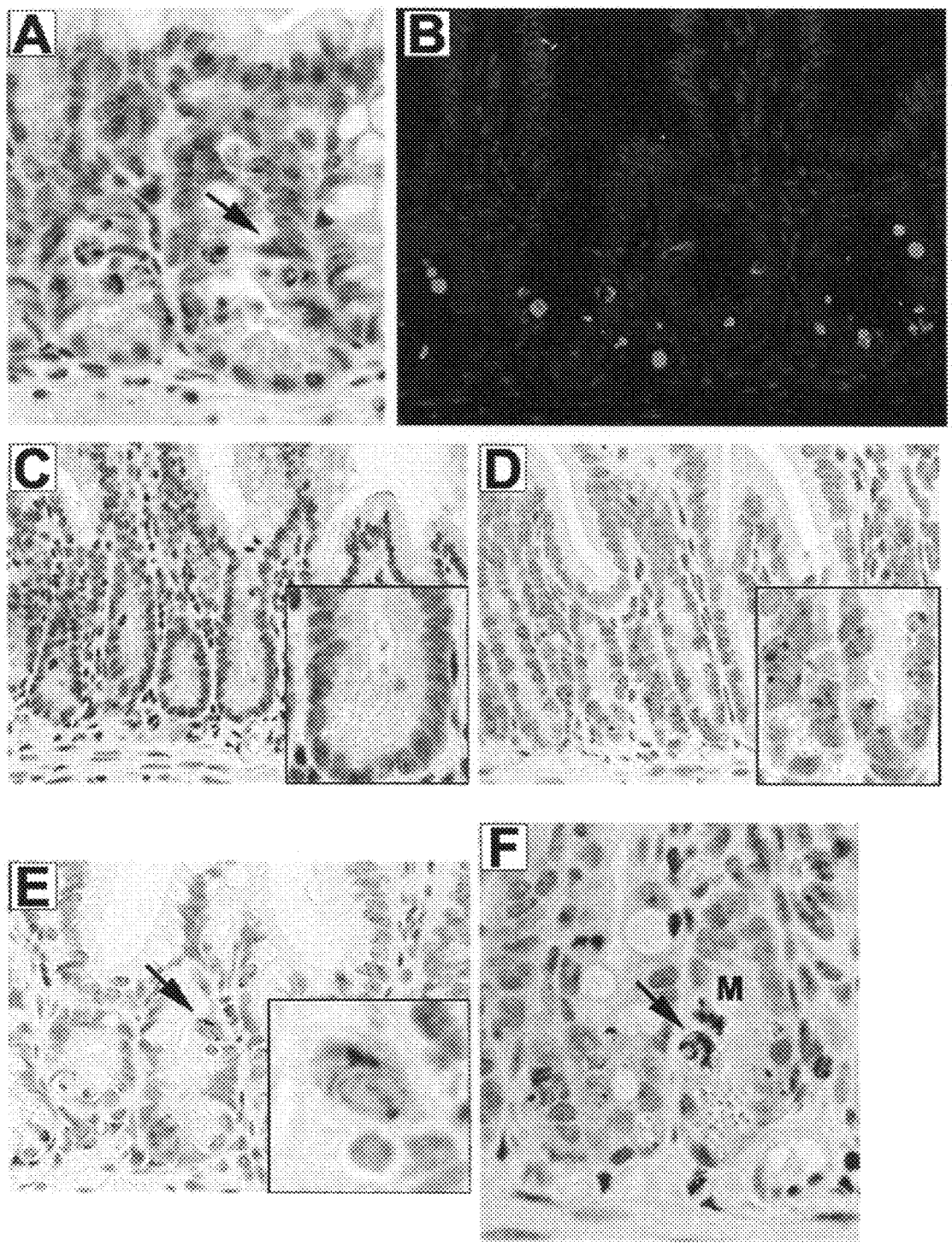

Fate of DCAMKL-1 positive cell in response to radiation injury. To investigate whether DCAMKl-1 expression was upregulated following ionizing radiation (IR), adult mice were treated with whole body 6 Gy IR, at doses sufficient to induce epithelial apoptosis in the stem cell zone [Houchen, et al, 2000; Merritt et al., 1994; Radtke et al., 2005]. Initially, the 6 hour after 6 Gy IR time point was chosen, as this is the time when maximal p53 dependent apoptosis is observed in the intestinal crypt [Merritt et al., 1994]. Here DCAMKL-1 staining similar to that observed at baseline was demonstrated (FIG. 3A). Following 6 Gy IR, morphologically appearing apoptotic cells were observed in the lower third of the intestinal crypt with a typical distribution following IR (FIG. 3A arrows). Surprisingly, apoptosis was not observed in DCAMKL-1 positive cells within the crypt in over 100 counted crypt cross-sections. In order to confirm this finding, a similar experiment was performed and stained for DCAMKL-1 and TUNEL (a marker for apoptosis). Apoptotic cells within the crypt were identified by TUNEL staining (green), and DCAMKL-1 staining (red) at single cell positions in the intestinal crypt was again observed (FIG. 3B). There was no evidence of apoptosis in DCAMKL-1 expressing cells. Furthermore, radiation-induced DNA damage was observed in the crypt at 6 hours following IR evidenced by the presence of phospho-H2AX positive cells (FIG. 3D, magnified in inset), which was not observed in unirradiated mice (FIG. 3C, magnified in the inset). The DCAMKL-1 positive cell was also positive for nuclear phospho-H2AX, but did not undergo apoptosis at that time (FIG. 3E, magnified in the inset). Indeed, this was not completely unexpected as earlier reports suggest that two important waves of apoptosis exist following IR. The first wave occurs at 4.5-6 hours (p53 dependent), and the second is near 24 hours (p53 independent). The second wave of apoptosis is thought to affect stem cells primarily [Merritt et al., 1994; Radtke et al., 2005]. In order to investigate this further, animals were examined 24 hours after IR, and immunohistochemical analysis for DCAMKL-1 was performed (FIG. 3F). In this figure morphological evidence of apoptosis and immunoreactive DCAMKL-1 staining in the stem cell zone are demonstrated; however, at this time point, there was clear evidence of apoptosis in the DCAMKL-1 positive cell (arrow). Additionally, the appearance of mitotic figures was noted, demonstrating the release of these cells from radiation-induced cell cycle arrest (FIG. 3F denoted as 'M'). The mitotic figures were often DCAMKL-1 immunoreactive, but this staining pattern was not observed in all of the mitotic figures present throughout the intestine. It should be noted that many of the cells with morphologic features consistent with mitosis were on occasion immediately adjacent to cells in the process of apoptosis, and these exhibited striking expression of DCAMKL-1. Consequently, these data suggest that by 24 hours after low dose IR (6 Gy), a few (one per cross section) stem cell/progenitor cells are removed by apoptosis and the potential descendants of these cells are able to divide and, at least transiently, express DCAMKL-1.

Figure 4:
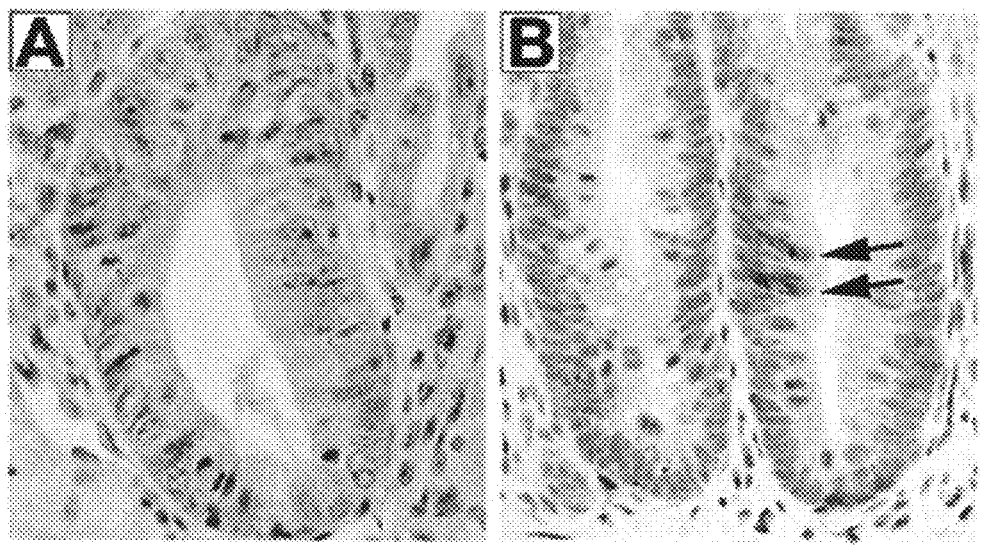

Expression pattern of DCAMKL-1 in regenerative crypts. To determine whether or not DCAMKL-1 is expressed in regenerative crypts following radiation injury, adult mice were exposed to lethal dose (12 Gy) γ-irradiation, and DCAMKL-1 expression was examined in regenerative crypt epithelial cells. 12 Gy was chosen as this dose has been demonstrated to induce crypt stem cell sterilization in a majority of intestinal crypts [Potten et al., 1994]. Regenerative crypts appear 3.5 days following radiation injury and represent the survival of at least one progenitor/stem cell per crypt. DCAMKL-1 staining was not observed in regenerative crypts following 12 Gy (FIG. 4A). These data demonstrate that DCAMKL-1 is not expressed at the protein level during the period of crypt regeneration when proliferation is at its peak. This data is consistent with the original report [Giannakis et al., 2006] and with our findings, failing to demonstrate DCAMKL-1 staining in BrdUrd positive cells (data not shown). On the other hand, it is unclear why this marker is not expressed as every cell in the regenerative crypt is not in a proliferative state. This may represent some form of loss of niche signaling in 3.5 day post-irradiated crypts lacking an intact crypt/villus axis or functional mesenchymal cells. Although it is interesting to speculate, more studies directed towards defining the regulatory mechanisms that control expression of DCAMKL-1 are required. Restoration of DCAMKL-1 expression however, within the crypts was observed 7 days post-irradiation when the morphologic features of the crypts/villus axis are returning to baseline (FIG. 4B), yet the crypts appear elongated with heaping up of nuclei. In several cross-sections DCAMKL-positive cells were not necessarily restricted to lower crypt region.

Figure 5:
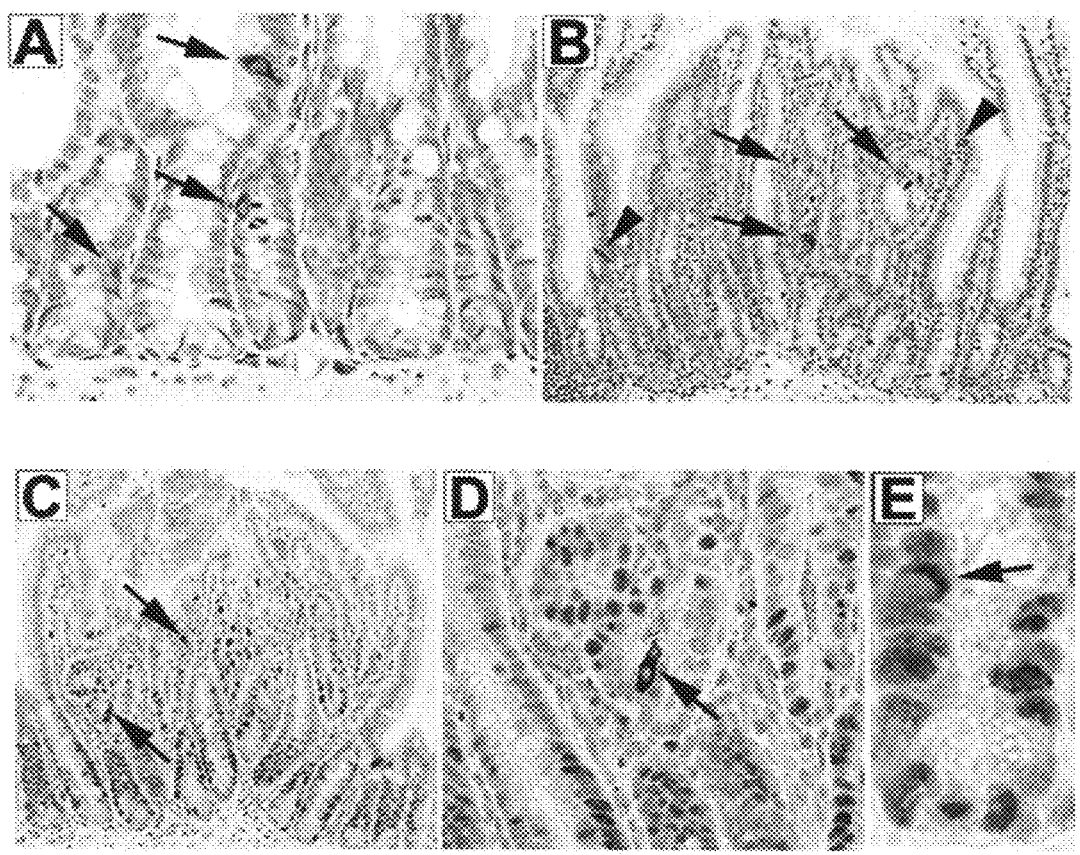

DCAMKL-1 as a putative adenoma stem cell marker. To determine whether DCAMKL-1 could be used to label putative stem cells within tumors, immunohistochemical analysis was employed to identify DCAMKL-1 in the intestines of APC/min mice. These mice have a germline mutation in the APC gene and develop numerous intestinal polyps [Clevers, 2004; Corpet et al., 2005]. APC mutations are one of the earliest genetic alterations in epithelial tumor progression [Clevers, 2006]. Indeed, greater than 60 percent of human colorectal adenomas exhibit a mutation in APC [Powell et al., 1992]. In WT mice classical single cell staining was observed in scattered crypt epithelial cells. However, in APC/min mice, a slightly different expression pattern was observed compared to WT. Although occasional single cell staining in the crypts was observed as before, there was a trend towards increased DCAMKL-1 expression on the villi (FIGS. 5A and 5B) compared to WT mice. This was often particularly evident in villus epithelial tissues adjacent to or surrounding adenomas (FIG. 5B). Note the distinct cytoplasmic staining pattern in the villus epithelium (FIG. 5A arrow head). It is unclear whether this is a function of villus expression of stem cells or a loss of crypt niche restriction in DCAMKL-1 expressing cells. It should be noted that villus epithelial DCAMKL-1 expression was occasionally observed in WT mice as well. Further studies following isolation of these cells are required to fully determine the functional significance of these villus DCAMKL-1 staining cells.

DCAMKL-1 positive cells in adenomas are quiescent. The potential stem cell origin of neoplastic tissues has become increasingly recognized [deLau et al., 2007; Radtke et al., 2005]. Accordingly, changes in the regulation of stem cells could potentially alter the risk of tumorigenesis. Immunohistochemical analysis was used to assess DCAMKL-1 expression patterns in APC/min adenomas. Distinct staining was observed (FIG. 5B), in a minority of cells within the adenoma. Given the limited expression pattern of DCAMKL-1 in adenomas, the inventors wanted to determine whether DCAMKL-1 was expressed in proliferative cells within adenomas. Double staining protocols for both DCAMKL-1 and PCNA (proliferating cell nuclear antigen) were employed in APC/min mice. As expected the majority of the adenomas expressed the proliferation marker PCNA. Indeed, there were very few cells within the adenoma that did not express PCNA. As PCNA staining is primarily nuclear, it was predicted that the cytoplasmic DCAMKL-1 would be identified in proliferating cells if co-staining was present. DCAMKL-1 was expressed in cells within the adenoma that were not proliferating and therefore quiescent (FIG. 5C, magnified in FIG. 5D). This was confirmed in normal crypt epithelial cells in which DCAMKL-1 positive cells were negative for PCNA (FIG. 5E). This is consistent with the original report in FVB/n mice where DCAMKL-1 cells were negative for BrdUrd [Giannakis et al., 2006]; however, this finding within adenomas has not been previously described.

Figure 6:
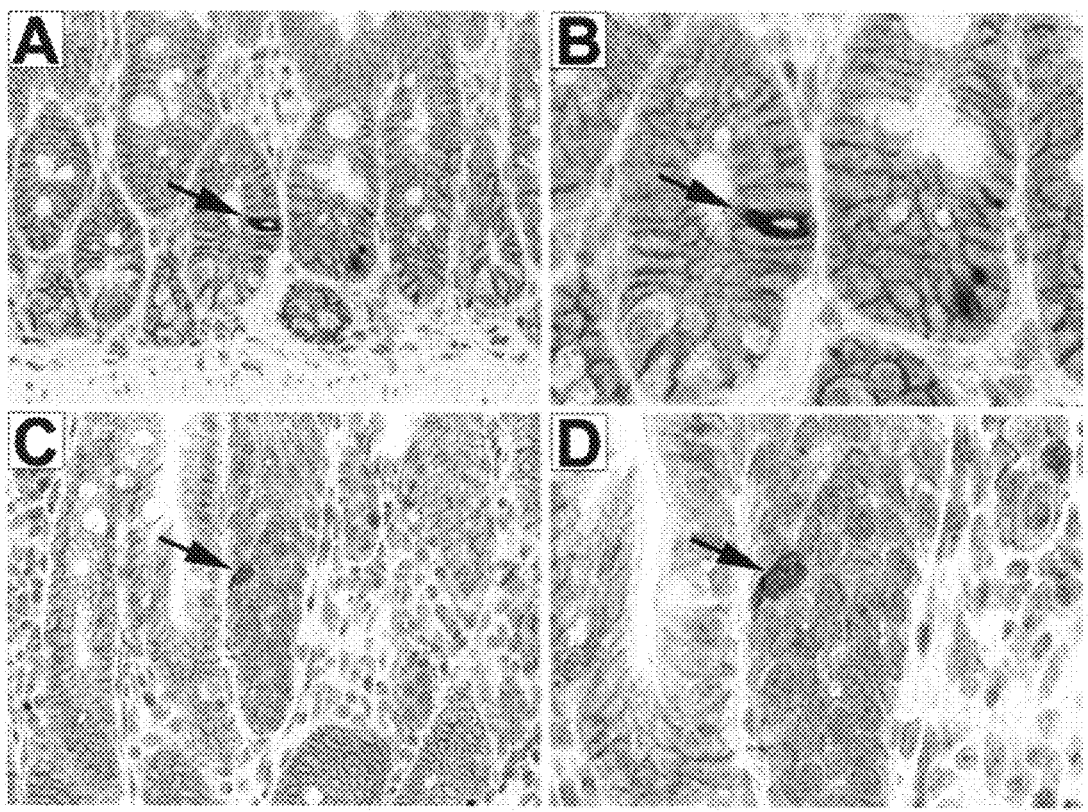

Co-expression of β-catenin and DCAMKL-1 in APC/min tumors. To determine whether nuclear localization of β-catenin could be observed in DCAMKL-1 expressing cells, the inventors sought to identify β-catenin in quiescent cells within adenomas. β-catenin translocation to the nucleus is one of the earliest steps in neoplastic transformation and is readily observed in adenomas of APC/min mice. In FIG. 6, β-catenin and DCAMKL-1 coimmunostaining is demonstrated in normal appearing intestinal crypts in APC/min mice and within a crypt adenoma. In normal appearing crypts, DCAMKL-1 immunoreactive cells exhibit typical membrane β-catenin staining, without any evidence of nuclear translocation (FIG. 6A, magnified in FIG. 6B); however, within the adenoma, nuclear β-catenin is readily identified in the DCAMKL-1 expressing cell (FIG. 6C arrow, magnified in FIG. 6D). These data taken together strongly suggest that the normal epithelial intestinal stem cell and the adenoma stem cell can be distinguished based on nuclear β-catenin and DCAMKL-1 immunostaining. Furthermore, the adenoma stem cell can be distinguished from the proliferative adenoma cells based on PCNA and DCAMKL-1 immunostaining.

Figure 7:
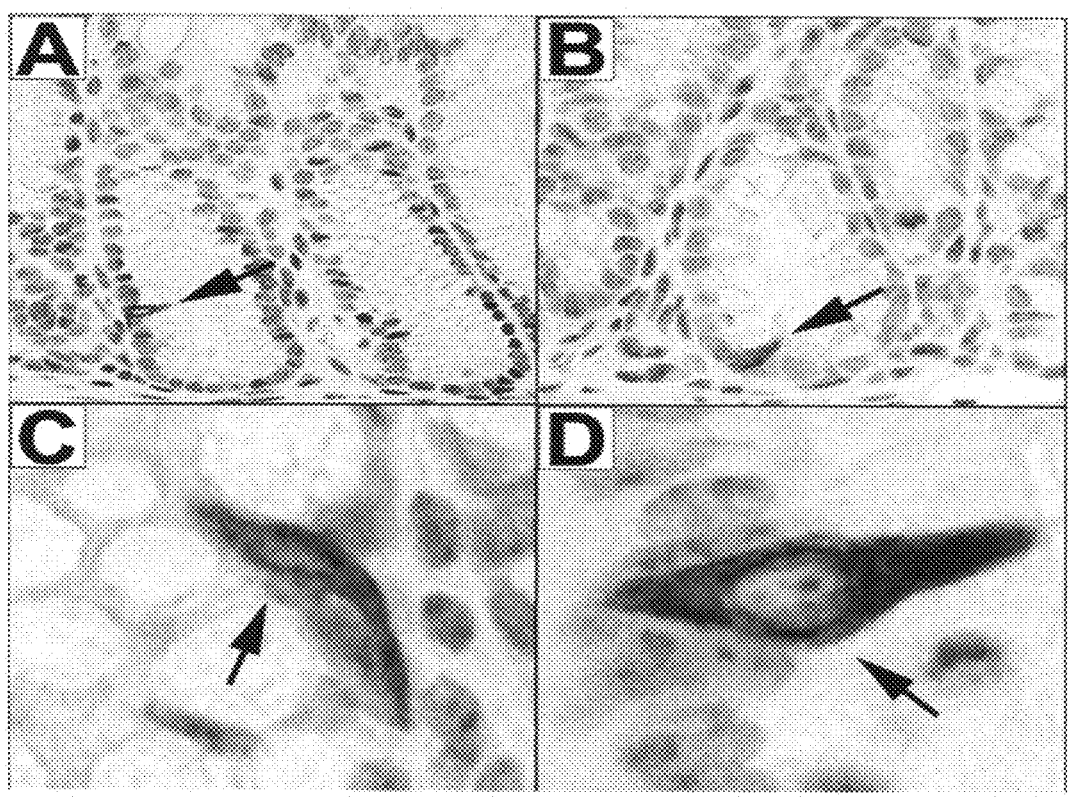

Morphology of DCAMKL-1 expressing cells. Upon closer observation the unique morphologic appearance of the DCAMKL-1 expressing cell resembles that of neural processes observed on gastric D cells [Radford et al., 2006] (FIG. 7A-D). In FIG. 7A, DCAMKL-1 expression was observed in cells in the mid crypt in the proximal colon. In FIG. 7B, an expression was observed at the crypt base in the distal colon. Additionally, higher power views in both colon (FIG. 7C) and distal jejunum (FIG. 7D) clearly illustrate the unique morphologic staining pattern resembling axonal like processes.

Discussion of Example 1

Figure 1:
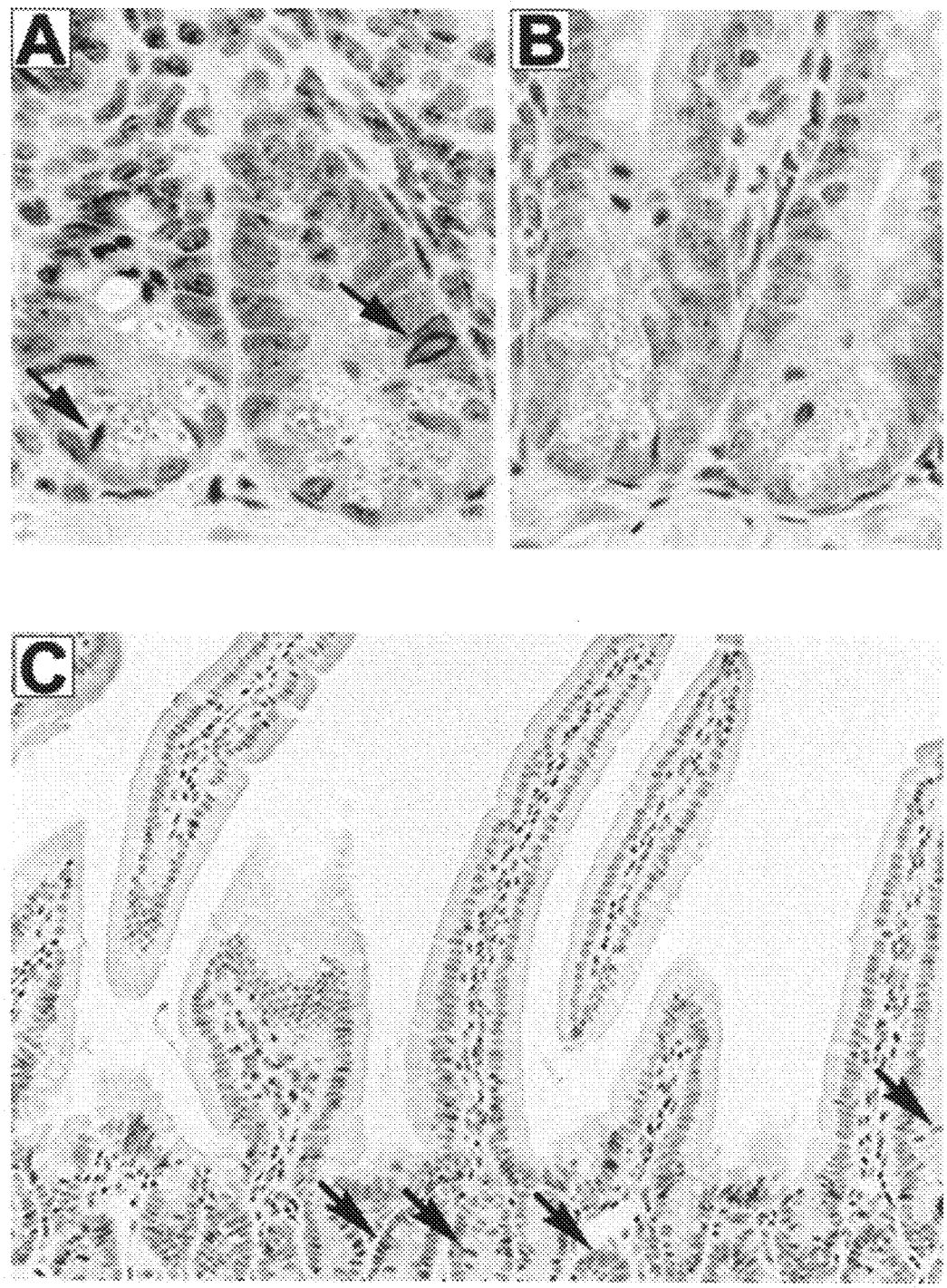

Typically, one crypt with definitive DCAMKL-1 staining was observed per 6 crypts in a typical intestinal cross-section near cell position of 4 in the crypt. Presumably, this is due to the 3-dimensional nature of the crypt and the low probability that every cross-section will contain a stem cell. Nevertheless, DCAMKL-1 immunoreactivity was consistently observed in the stem cell zone as previously noted (FIG. 1). The response to acute radiation injury is the most extensively characterized model system for studying injury repair in the rodent gastrointestinal tract. The actively proliferating cell population in the intestinal crypt rapidly undergoes apoptotic cell death following sublethal doses of IR, (<8Gy) [Ishizuka et al., 2003]. Because epithelial cells at the lower one third of the small intestinal crypts are the first to undergo apoptosis following low-dose IR (1 Gy), it is postulated that these "true" or "ultimate" stem cells prefer to undergo apoptosis rather than repair even comparatively minor damage to their DNA [Potten et al., 2002]. This trait may serve to reduce the risk of propagating a mutated clone within the crypt. If all the so-called "ultimate stem cells" [Potten et al., 2002] are destroyed, then their more radio-resistant daughter cells will assume stem cell functions and maintain the crypt; however, the molecular mechanisms that regulate this transfer of clonogenic capacity are poorly understood. In this Example, it has been demonstrated that cells positive for DCAMKL-1 underwent DNA damage along with other cells in the crypt, but did not undergo apoptosis. Whereas 24 hours following IR, the putative stem cell or cells positive for DCAMKL-1 did undergo apoptosis. Following 12 Gy IR, the DCAMKL-1 reactivity is lost in the regenerative crypts 3.5 days following IR. DCAMKL-1 expression was restored at day 7 post-irradiation when the morphologic features of the crypts/villus axis are returning to baseline. These data support the hypothesis that daughter cells are capable of taking on stem cell characteristics in response to radiation-induced deletion of the "ultimate stem cell" and also illustrates that this process occurs at some time beyond 6 hours and prior to 24 hours after low dose radiation injury. These data may potentially explain why doses of IR<8 Gy do not result in crypt sterilization of stem cells and, as a result, have little effect on clonogenic survival [Houchen et al., 2000].

This Example reports the identification of a novel intestinal stem cell marker that can be employed to test the effects of DNA damaging agents, chemotherapeutic agents and radiation injury on stem cell deletion both directly and in real time. The data presented here also support assessment of radiation-induced apoptosis of intestinal stem cells 24 hours after IR as opposed to 6 hours in intestinal cross sections. The demonstration of a more variable expression pattern of DCAMKL-1 in the normal epithelium of APC/min mice compared to WT mice suggests that APC/min mice may exhibit different mechanisms of stem cell niche regulation, particularly in the regions adjacent to adenoma. The small percentage of quiescent DCAMKL-1 expressing cells within a particular adenoma suggests that they may be the origin of the more proliferative neoplastic cells, but it remains unclear whether these cells by themselves have tumorigenic potential either outside of the adenoma or outside of the crypt niche (villi). In the normal appearing crypts of APC/min mice, β-catenin was co-expressed in the cytoplasm along with DCAMKL-1, whereas in adenomas, DCAMKL-1 positive cells demonstrated nuclear localization of β-catenin. This finding potentially illustrates a fundamental difference between the normal and adenoma stem cell. Isolating these cells and injecting them into nude mice xenograft models are essential in addressing the tumorigenic potential of these cells.

Example 2

Pancreatic adenocarcinoma has the worst prognosis of any major malignancy with a 3% 5-year survival [Hoyer et al., 2006]. Major obstacles in treating pancreatic cancer include extensive local tumor invasion and early metastasis. There is increasing evidence that a small subset of cells termed "cancer stem cells" (CSCs) are capable of initiating and sustaining tumor growth in transplantation assays [Diehn et al., 2006]. CSCs share unique properties with normal adult stem cells, including the ability to self-renew and differentiate. CSCs are often refractory to current standard chemotherapeutic agents and radiation therapies, as they are designed to eradicate actively cycling cells, not slowly cycling cancer stem cells. Thus, novel therapies that specifically target the cancer stem cell population, either alone or in conjunction with current strategies may be more effective in obliterating solid tumors.

The existence of CSCs was first demonstrated in acute myelogenous leukemia [Bonnet et al., 1997] and subsequently verified in breast [Al-Hajj et al., 2003], pancreatic [Li et al., 2007] and brain tumors [Singh et al., 2004; Singh et al., 2003; Singh et al., 2004A]. The CD133$^+$ subpopulations from brain tumors could initiate clonally derived neurospheres in vitro showing self-renewal, differentiation, and proliferative characteristics similar to normal brain stem cells [Singh et al., 2004; Singh et al., 2003; Singh et al., 2004A]. Furthermore, transplantation of CD133$^+$ but not CD133$^-$ cells into NOD/SCID mice was sufficient to induce tumor growth in vivo. In a recent study, primary human pancreatic adenocarcinomas were implanted in immunocompromised mice to assess the ability of specific cell surface markers to identify a subpopulation of pancreatic cancer cells with enhanced tumorigenic potential. A subpopulation of CD44$^+$CD24$^+$ESA$^+$ cells was identified as putative pancreatic cancer stem cells [Li et al., 2007].

Tumor cell heterogeneity present in most solid tumors creates an enormous challenge for cancer eradication. Current strategies for inducing cell death generally target only the most rapidly proliferating cells within a tumor. Indeed radiation therapy specifically targets proliferating cells which are more sensitive to ionizing radiation [Houchen et al., 2000A; Riehl et al., 2000; Tessner et al., 1998; Cohn et al., 1997]; however, it is clear that effective tumor-eradication strategies must address the potential survival mechanisms unique to each particular cell type within the malignant population (i.e., quiescent stem cells) [Li et al., 2007]. This may explain why standard chemo/radio therapy is effective in causing tumor shrinkage but often fails to prevent tumor recurrence, due to the surviving cancer stem cell's ability to regenerate the tumor even after chemotherapeutic insult.

Characterization of stem cells from the hematopoietic system, neural stem cells from the central nervous system and neural crest stem cells have emphasized the importance of specific cell surface antigens that permit the isolation of stem cells by FACS [Tamaki et al., 2002; Niemeyer et al., 2001]. A candidate pancreatic stem cell, characterized by its expression of the neural stem cell marker nestin and lack of established islet and ductal cell markers, has been described [Abraham et al., 2004; Lechner et al., 2002; Zulewski et al., 2001]. Furthermore, the basic helix-loop-helix transcription factor neurogenin 3 (NGN3) controls endocrine cell fate specification in uncommitted pancreatic progenitor cells. In the pancreas, NGN3$^+$ cells co-express neither insulin nor glucagon, suggesting that NGN3 marks early precursors of pancreatic endocrine cells. Moreover, NGN3-deficient mice do not develop islet cells and are diabetic. These data taken together suggest that NGN3 and nestin are critical components of the pancreatic stem/progenitor cell compartment. A convincing recent study demonstrated that the adult mouse pancreas contains islet cell progenitors and that expansion of the β cell mass following pancreatic duct ligation resulted in ductal NGN3 gene expression and the ensuing differentiation of endogenous progenitor cells [Xu et al., 2008]. These data suggest that functional islet progenitor cells can be induced in pancreatic ducts following injury.

Example 1 demonstrates that DCAMKL-1, a microtubule-associated kinase expressed in postmitotic neurons, is an intestinal stem cell marker [May et al., 2008]. In this Example, it is demonstrated that DCAMKL-1 is also expressed in pancreatic islet epithelial cells with a distribution similar to the putative pancreatic stem cell markers NGN3 and nestin. Furthermore, DCAMKL-1 is expressed in the main pancreatic ductal epithelial cells in rodents, and a subset of cells in human pancreatic tumors. Immunoreactive 14-3-3 σ, which is increased in pancreatic cancer [Guweidhi et al., 2004], has been found in the cytoplasm and rarely in the nucleus of tumor epithelial cells in human pancreatic cancer patients. Moreover, co-expression of DCAMKL-1 and 14-3-3 σ was also observed in tumors. Additionally DCAMKL-1 staining was observed in the surface epithelium of pancreatic intraepithelial neoplasia (PanIN) type lesions (a marker of pancreatic adenocarcinoma) and the intervening stroma in human pancreatic adenocarcinoma, which co-localized with the mesenchymal marker vimentin. In the Pdx48$^{Cre}$-activated KRAS$^{G12D}$ [Hingorani et al., 2003; Jackson et al., 2001] pancreatic cancer mouse model there was a marked increase in ductal expression and a unique expansion of islet DCAMKL-1 that correlated with progressive neoplastic changes. These data taken together, demonstrate that DCAMKL-1 is a novel pancreatic stem cell marker expressed in the pancreatic duct and in islets as well as a marker of pancreatic cancer stem cells. Furthermore, this Example demonstrates the isolation of DCAMKL-1 expressing cells by FACS, which formed spheroid-like structures in suspension culture. When injected subcutaneously into flanks of nude mice, nodules formed and contained cells expressing markers of early pancreatic development (PDX-1), glandular epithelium (cytokeratin 14), and islets (somatostatin and secretin). These data taken together identify DCAMKL-1 as a novel pancreatic ductal and islet stem/progenitor cell marker that can be employed as a target for pancreatic cancer tumor eradication. DCAMKL-1 also represents a novel marker for studying the mechanisms that regulate pancreatic and/or islet regeneration.

Materials and Methods for Example 2

Experimental animals. 6-8 weeks old C57BL/6, athymic nude mice (NCr-nu) (NCI-Frederick) and Pdx48$^{Cre}$-activated KRASG12D (obtained from Dr. Rao) were used for the experiments. Mice were housed under controlled conditions, including a 12 h light/dark cycle, with ad libitum access to diet and water. All animal experiments were performed in accordance with the University's Institutional Review Board.

Tissue procurement. The human pancreatic adenocarcinoma tissue samples were derived from patients undergoing a surgical resection of the pancreas at the University of Oklahoma Health Sciences Center. The collection of samples conformed to the policies and practices of the University's Institutional Review Board (protocol number 04586).

Immunohistochemistry. Heat Induced Epitope Retrieval was performed on formalin-fixed paraffin-embedded sections utilizing a pressurized Decloaking Chamber (Biocare Medical) in citrate buffer (pH 6.0) at 99° C. for 18 min. (a) Brightfield: Slides were incubated in 3% hydrogen peroxide, then normal serum and BSA at room temperature for 20 min. After incubation with primary antibody [DCAMKL-1, insulin, glucagon, somatostatin, PDX-1 (ABCAM), 14-3-3 σ (IBL), NGN3, nestin, vimentin, cytokeratin-14 and secretin (Santa Cruz)] the slides were incubated in polymer-HRP secondary (DAKO). Slides were developed with Diaminobenzidine (Sigma). Tyramine signal amplification for NGN3 in adult mouse tissues was performed as per manufacturer's instructions (Invitrogen) (b) Fluorescence: Slides were incubated in normal serum and BSA at room temperature for 20 min. After incubation with primary antibody, slides were incubated in appropriate Alexa Fluor® conjugated secondary [488 (green) and 568 (red)].

Microscopic examination. Slides were examined utilizing the Nikon 80i microscope and DXM1200C camera for brightfield. Fluorescent images were taken with PlanFluoro objectives, utilizing CoolSnap ES2 camera (Photometrics). Images were captured utilizing NIS-Elements software (Nikon).

Stem cell isolation from mouse pancreas. DCAMKL-1+ stem cells were isolated and propagated from mouse pancreas according to the procedures developed in neural [Singh et al., 2004; Singh et al., 2003; Singh et al., 2004A] and breast stem cell biology [Dontu et al., 2003]. The pancreas and associated duct were rapidly dissected and perfused with 3 ml of cold HBSS containing 1 mg/ml collagenase and 1 mg/ml BSA (Cellgro). The pancreatic tissues were minced and incubated in HBSS for 13 min at 37° C. Digestion was stopped with cold HBSS (Cellgro) containing 10% serum. The solution was shaken by hand for 1 min, washed 3 times with serum free HBSS and filtered through 400 mM mesh (Spectrum). The cells obtained were incubated with trypsin (Cellgro) at 37° C., pipetted to create a single cell suspension and subjected to FACS based on cell surface expression of DCAMKL-1.

FACS sorting. The single cell suspension was incubated with 1:100 dilution of Alexa Fluor® 568 conjugated DCAMKL-1 antibody targeting the C-terminal extracellular domain for 25 min and washed twice with HBSS containing 10% serum. The cells were sorted using Influx-V cell sorter (Cytopeia) and collected cells were grown in tissue culture media: DMEM (Cellgro) containing EGF (25 ng/ml), bFGF (20 ng/ml) and Insulin (5 ng/ml) (Sigma) without serum on non-treated or ultra-low adherent plates (BD Biosciences) in a suspension culture.

Isotransplantation assay. Collected cells expressing DCAMKL-1 were allowed to form spheroids in suspension culture for 21 days. Spheroids were disassociated, suspended in matrigel and injected subcutaneously into the flanks of athymic nude mice (NCr-nu) (NCI-Frederick) housed in specific pathogen-free conditions. Animals were sacrificed, nodules excised, fixed in 10% buffered formalin and subjected to immunohistochemical analysis.

Results of Example 2

Figure 8:
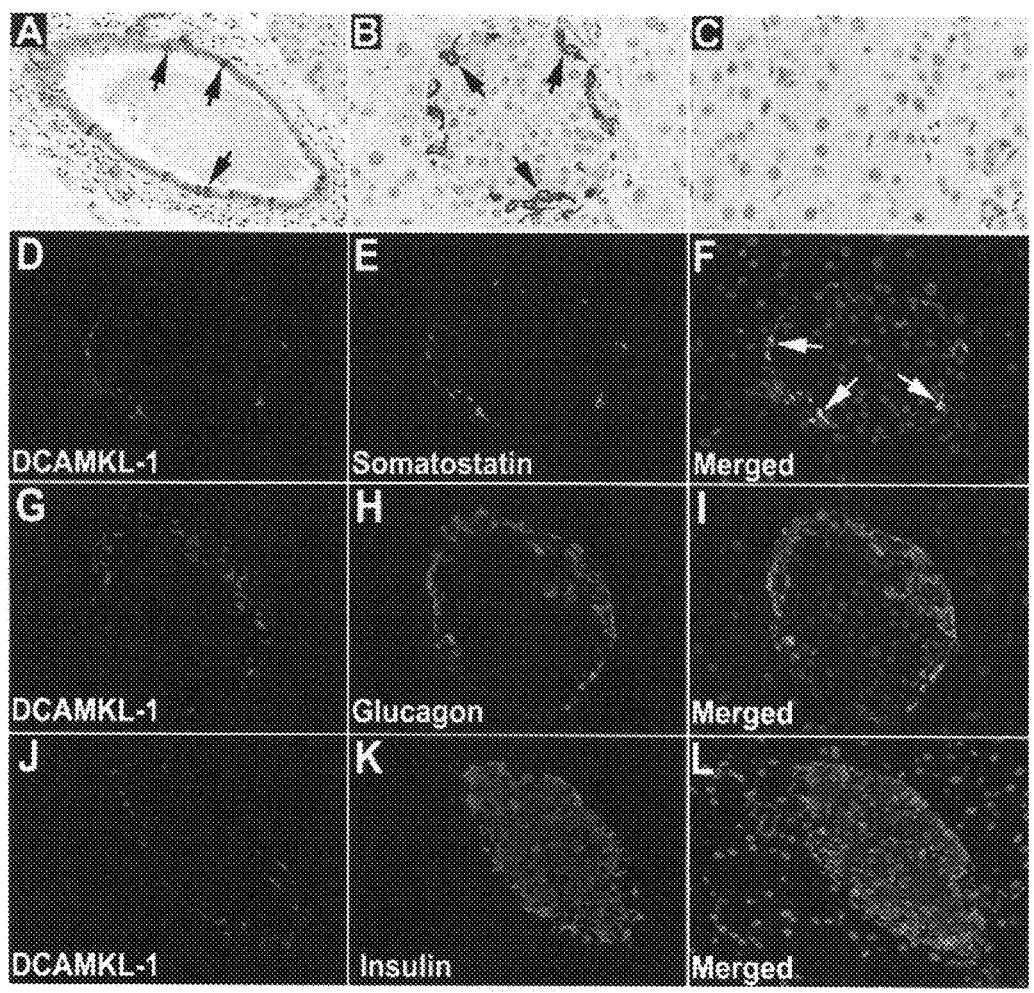

Pancreatic DCAMKL-1 expression. DCAMKL-1 is expressed in the main pancreatic duct (FIG. 8A left) and on the periphery of pancreatic islets (FIG. 8A middle). There was no detectable DCAMKL-1 expression within acinar cells in uninjured mice (FIG. 8A right). In order to determine the specific islet cell sub-type, co-expression of the endocrine markers somatostatin (d-cell), glucagon (a-cell) and insulin (b-cell) was evaluated. It was found that both DCAMKL-1 (FIG. 8B left) and somatostatin (FIG. 8B middle) were expressed in the islet periphery. Merged images revealed co-staining of DCAMKL-1 with somatostatin (FIG. 8B right). Glucagon was also found in the periphery of the islet (FIG. 8C middle) but did not co-localize with DCAMKL-1 (FIG. 8C right). Insulin expressing cells were observed throughout the islet (FIG. 8D middle), but no co-immunostaining with DCAMKL-1 was observed (FIG. 8D right). Thus DCAMKL-1 expressing cells do not express the two major endocrine cell markers (insulin and glucagon) but do co-localize with somatostatin expressing cells.

Figure 9:
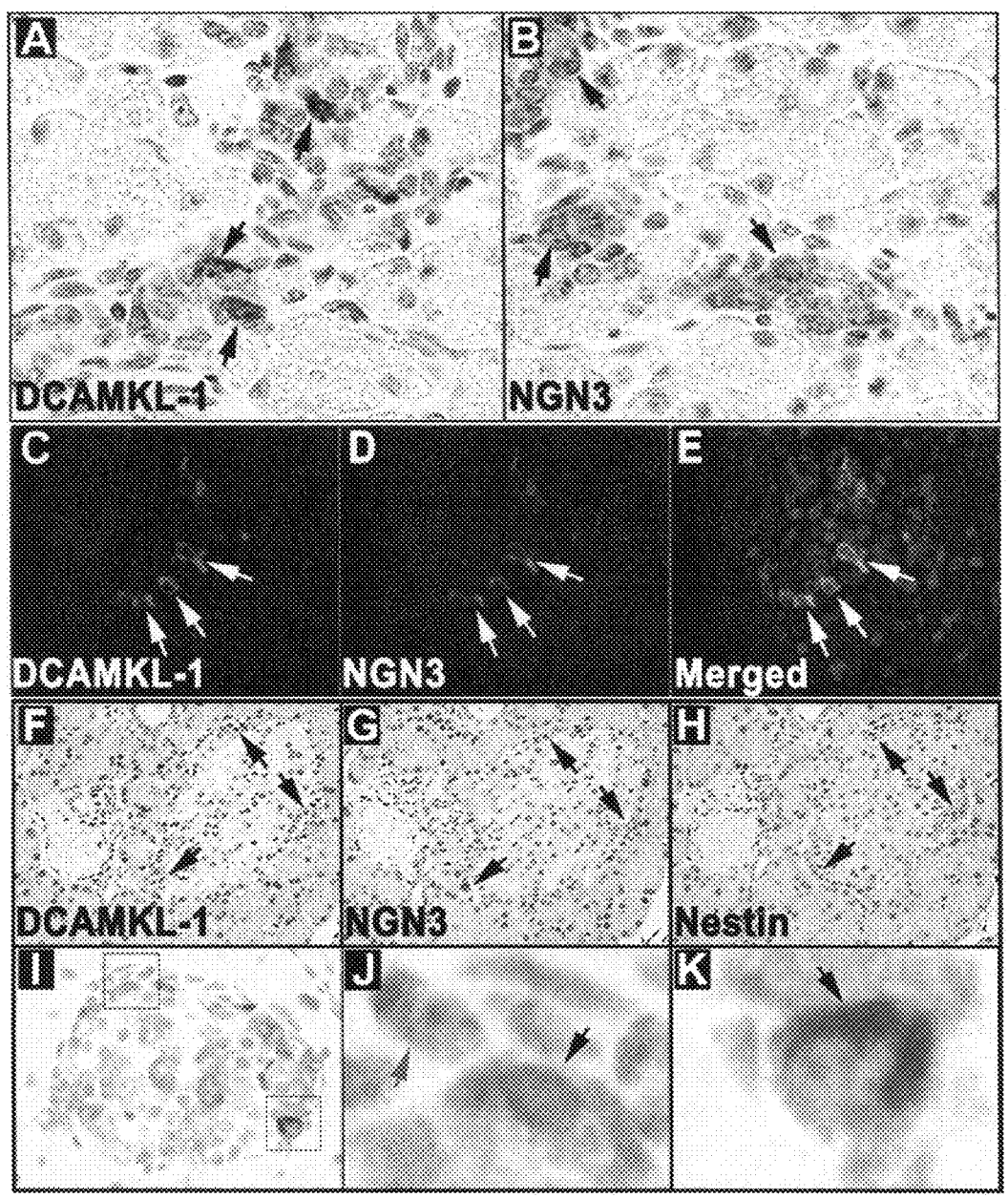

Pancreatic stem cell markers. The basic helix-loop-helix transcription factor NGN3 controls endocrine cell fate specification. All the major islet cell types, including insulin-producing b-cells, are derived from NGN3-positive endocrine progenitor cells [Johansson et al., 2007]. It is well known that NGN3 protein expression diminishes as mice reach adulthood [Schwitzgebel et al., 2000; Jensen et al., 2000]. Immunohistochemical analysis was employed in order to determine the cell specific expression patterns of DCAMKL-1 in newborn mice, and with reference to NGN3 expression [Gu et al., 2002]. Distinct expression of DCAMKL-1 (FIG. 9A left) and NGN3 (FIG. 9A right) was observed in early islet formations. Immunofluorescence staining confirmed the presence of DCAMKL-1 (FIG. 9B left) and NGN3 (FIG. 9B middle) with merged images revealing distinct co-localization within these developing tissues (FIG. 9B right).

To confirm these findings in adult uninjured mice, immunohistochemical staining was employed on serial tissue sections. Common immunolocalized staining was observed for DCAMKL-1 (FIG. 9C left), NGN3 (FIG. 9C middle) and the pancreatic stem cell marker candidate nestin (FIG. 9C right) in all three sections. To further investigate co-localization of DCAMKL-1 and nestin expressing cells, doublelabeled immunoperoxidase staining was employed. Both distinct DCAMKL-1 and nestin expressing cells were observed (FIG. 9D left and middle), as well as co-localization within the pancreatic islet periphery (FIG. 9D right). These data demonstrate that DCAMKL-1 marks pancreatic islet stem/progenitor cells, based on positional evidence, and co-expression with established markers of pancreatic stem/progenitor cells.

Figure 10:
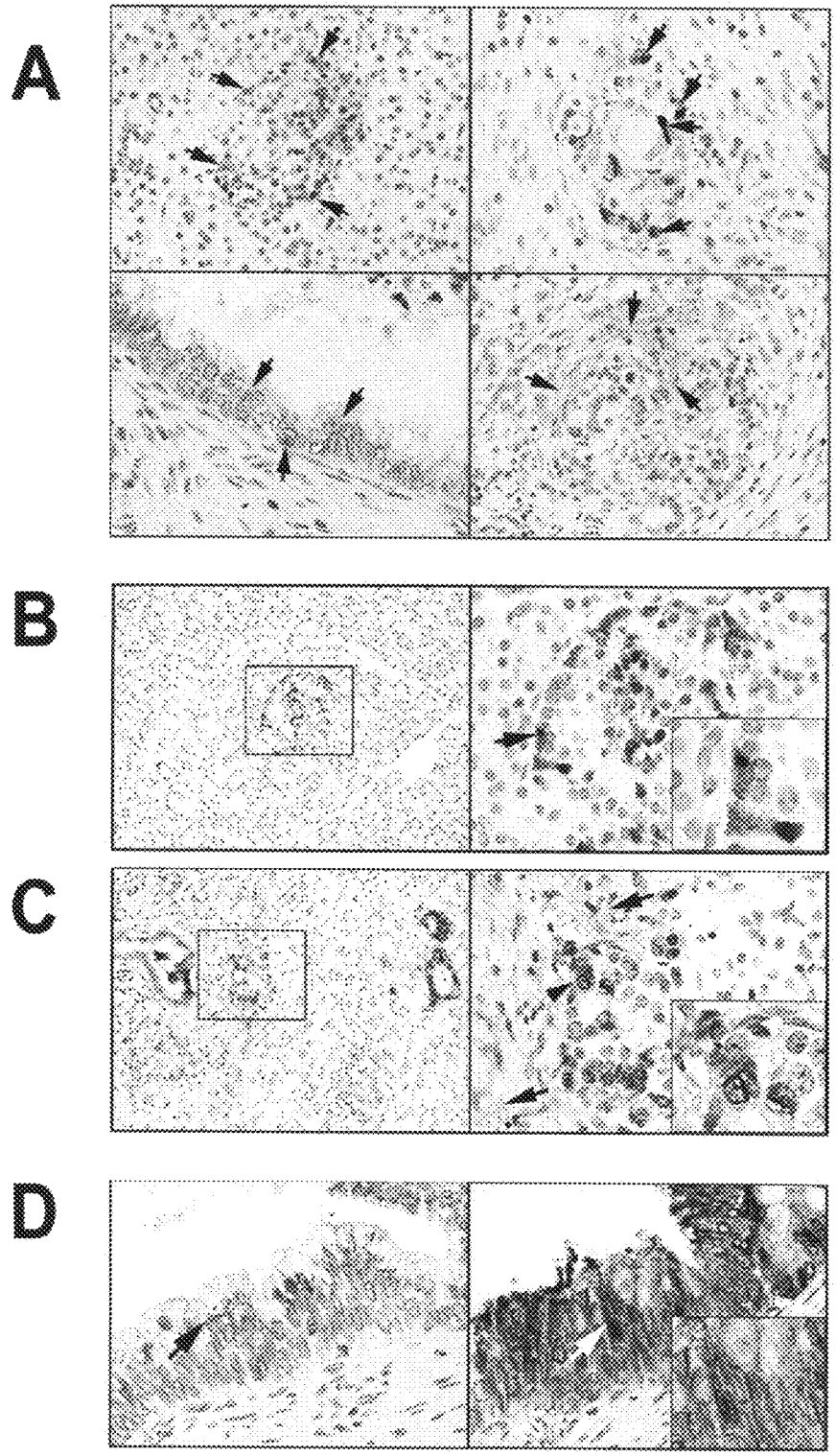

DCAMKL-1 expression in human pancreatic cancer. Next, DCAMKL-1 expression in human pancreatic adenocarcinoma was examined. Samples were obtained from patients undergoing surgical resection of pancreatic cancer provided by Dr. Russell Postier. Tumors demonstrated strong DCAMKL-1 expression. However within the histologically normal appearing resection specimen, DCAMKL-1 was observed within islets but not in the intervening stromal cells or ducts (FIG. 10A top left). Within a neoplastic focus of the tumor resection specimen however, intense spindle-shaped cytoplasmic staining of DCAMKL-1 is evident (FIG. 10A top right). DCAMKL-1 expression in ductal epithelial cells within the tumor (FIG. 10A bottom left) and in intervening stromal elements is also observed (FIG. 10A bottom right).

14-3-3 σ expression in pancreatic cancer. Previously, using DNA array technology, several groups have demonstrated increased 14-3-3 σ mRNA expression in pancreatic ductal adenocarcinoma compared to normal pancreas [Guweidhi et al., 2004]. Similarly, 14-3-3 σ protein nuclear localization has been described in pancreatic cancer [Logsdon et al., 2003]. In normal appearing pancreatic tissue of patients undergoing surgical resection, cytoplasmic staining was observed for 14-3-3 σ and DCAMKL-1 at the islet periphery, albeit in distinctly separate cells. No ducts expressing 14-3-3 σ were observed in that particular specimen (FIG. 10B left and right). Next, immunostaining was performed on a primary tumor specimen obtained from another patient with pancreatic ductal adenocarcinoma. While strong cytoplasmic expression of 14-3-3 σ (a marker of advanced PanIN lesions) was found in ductal epithelial cells, cells with nuclear localized 14-3-3 σ expression were also observed within tumor islet formations. Moreover, some of these nuclear 14-3-3 σ expressing cells also co-expressed DCAMKL-1 (FIG. 10C left and right) suggesting that nuclear translocation of 14-3-3 σ occurs in putative pancreatic cancer stem cells. Expression of DCAMKL-1 was also found in PanIN type lesions (FIG. 10D left). Additionally strong cytoplasmic 14-3-3 σ and DCAMKL-1 co-staining was observed within the lesions (FIG. 10D right). These data strongly support a role for 14-3-3 σ and DCAMKL-1 in the progression of pancreatic cancer and as a putative marker of pancreatic CSCs.

Figure 11:
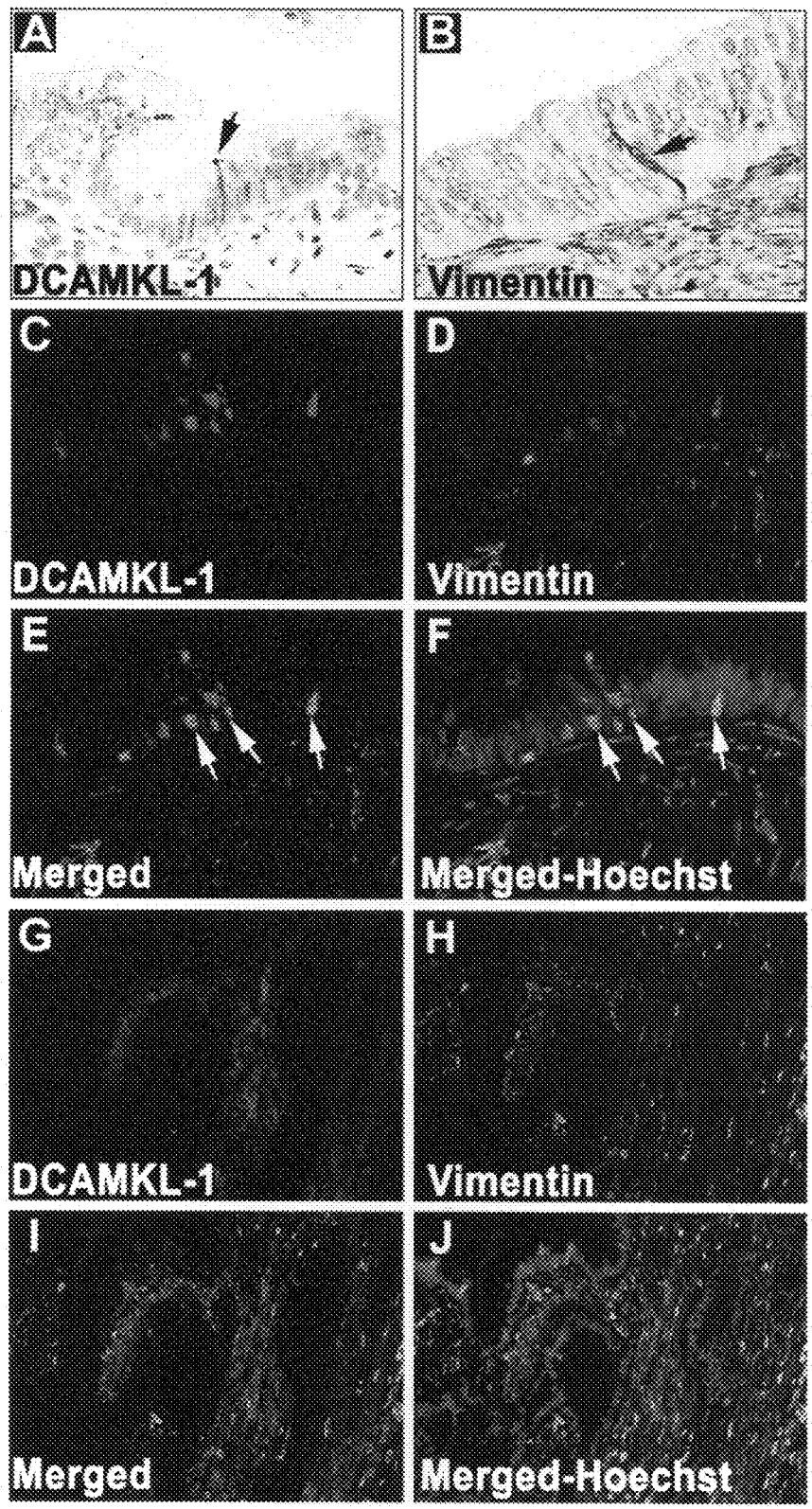
Figure 12:
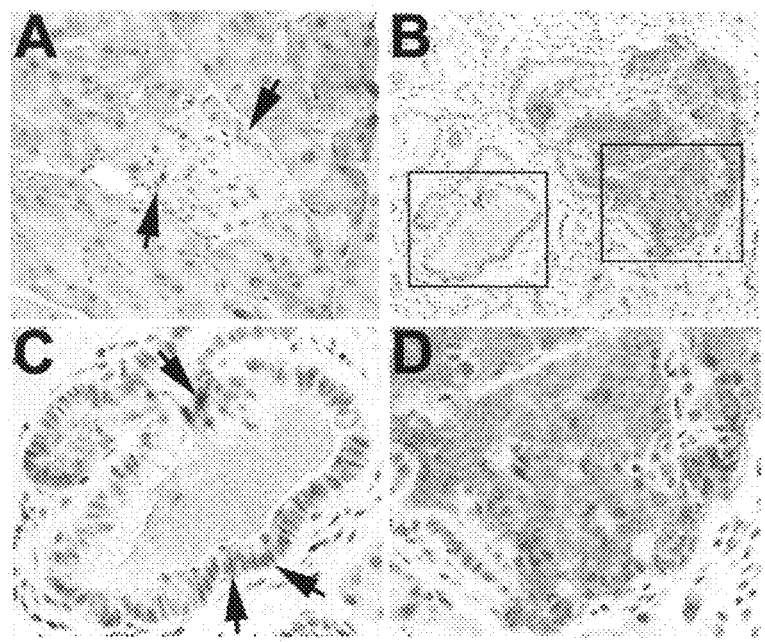

DCAMKL-1 expression in the stroma of human pancreatic adenocarcinoma tissue. Initially, DCAMKL-1+ staining was observed in elongated cells in the surface epithelium of PanIN lesions (FIG. 11A left). Further characterization of these cells by vimentin (a marker of mesenchymal lineage) immunostaining demonstrated cells that were morphologically similar to DCAMKL-1 expressing cells (FIG. 11A right). When double-labeled immunofluorescence was performed, coexpression of DCAMKL-1 and vimentin within the PanIN lesion was observed (FIG. 11B). Strong fibrillar DCAMKL-1 expression was also seen in the stromal/mesenchymal compartment of human pancreatic adenocarcinoma tissue and confirmed by vimentin co-immunostaining (FIG. 11C). These data taken together demonstrate a potential role of DCAMKL-1 in epithelial mesenchymal transition (EMT) [Turley et al., 2008].

Mouse pancreatic cancer model. The Pdx48$^{Cre}$-activated KRAS$^{G12D}$ is a well established mouse model of pancreatic cancer [Hingorani et al., 2003; Jackson et al., 2001]. These mice develop PanIN lesions (similar to humans) and pancreatic cancer after 10 weeks. Furthermore, these mice develop cancer metastasis by 32 weeks [Jackson et al., 2001; Hingorani et al., 2003]. Pancreatic tissues from 5-month-old Pdx48$^{Cre}$-activated KRAS$^{G12D}$ and their wild-type (WT) littermates were immunostained for DCAMKL-1. A marked increase in ductal expression and a unique expansion of islet DCAMKL-1 was found in the Pdx48$^{Cre}$-activated KRAS$^{G12D}$ pancreatic cancer mouse model that correlated with progressive neoplastic changes (FIG. 12A-D). These data demonstrate that DCAMKL-1 upregulation following mutant KRAS mediated tumorigenesis may represent a marker of neoplastic transformation.

Figure 13:
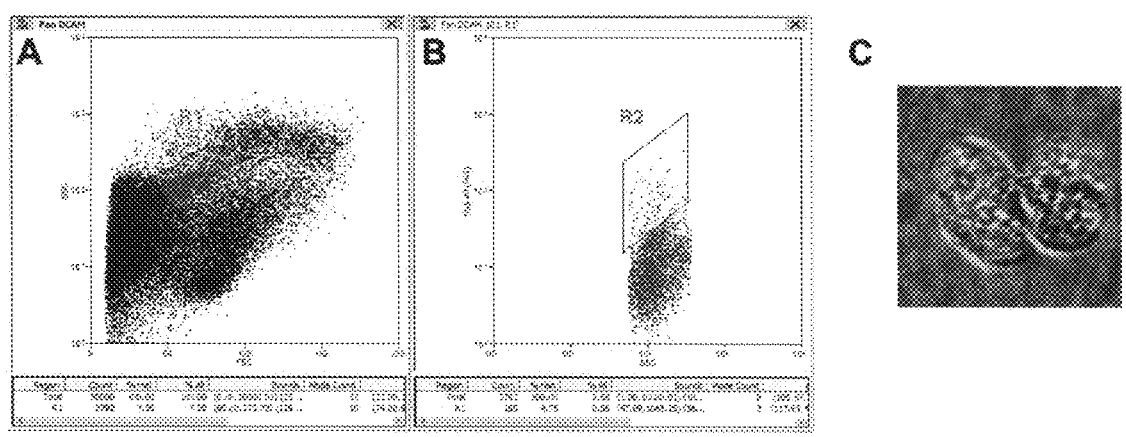
Figure 14:
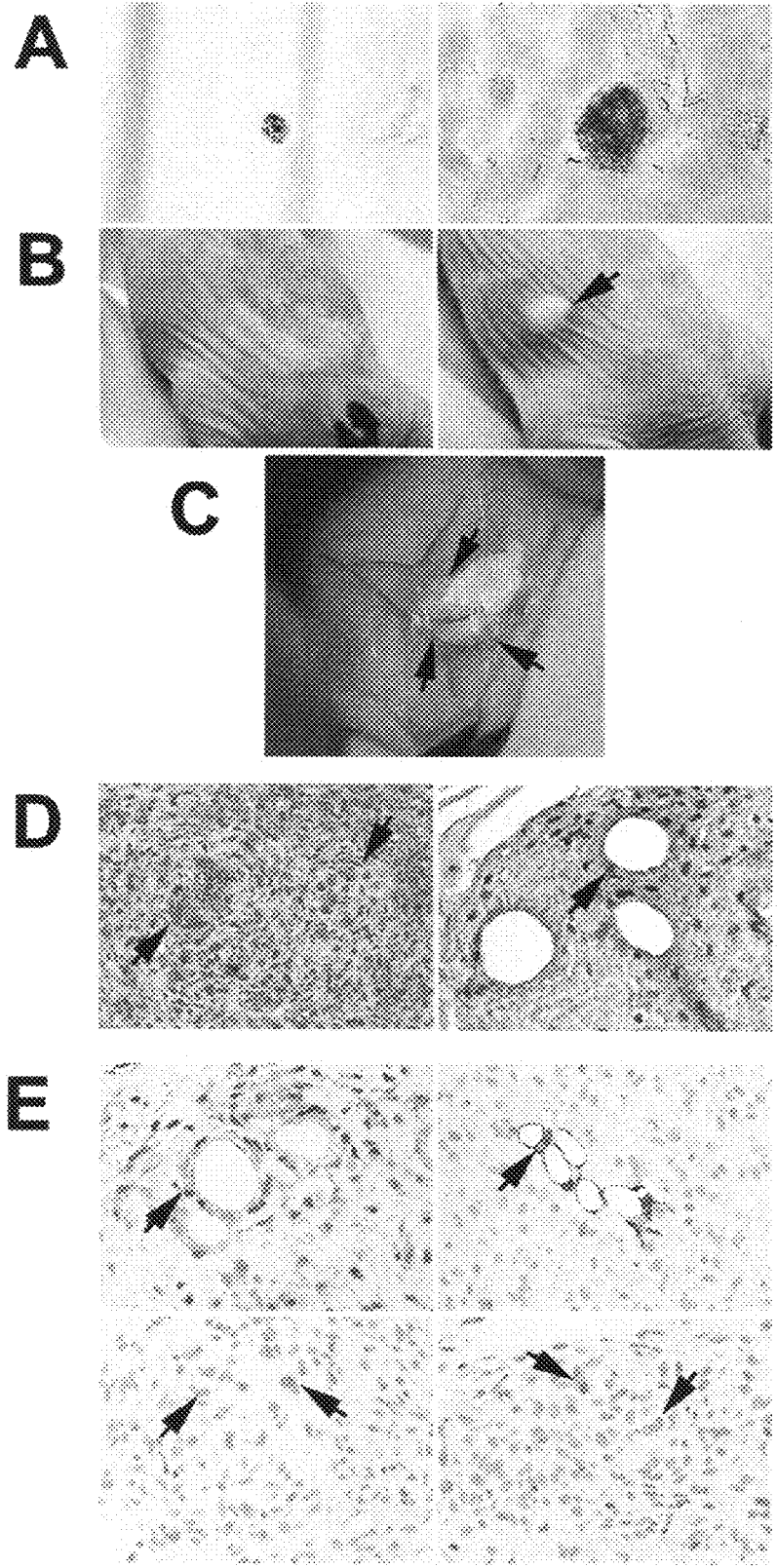

Isolation and propagation of pancreatic stem/progenitor cells. Stem cells within a tissue are capable of self-renewal and differentiation. Dontu et al., [Dontu et al., 2003] isolated human mammary stem/progenitor cells from normal breast tissues. When grown in ultra low attachment plates, they formed spheroid structures termed "mammospheres". To test the hypothesis that there is a small subpopulation of distinct stem/progenitor cells within a normal uninjured rodent pancreas, the mouse pancreas was digested with ultra pure collagenase IV, and FACS based cell sorting for DCAMKL-1 was performed. On average, approximately 0.4% of total cells were sorted using this method (FIG. 13). Three weeks after sorting, the formation of spheroids was observed in growth factor supplemented serum free media [Dontu et al., 2003] (FIG. 14A left—day 0 and 14A right—day 21). Spheroids were separated, suspended in matrigel, and injected subcutaneously into the flanks of athymic nude mice. After four weeks, nodular growth was noted at the site of injection compared to the matrigel injected control (FIG. 14B left—matrigel alone and 6B right—DCAMKL-1 spheroid and matrigel injected). Interestingly, tangrey soft tissue outgrowth was noted that extended beyond the original injection site, which appeared to show new blood vessel formation (FIG. 14C).

DCAMKL-1 sorted spheroids induce pancreatic epithelial expression in the flanks of nude mice. Histological analysis of the excised nodules revealed single cells with oval nuclei and large nucleoli, which appeared to be epithelial in nature, as well as islet-like structures (FIG. 14D). The glandular epithelial origin of these cells was confirmed by cytokeratin-14 immunoreactivity (FIG. 14E top left) [Moll et al., 2008; Purkis et al., 1990] and PDX-1, marker of early pancreatic development (FIG. 14F top right). Additionally, many of the cells within the islet structures expressed secretin [Pollack et al., 1990] (FIG. 14E bottom left) and somatostatin (FIG. 14E bottom right). These data taken together demonstrate that DCAMKL-1 expressing cells isolated from the pancreas of normal uninjured mice by FACS and utilized in isotransplantation assays, are in fact stem/progenitor cells.

Discussion of Example 2

Solid tumors are histologically heterogeneous and include tumor cells, stroma, inflammatory infiltrates, and vascular structures. In recent years, the CSC model of tumorigenesis has received increasing attention [Tang et al., 2007]. This model suggests that tumors are initiated and maintained by a minority subpopulation of cells that have the capacity to self-renew and to generate the more differentiated progeny making up the bulk of a tumor. The CSCs, tumorigenic cancer cells, can give rise to new tumors when transplanted into immunodeficient animals [Diehn et al., 2006].

The existence of CSCs has profound implications for cancer biology and therapy due to the likelihood that eradication of CSCs is the critical determinant in achieving cure. Furthermore, CSCs may be particularly resistant to chemotherapy and radiation therapy. A recent report [Phillips et al., 2006] demonstrated that breast cancer-initiating cells were radioresistant when compared with breast cancer cells that were incapable of initiating tumors. Similarly, another report [Bao et al., 2006; Bao et al., 2006A] suggested that glioblastoma stem cells are radioresistant and may, therefore, contribute to treatment failures.

Figure 15:
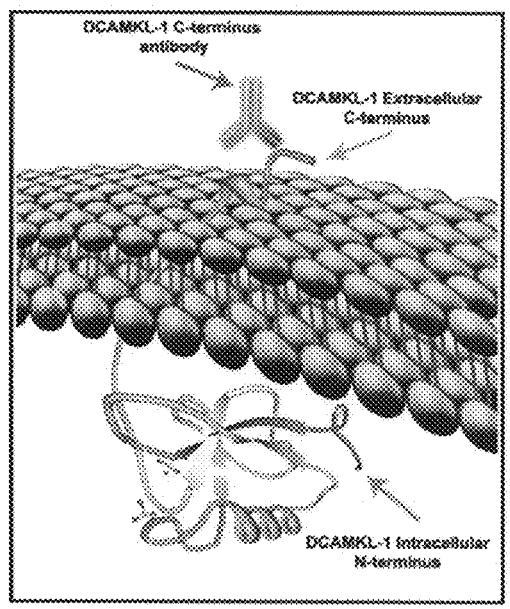

In general, cell surface proteins used for isolation of CSCs must currently be viewed as purification markers without functional implication [Diehn et al., 2006]. Therefore, it is critical to demonstrate that isolated cells from any particular tissue have the functional characteristics of CSCs. Currently, this has been most convincingly demonstrated by serial transplantation in animal models [Diehn et al., 2006]. CSCs share unique properties with normal adult stem cells, including the ability to self-renew and form spheroids. Indeed in the experiments described herein, stem cells isolated from normal mouse pancreas formed spheroids. Furthermore, 50-100 cells isolated from a particular spheroid were capable of initiating growth in the flanks of nude mice. In this Example, evidence is provided that demonstrates that DCAMKL-1, a novel stem cell marker expressed primarily in quiescent cells of the gut [May et al., 2008; Giannakis et al., 2006A], also marks normal pancreatic stem cells. One exciting outcome of this Example however, is the use of FACS for isolation of cells expressing DCAMKL-1. Although originally considered to be a cytoplasmic protein [Giannakis et al., 2006A], analysis of the DCAMKL-1 protein using TMPred program (http://www.ch.embnet.org/software/TMPRED_form.html) suggested that amino acids 534-560 represents a transmembrane domain, and amino acids 561 to 729 are outside the cell. Furthermore, it has been reported that DCAMKL-1 is expressed in adult brain with two transmembrane domains (amino acids 534-559 and 568-585), which strongly supports the suggestion that it is a cell surface expressing protein with both intra and extracellular domains [Sossey-Alaoui et al., 1999; Kim et al., 2003]. Cell surface DCAMKL-1 expression was demonstrated by Pierce® Cell Surface Protein Isolation Kit followed by Western Blot for DCAMKL-1 (data not shown). Accordingly, an Alexa Fluor® 568 conjugated anti-DCAMKL-1 antibody was generated, which targets the putative extracellular C-terminal epitope (FIG. 15). In this Example it has been demonstrated that putative stem cells isolated from the normal mouse pancreas formed early epithelial and islet-like structures and expressed markers of early pancreatic development, glandular epithelium, and islets in nude mice. In addition to expression in normal mouse pancreatic tissues, distinct DCAMKL-1 expression was also observed in representative human pancreatic cancers and the Pdx48$^{Cre}$-activated KRAS$^{G12D}$ mouse model of pancreatic cancer. Interestingly, marked coexpression of DCAMKL-1 was observed within tumors that expressed 14-3-3 σ, an inhibitor of Bad proapoptotic activity [Masters et al., 2001]. The co-localization demonstrated in this report of 14-3-3 σ and DCAMKL-1 is significant in that it could potentially define a target cell in which 14-3-3 σ related transcriptional activation within a tumor might occur. These data suggest that within a particular tumor, subsets of potential CSCs can be identified in situ. DCAMKL-1 immunostaining was observed in the intervening stroma between epithelial tumor elements, which co-expressed vimentin. These findings were indeed surprising in that DCAMKL-1 was not observed in non-epithelial cells under basal conditions. Next, ductal DCAMKL-1 was evaluated within PanIN lesions. Several thin, elongated cells that appeared to be mesenchymal were observed. To further investigate this, tumor sections were immunostained for vimentin, and cells of similar morphology were found interspersed between epithelial cells within PanIN lesions, which demonstrated distinct co-expression with DCAMKL-1. These findings suggest that DCAMKL-1 expressing cells may be undergoing EMT [Turley, et al., 2008; Reya et al., 2001]. EMT is a phenotypic conversion that facilitates organ morphogenesis and tissue remodeling in physiological processes such as embryonic development, wound healing, fibrosis, neoplasia and is associated with disease progression [Turley et al., 2008]. Desmoplasia, the appearance of fibrous, mesenchymal-like tissue in the peritumor stroma, is associated with poor clinical outcome [Poste et al., 1982]. Indeed, gene-profiling studies suggest that mesenchymal gene profiles in tumors is predictive of poor clinical outcome [Diehn et al., 2006; Theodosiou et al., 2003]. Myofibroblasts have long been thought to be derived from fibroblasts, but recent data has shown that a substantial proportion of these cells are derived from EMT and are associated with tumor progression [Polakis, 2000]. Our findings suggest that in addition to its role as a marker of pancreatic stem cells, DCAMKL-1 may additionally mark EMT within pancreatic cancer tissues.

Identification of stem cells within the normal pancreas and tumors has been generally elusive. Although recent studies using cell surface markers to isolate CSCs from tumors have been described, similar studies have not been performed utilizing normal tissues. However, in this Example, the novel stem cell marker DCAMKL-1 has been employed to identify stem cells in the normal mouse pancreas and in human and mouse pancreatic cancer.

Overall, the cancer stem cell hypothesis has many potential clinical applications, as it is becoming clear that CSCs must be removed in addition to the aberrantly proliferating cells within a particular cancer. Pancreatic cancer is an exceptionally aggressive disease and efforts directed at identification of novel therapeutic options aimed at improving the prognosis are essential. DCAMKL-1 may represent a new target for eliminating pancreatic cancer stem cells and the development of novel treatments for this devastating disease.

Example 3

The adult intestinal epithelium is continuously and rapidly replaced by cell replication within the crypts of Lieberkühn and subsequent migration of their progeny onto the villus epithelium in the small intestine, or onto the surface epithelium in the colon [Gordon et al., 1994]. Intestinal epithelial cells are ultimately derived from multipotent stem cell(s) located near the base of each intestinal crypt [Cheng et al., 1974; Cohn et al., 1992; Schmidt et al., 1985; Winton et al., 1990]. In the adult mouse small intestine, crypt stem cells divide to produce a daughter stem cell (self-renewal) as well as a more rapidly replicating transit amplifying (TA) cell. TA cells divide in the crypt proliferative zone and their progeny ultimately differentiate into the mature intestinal epithelial cell types [Cheng et al., 1974; Potten et al., 1987; Potten et al., 1990]. Knowledge of the biological characteristics of intestinal stem cells (ISCs) has been largely acquired by inference from experiments using chimeric and transgenic mice [Gordon et al., 1994; Schmidt et al., 1985; Hauft et al., 1992]. Bjerknes and Cheng [Bjerknes et al., 1981] originally proposed the existence of a stem cell-permissive microenvironment near the crypt base at positions 1-4 interspersed between Paneth cells. These cells, termed crypt base columnar (CBC) cells were proposed as ISCs [Cheng et al., 1974A] and were found to give rise to mutant clones containing multiple cell types [Bjerknes et al., 1999].

Adult stem cells in mammals exist either in a prolonged quiescent state or are extremely slow cycling [Cheshier et al., 1999]. Based on this feature, long-term label retention assays were developed to assist in the localization of putative stem cells [Cotsarelis et al., 1990; Zhang et al., 2003]. Using this technique, Potten et al., [Potten et al., 2002] localized label-retaining cells (LRCs) or putative ISCs to a position +4 from the crypt base, directly above the Paneth cell zone [Marshman et al., 2002]. However the +4 position is an average location and may vary depending on the crypt being analyzed. It is important to note that not all +4 cells are putative stem cells.

Recent work presented by Barker et al., [Barker et al., 2007] has identified a single marker, LGR5/GPR49 gene, a leucine-rich orphan G-protein-coupled receptor, that specifically labels stem cells in the mouse small intestine as well as other adult tissues. Furthermore, using mice generated from a LGR5-EGFP-IRES-Cre-ERT2×RosaLacZ cross, they demonstrated that LGR5+CBC cells are multipotent for all mature intestinal epithelial cell types, undergo self-renewal, persist for at least 60 days based on LacZ expression, and are resistant to irradiation [Barker et al., 2007]. Furthermore, LGR5 marked ISCs that were rapidly cycling (divide every 24 hours) under homeostatic conditions [Barker et al., 2007].

It has been demonstrated herein that doublecortin and $Ca^{2+}$/calmodulin-dependent kinase-like-1 (DCAMKL-1), a microtubule-associated kinase expressed in post-mitotic neurons [Lin et al., 2000], is a novel putative ISC marker [See Example 1, as well as Quante et al., 2008; Samuel et al., 2009; Humphries et al., 2008]. DCAMKL-1 was identified as a Gene Ontogeny-enriched transcript expressed in comparison with gastric epithelial progenitor and whole stomach libraries [Giannakis et al., 2006] and more recently in gastric stem cells [Giannakis et al., 2008]. Utilizing immunohistochemical analysis, cell-specific intestinal DCAMKL-1 expression patterns were demonstrated in adult wild type (WT) and in $Apc^{Min/+}$ mice to visualize crypt epithelial stem cells at baseline and in response to radiation injury [May et al., 2008]. Immunoreactive DCAMKL-1 cells were found at or near position +4, at a frequency of one cell per five crypts. DCAMKL-1+ CBC cells were also observed, albeit much less frequently.

In this Example, the cell specific expression patterns of DCAMKL-1 and LGR5 were investigated in intestinal epithelial cells in uninjured adult mice. DCAMKL-1 and LGR5 mark distinctly different cells. Moreover, DCAMKL-1 did not co-localize with other key markers such as chromogranin A (ChrA), phosphorylated PTEN (pPTEN), phosphorylated AKT (pAKT), somatostatin or secretin. Furthermore, using a combination of a modified label retention assay (mLRA) and immunohistochemical analysis, it was determined that DCAMKL-1 is expressed in quiescent label retaining cells within the intestinal crypt. LGR5 identifies proliferative CBC and TA cells in the gut as evidenced by co-labeling with proliferating cell nuclear antigen (PCNA). Additionally, early glandular epithelial structures were demonstrated in nude mice isografts following fluorescence activated cell sorting (FACS) of normal mouse intestinal epithelial cells using DCAMKL-1. Thus the inventors propose that the original hypothesis of a +4 ISC should not yet be abandoned and contend that the DCAMKL-1 expressing cell represents a quiescent ISC.

Materials and Methods for Example 3

Tissue preparation and immunohistochemistry. Heat Induced Epitope Retrieval was performed on formalin-fixed paraffin-embedded sections utilizing a pressurized Decloaking Chamber (Biocare Medical) in citrate buffer (pH 6.0) at 99° C. for 18 min. (a) Brightfield: Slides were incubated in 3% hydrogen peroxide, then normal serum and BSA at room temperature for 20 min. After incubation with primary antibody [DCAMKL-1 C-terminal (Abcam), LGR5 (Abcam), BrdUrd (Upstate), PCNA (Santa Cruz), Msi-1 (Abcam), Cytokeratin 14 (Santa Cruz), Math1 (Chemicon), L-FABP (Santa Cruz)], the slides were then incubated in peroxidase-conjugated EnVision™+ polymer detection kit (DAKO). Slides were developed with Diaminobenzidine (Sigma). (b) Fluorescence: Slides were first incubated in Image-iT FX signal enhancer (Invitrogen), followed by normal serum and BSA at room temperature for 20 min. After incubation with primary antibody, slides were incubated in appropriate Alexa Fluor® conjugated secondary [488 (green) and 568 (red)].

Microscopic examination. Slides were examined utilizing the Nikon 80i microscope and DXM1200C camera for brightfield. Fluorescent images were taken with PlanFluoro objectives, utilizing CoolSnap ES2 camera (Photometrics). Images were captured utilizing NIS-Elements software (Nikon). Confocal imaging was performed using Leica TCS NT Microscope.

Modified label retention assay. C57BL/6 mice (Jackson Labs) were subjected to 8 Gy whole body gamma irradiation using a Nordion $^{137}$Cs γ-irradiator with a dose rate of 0.9 Gy per minute. Animals received twice daily BrdUrd injections beginning 24 and ending 84 hr after irradiation. This time period was chosen in order to maximize the potential of label incorporation during the crypt regeneration phase, following severe genotoxic injury. Animals were sacrificed at 7 and 10 days after the initial injury when restoration of crypt villus morphology is returning towards baseline. Co-immunostaining for BrdUrd and DCAMKL-1 was performed to identify label retaining stem cells. Additionally co-immunostaining for PCNA and DCAMKL-1 was performed to determine the proliferative status of the label retaining cells.

Stem cell isolation. Based on protocols developed in intestinal stem cell biology [Dekaney et al., 2005; Grossmann et al., 2003], stem cells were isolated and propagated from fresh mouse intestinal tissues. Intestines were opened longitudinally and cut into small strips, washed and incubated with 1 mM DTT (Sigma) for 30 min at room temperature. Tissues were further incubated with 30 mmol/L EDTA (Sigma) for 10 min at 37° C., shaken vigorously in fresh HBSS (Cellgro) and filtered through 400 µm mesh (Spectrum Labs) to separate the detached intestinal crypt epithelial cells from the tissue. The filtrate was passed through 80 µm mesh (BD Falcon) to retain the crypts and washed. The crypts were digested at 37° C. to create a single cell suspension.

FACS. The cells isolated from mouse intestine were incubated with 1:100 dilution of Alexa Fluor® 568 (Invitrogen) conjugated DCAMKL-1 antibody (Abcam) for 30 min. The cells were washed twice with HBSS containing 10% serum and sorted using Influx-V cell sorter (Cytopeia). The cells collected were grown on DMEM containing EGF (25 ng/ml), FGF (20 ng/ml) and insulin (5 ng/ml) (Sigma), on non adherent/ultra low attachment plates (BD Biosciences).

Isotransplantation assay. DCAMKL-1+ cells isolated from intestine were grown in suspension culture and formed spheroids by day 21. Mechanically dissociated spheroids (50-100 cells) were suspended in Matrigel and injected subcutaneously into the flanks of athymic nude mice (n=3) (NCI-Fredrick) and monitored for the appearance of nodular growth.

Cell surface protein isolation and Western Blot analysis. SW480 colon cancer cells were grown and surface proteins were labeled with sulfo-NHS Biotin (Pierce, Thermo Scientific). Cell lysates were prepared and the biotinylated proteins were separated from intracellular non-biotinylated proteins as per manufacturer's instructions (Pierce). Protein concentration was determined by BCA protein assay kit (Pierce Biotechnology Inc., Rockford, Ill.). Forty μg of the protein was size separated in a 15% SDS polyacrylamide gel and transferred onto a nitrocellulose membrane with a semidry transfer apparatus (Amersham-Pharmacia, Piscataway, N.J.). The membrane was blocked in 5% non-fat dry milk for 1 h and probed overnight with a rabbit anti-DCAMKL-1 antibody (Abcam Inc.) or with rabbit anti-EGFR antibody (Cell Signaling Technology Inc.). Subsequently, the membrane was incubated with anti-rabbit IgG horseradish peroxidase-conjugated antibodies (Amersham-Pharmacia) for 1 h at room temperature. The 82 kDa DCAMKL-1 and 175 kDa EGFR proteins were detected using ECL™ Western Blotting detection reagents (Amersham-Pharmacia).

Results of Example 3

Figure 16:
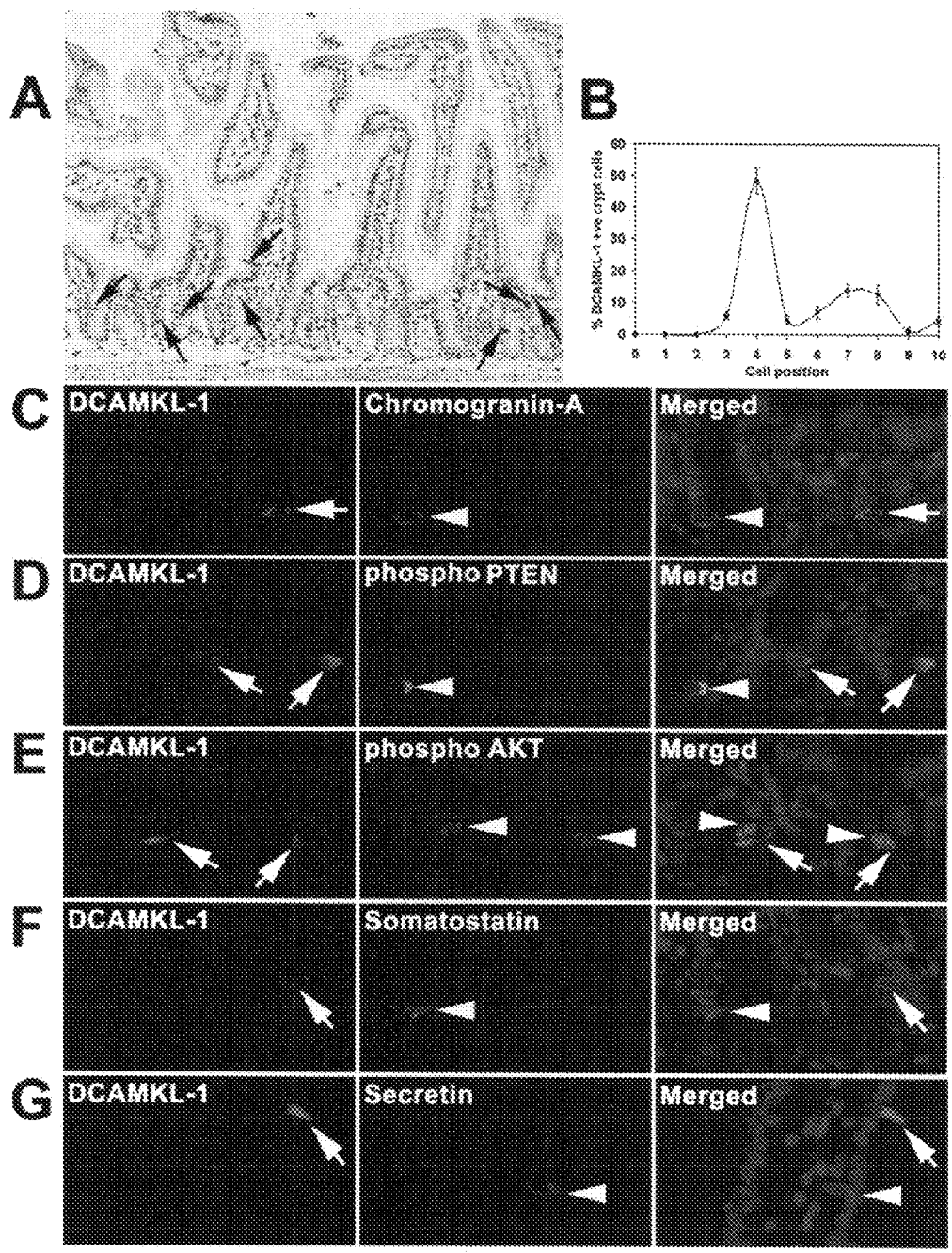

Intestinal DCAMKL-1 expression along the crypt-villus axis. Cellular distribution of DCAMKL-1 on a positional basis was determined in adult C57BL/6 mice (n=3). Longitudinal sections from the distal jejunum were prepared from each mouse and the number of immunoreactive DCAMKL-1 was determined by counting positive cells at the numbered positions (1-10), starting from the mid-point at the base of the crypt along the crypt-villus axis. Out of 500 total crypts counted, it was found that 49% of DCAMKL-1 positive cells were located at position +4 (excluding the CBCs) (FIGS. 16A, 16B). DCAMKL-1 was also expressed in rare CBCs (4% of total crypts counted). As previously reported, DCAMKL-1 cells were found in the villi [May et al., 2008]. However, it was noted that DCAMKL-1 crypt with simultaneous villus expression was rare (<5% of total crypt villus units).

DCAMKL-1 marks a unique intestinal cell type. To determine whether DCAMKL-1 was co-expressed with other putative stem cell and enteroendocrine markers, double-labeled immunofluorescence staining was performed for DCAMKL-1 with ChrA, pPTEN, pAKT, somatostatin and secretin. There was no co-localization observed for any of the markers tested (FIG. 16C-16G). These data demonstrate that DCAMKL-1 marks a unique cell within the crypt.

Figure 17:
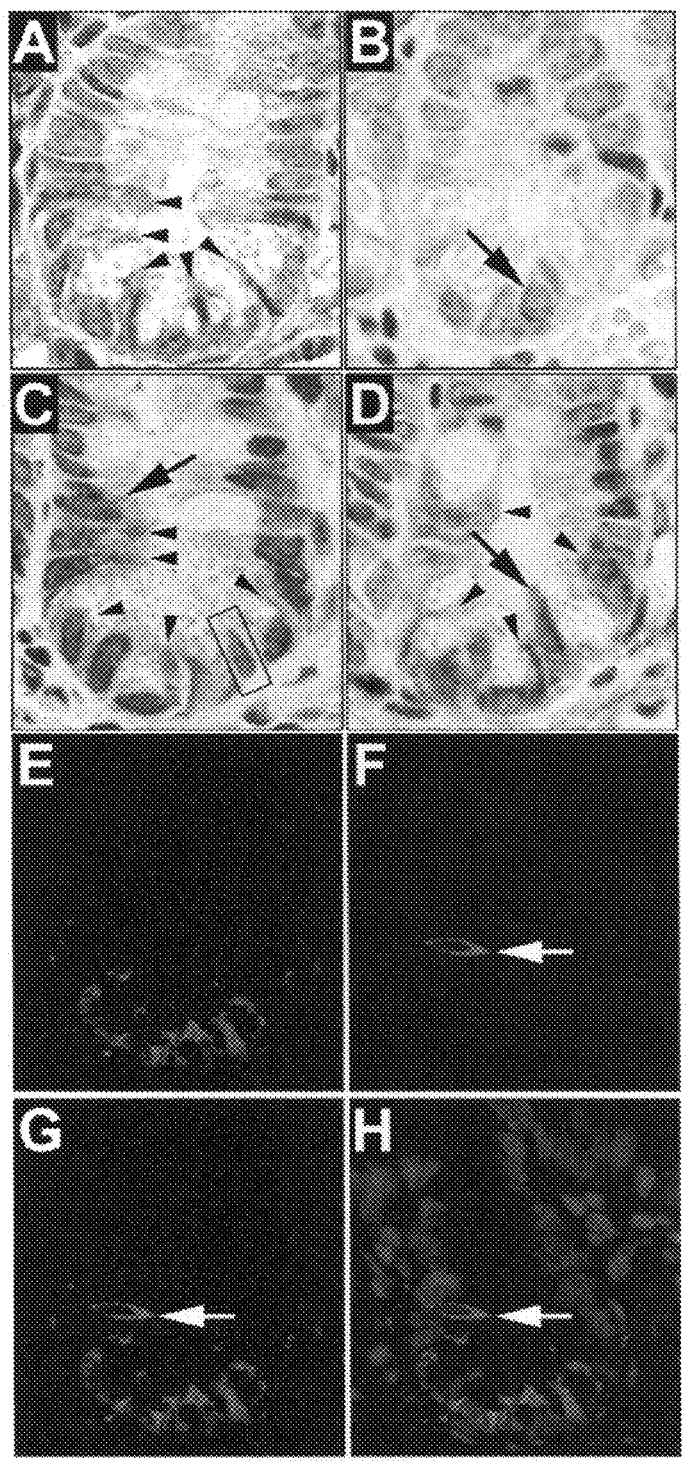

Intestinal LGR5 and DCAMKL-1 mark distinctly different cells. In the intestine, LGR5 expression was observed in crypt epithelial and in CBC cells as predicted (FIG. 17A). LGR5+ cells were also scattered throughout the mesenchyme and villus epithelial cells. This was consistent with the LacZ expression patterns described in the original LGR5 stem cell report [Barker et al., 2007], expression of LGR5 at the base of the crypt in normal human colon and small intestine [Becker et al., 2008] and the previously reported immunostaining for LGR5/GPR49 in colon and cancer tissues [McClanahan et al., 2006]. Example 1 demonstrated DCAMKL-1 expression at position +4 and in rare CBC cells [May et al., 2008] (FIG. 17B). On occasion, LGR5 expressing cells were immediately adjacent to DCAMKL-1+ cells (FIGS. 17C, 17D). However, no DCAMKL-1 co-localization with LGR5 was observed in intestinal crypts (FIG. 17E-17H).

Figure 18:
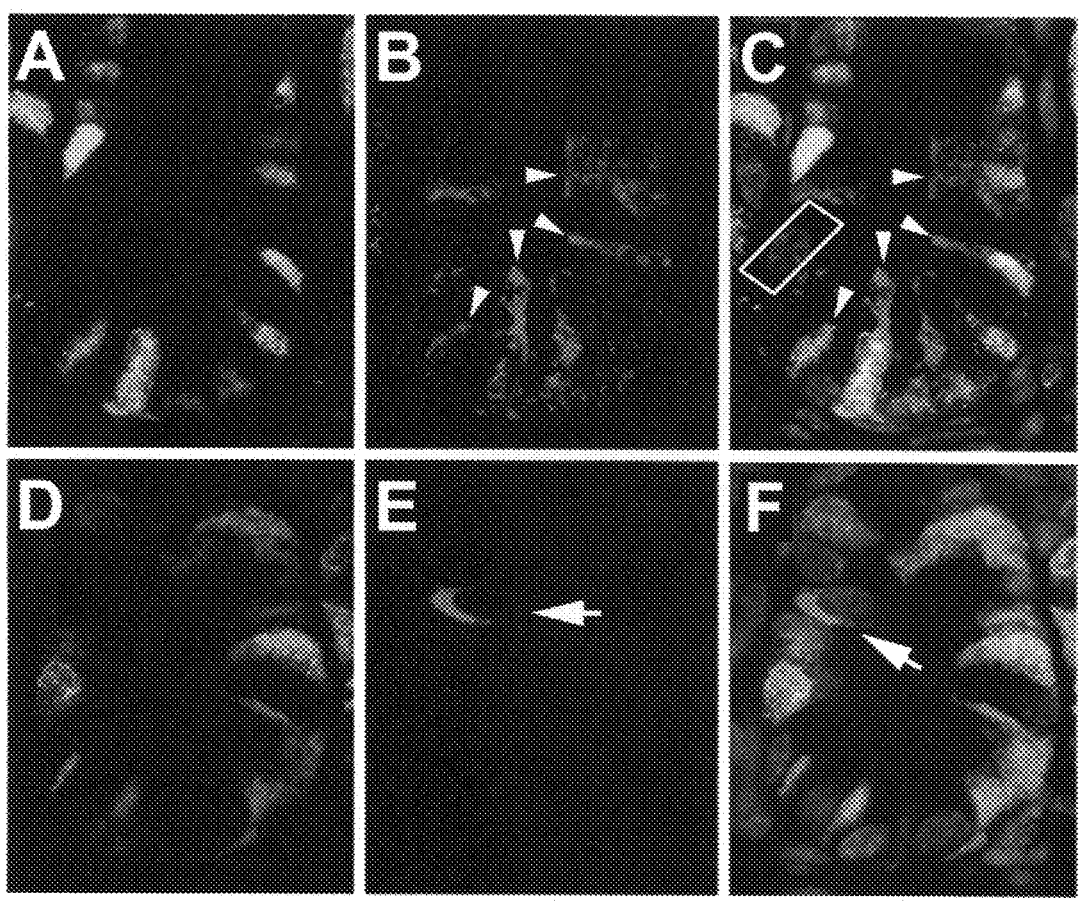

The proliferation status of LGR5 and DCAMKL-1 expressing cells. PCNA staining was performed to assess the proliferative status of LGR5 and DCAMKL-1 expressing cells in the intestine. LGR5 expressing cells were invariably PCNA+ (actively cycling) (FIG. 18A-18C). Occasionally, cells were noted at position +4 that did not express either PCNA or LGR5 (FIG. 18C white box). PCNA-cells, particularly at position +4, were distinctly DCAMKL-1+ (FIG. 18D-18F) suggesting functional quiescence at baseline. Thus, DCAMKL-1 and LGR5 identify cell populations with differing proliferation status at baseline. These findings lend support to the longstanding +4 hypothesis, which suggests that a functionally quiescent or very slowly cycling cell is primarily anchored in the stem cell niche [Potten et al., 2002; Marshman et al., 2002; Potten et al., 1997]. The inventors contend that this quiescent cell is marked by DCAMKL-1.

Figure 19:
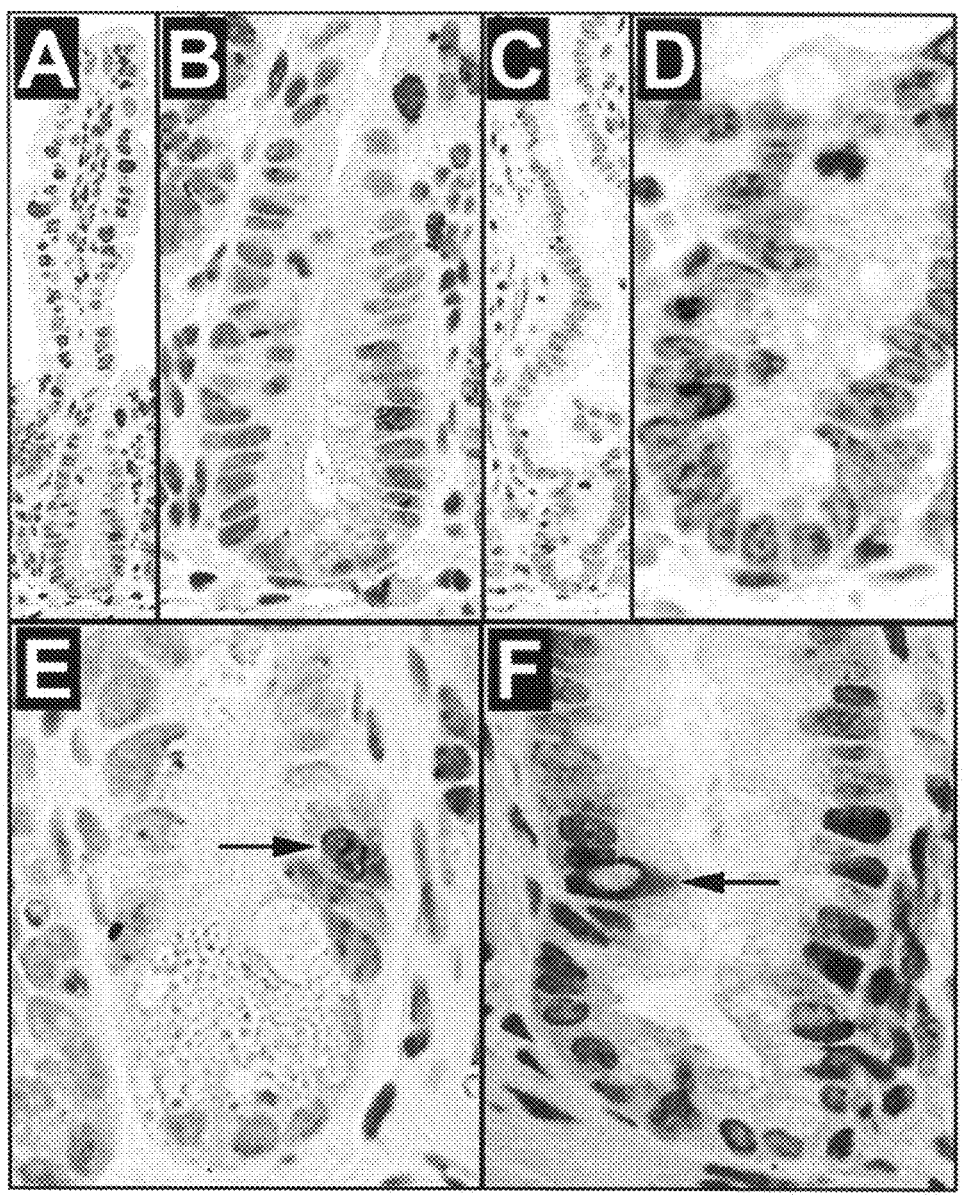

DCAMKL-1 label-retaining cells are functionally quiescent. Although the "anchored stem cell" is often found at position +4, the inventors suspect that under certain conditions this cell can exit the niche [Frye et al., 2003]. Indeed, occasionally DCAMKL-1 staining was observed outside of the crypt, particularly in $APC^{min/+}$ mice [May et al., 2008]. A modification of the traditional label retention assay (mLRA) [Cotsarelis et al., 1990; Zhang et al., 2003; Potten et al., 2002; Marshman et al., 2002] was employed by utilizing 8 Gy as the inciting dose in adult WT mice. DCAMKL-1 expression is lost in regenerative crypts by 84 hr after lethal dose IR (>8 Gy) but reappears 7 and 10 days following IR in regenerated intestine tissues [May et al., 2008]. This suggests that by 7 to 10 days after IR, the normal crypt villus units and the niche related micro-environmental signals required for DCAMKL-1 expression are restored. Example 1 demonstrated that 24 hrs after IR is a critical time point when DCAMKL-1 expressing cells undergo both mitosis and apoptosis [May et al., 2008]. Thus it was decided to pulse label 5-bromo-2'-deoxyuridine (BrdUrd) throughout the entire 24-84 hr crypt regeneration cycle. Animals were allowed to recover and were sacrificed at 7 and 10 days [Potten et al., 1988]. This period of regeneration allows for BrdUrd incorporation into dividing stem cells that would otherwise be problematic under quiescent basal conditions. At 7 days post IR, residual BrdUrd labeled cells were detected in the upper crypt and throughout the villi (FIGS. 19A, 19B). However at 10 days, BrdUrd labeling had essentially disappeared, and only rare cells near the crypt base retained significant label (FIGS. 19C, 19D).

Next, it was sought to determine whether the cells retaining BrdUrd label following the mLRA also expressed DCAMKL-1. At 10 days post IR, double-label immunohistochemistry was performed, and distinct co-expression of BrdUrd and DCAMKL-1 at position +4 was observed (FIG. 19E). While this cell retains label, it does not necessarily mean that it was actively proliferating. It was sought to answer this question by examining DCAMKL-1 expressing cells following the mLRA for the presence of PCNA activity. Interestingly, there was no PCNA expression in the nucleus of the DCAMKL-1+ cell. Yet clear PCNA staining could be identified in many adjacent cells (FIG. 19F). Thus the label retaining DCAMKL-1 expressing "stem cells" are again quiescent at 7 and 10 days after IR.

Figure 20:
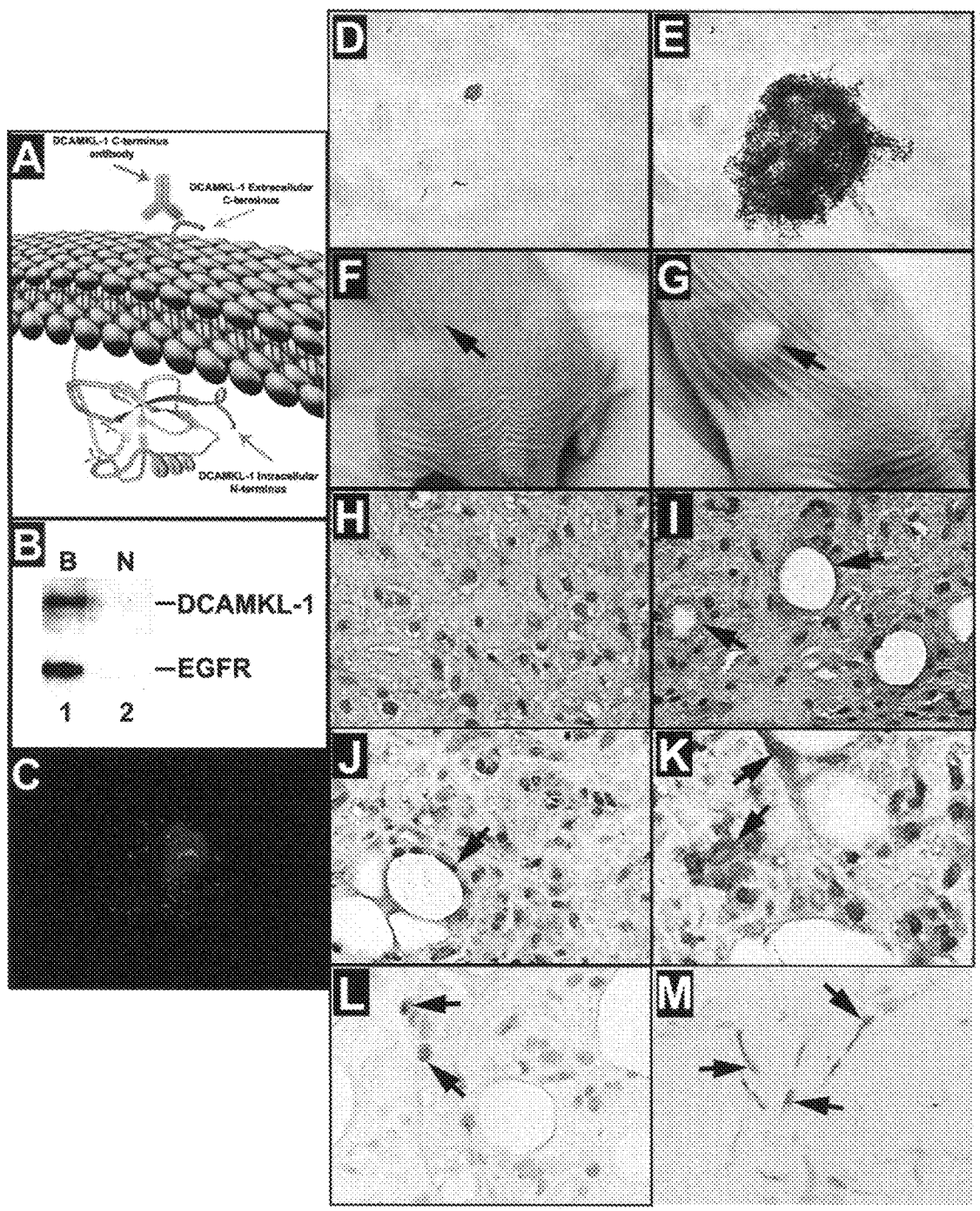
Figure 21:
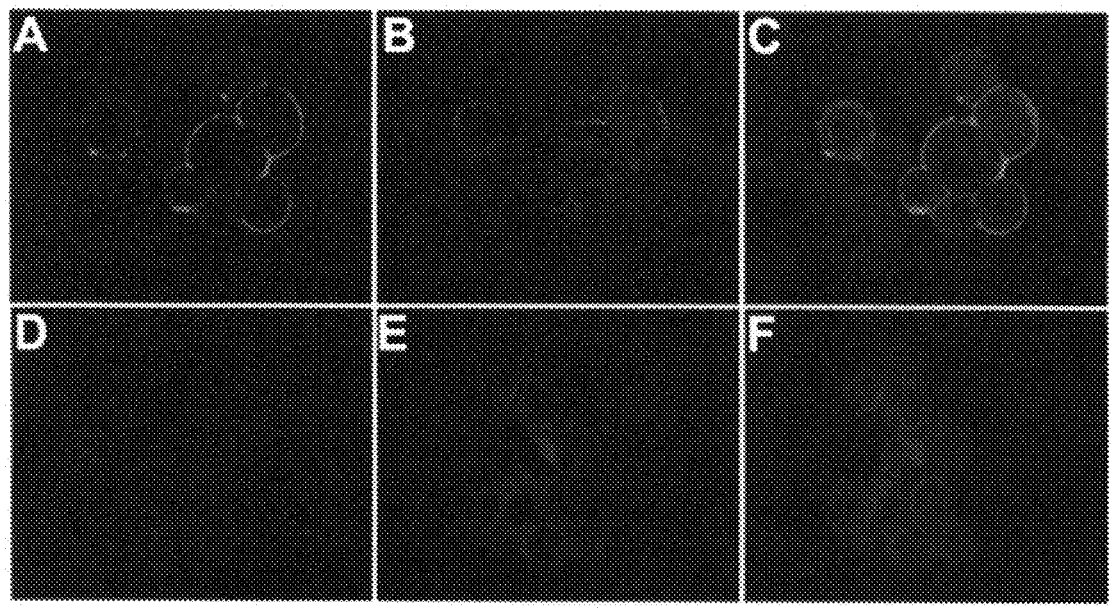

DCAMKL-1 is expressed on the cell surface and can be used to isolate stem cells. To further investigate the potential "stemness" of DCAMKL-1 expressing cells, FACS using the modified protocol of Dekaney et al., [Dekaney et al., 2005] was employed. Although originally considered to be a cytoplasmic protein [Giannakis et al., 2006], analysis of the DCAMKL-1 protein using TMPred program (http://www.ch.embnet.org/software/TMPRED_form.html) suggested that amino acids 534-560 constitutes a transmembrane domain, and amino acids 561 to 729 are extracellular. Furthermore, it has been reported that DCAMKL-1 is expressed in adult brain with two transmembrane domains (amino acids 534-559 and 568-585), suggesting that it is a cell surface expressing protein with intra and extracellular domains [Sossey-Alaoui et al., 1999; Kim et al., 2003] (FIG. 20A). To confirm the cell surface expression of DCAMKL-1, the Pierce Cell Surface Protein Isolation Kit (Pierce) was used to isolate total cell surface expressing proteins from SW480 cells (FIG. 21). Western blot analyses demonstrated the presence of DCAMKL-1 in the avidin-bound fraction, but not in the unbound fraction (FIG. 20B). This data demonstrates that DCAMKL-1 protein is indeed present on the cell surface. Epithelial growth factor receptor (EGFR), a cell surface expressing protein in the bound fraction was used as a positive control.

Figure 22:
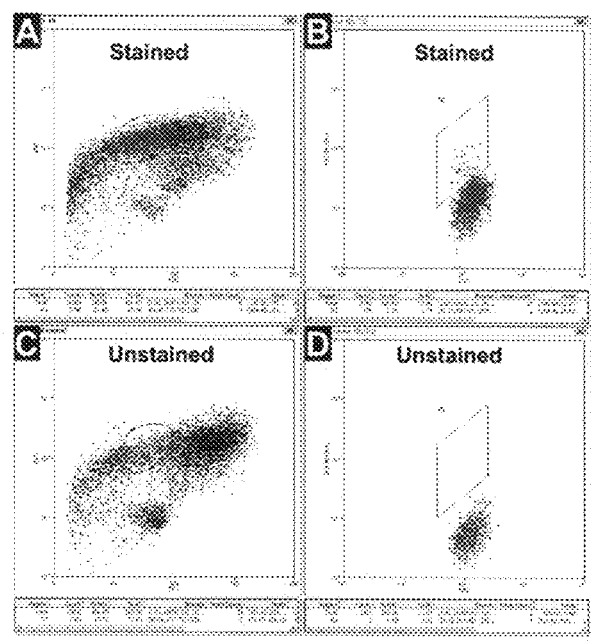
Figure 23:
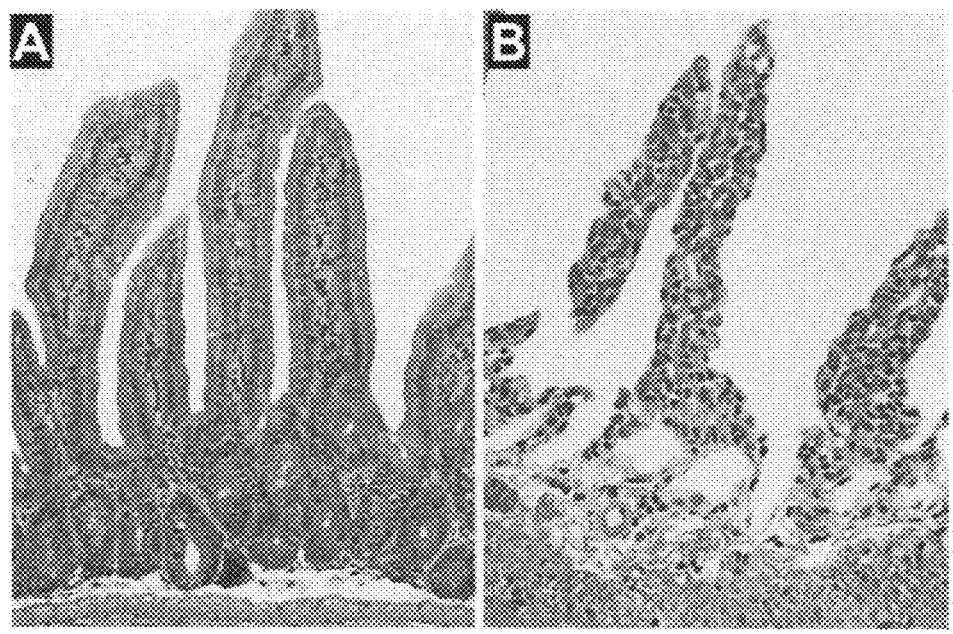
FIG. 23 illustrates mouse intestine (distal jejunum) before and after epithelial cell isolation. (A): Intact epithelium before isolation. (B): Intestine devoid of epithelial cells after isolation.
Figure 24:
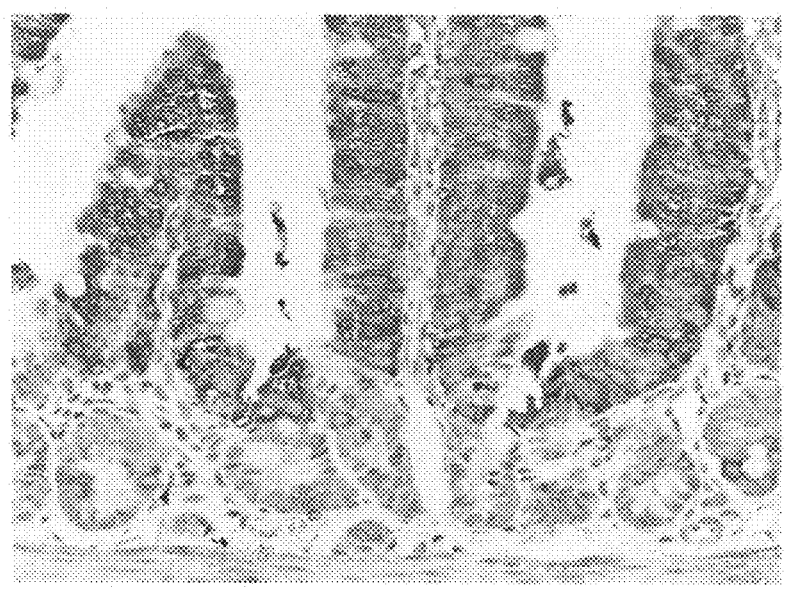
FIG. 24 illustrates mouse intestine (distal jejunum) immunostained for L-FABP (brown). Immunoreactive L-FABP is observed in occasional crypt epithelial cells; however, intense staining is observed in differentiated villus epithelial cells.

Anti-DCAMKL-1 antibody, which targets the extracellular C-terminal epitope [Lin et al., 2000; Sossey-Alaoui et al., 1999; Kim et al., 2003], was conjugated with Alexa Fluor® 568 to label intact functional stem cells from the normal mouse intestine for FACS. For sorting, gate R1 was assigned based on previous experiments, where the DCAMKL-1+ fluorescing cell population was found aggregated within that location. These cells were further gated through R2 based on fluorescence intensity (FIG. 22). Approximately 1.75% of the total cells sorted were isolated using this method (FIGS. 22-23). Sorted cells were examined by fluorescence microscopy to confirm the presence of DCAMKL-1 (FIG. 20C). The cells were then grown in suspension culture with growth factor supplemented media using the method of Dontu et al. [Dontu, 2003]. After 3 weeks, the single DCAMKL-1+ sorted cells formed spheroids (FIGS. 20D, 20E); whereas DCAMKL-1-sorted cells did not (data not shown). The spheroids containing 50 to 100 cells were mechanically dissociated and subsequently injected into contralateral flanks of nude mice. After 3 weeks nodular structures were observed (FIGS. 20F, 20G) in 11 of 12 spheroid injection sites (data not shown). Two weeks later, animals were sacrificed and nodules excised and subjected to immunohistochemical and histological analysis. In the control (Matrigel injected) nodules, an inflammatory response was observed including the presence of macrophages, but with no evidence of epithelial cells (FIG. 20H). In the spheroid injected nodules however, there were single cells with oval nuclei and large nucleoli which lined up around central spaces and appeared to represent poorly formed glands (FIG. 20I). Cytokeratin 14 immunoreactivity demonstrates that these cells were of glandular epithelial origin [Moll et al., 2008; Purkis et al., 1990] (FIG. 20J). To determine whether they expressed stem and/or TA (progenitor) cell markers, the inventors stained for the epithelial stem/progenitor cell marker Msi-1 [Sureban et al., 2008; Potten, 2003]. Significant Msi-1 immunoreactivity was observed in these epithelial structures providing additional support for the epithelial and perhaps stem/progenitor cell origin of these cells (FIG. 20K). Moreover, several cells expressed Math1 indicating an early intestinal epithelial secretory lineage commitment (goblet, enteroendocrine and Paneth cells) [Yang et al., 2001; Shroyer et al., 2005] and L-type fatty acid binding protein (L-FABP) (marker of enterocyte lineage) [Rubin et al., 1992] (FIGS. 20L, 20M and 24). These studies demonstrate that DCAMKL-1 can be used as a cell surface marker to isolate stem cells from the normal mouse intestine and investigate their lineage determination and viability in vivo.

Discussion of Example 3

In this Example, it has been demonstrated that the novel stem/progenitor markers DCAMKL-1 and LGR5 identify intestinal stem and progenitor cells, respectively. This distinction is primarily based on the proliferative status of the cells, because no in vivo genetic lineage tracing studies have yet been performed for DCAMKL-1. The major distinguishing feature presented here is that DCAMKL-1 identifies a slowly cycling or basally quiescent cell; whereas LGR5 identifies a more proliferative cell. It is important to note that these classifications do not necessarily address the question of multipotency, as it is clear that an early intestinal progenitor cell is capable of repopulating the crypt with each of the four cell types expressed in the intestine [Crossman et al., 1994]. This Example demonstrates that there may be two different populations of stem cells in the gut. One population is at or near the traditional +4 position, and is restricted primarily to the niche and may have a functional role in gut homeostasis and injury response. The second population is interspersed between the Paneth cells (CBCs) and may be responsible for Paneth cell repopulation in response to bacterial mediated injury.

These results have been supported by the recent report by Sangiorgi and Capecchi [Sangiorgi et al., 2008] identifying Bmi1 as yet another novel ISC marker. In that report using a knock-in transgenic mouse model, they presented data demonstrating that Bmi1 labels ISCs predominantly at the +4 position of the crypt. The authors suggest that Bmi1 and LGR5 label different states of ISCs. Bmi1 labels the more quiescent ISCs, while LGR5 labels ISCs more prone to enter proliferation [Sangiorgi et al., 2008]. The results of this Example are further supported by reports that the putative stem/progenitor cell markers DCAMKL-1, LGR5 and Msi-1 [Quante et al., 2008; Samuel et al., 2009; Humphries et al., 2008] are all expressed in CBC cells [Barker et al., 2007; May et al., 2008; Potten, 2003]. One exciting outcome of this Example is the use of FACS for isolation of cells expressing DCAMKL-1. Although originally considered to be a cytoplasmic protein [Giannakis et al., 2006], it has been reported that DCAMKL-1 is expressed in adult brain with two transmembrane domains (amino acids 534-559 and 568-585), making it a cell surface expressing protein with intra and extracellular domains [Sossey-Alaoui et al., 1999; Kim et al., 2003]. In this Example, cell surface isolation experiments confirm that DCAMKL-1 is indeed expressed on the cell surface. Accordingly, anti-DCAMKL-1 antibody was conjugated with Alexa Fluor® 568 for use in cell sorting experiments. This Example demonstrated that putative stem cells isolated from the normal mouse intestine by FACS form spheroids in suspension culture, and upon injection into the flanks of nude mice form early glandular epithelial structures. Moreover, these cells expressed Msi-1 [Sureban et al., 2008; Potten, 2003], Cytokeratin 14 [Moll et al., 2008; Purkis et al., 1990], Math1 [Yang et al., 2001; Shroyer et al., 2005] and L-FABP [Rubin et al., 1992], markers of intestinal epithelial lineage.

The data presented in this Example demonstrate that LGR5+ and DCAMKL-1+ cells are distinctly different and may even have different functions. However, it is predicted that both of these cell types are likely to have full multipotency and have the potential to regenerate a fully functional gastrointestinal tract following injury. The present Example demonstrates that for the first time these critical cell types can be identified in situ based on the discovery of these two novel markers. FIG. 25 presents a model for the specific expression patterns of the putative markers DCAMKL-1, Msi-1 and LGR5 in the intestinal crypts.

The importance of reliable markers for identifying both stem and progenitor cells goes well beyond their use as a tool for sorting. The unique expression of DCAMKL-1 in quiescent ISCs raises the question of whether functional quiescence is a requirement for gut homeostasis, and what factors regulate these processes. Identification of DCAMKL-1 and LGR5 expressing cells will enable for the first time the direct examination of the gene expression profiles and molecular signatures of stem and progenitor cells, respectively.

Example 4

MicroRNAs (miRNAs) are small, non-coding RNAs that regulate gene expression in animal and plant systems [Lee et al., 2001; Lagos-Quintana et al., 2001]. miRNAs have emerged as important developmental regulators and control critical processes such as cell fate determination and cell death [Bartel, 2004]. There is increasing evidence that several miRNAs are mutated or poorly expressed in human cancers and may act as tumor suppressors or oncogenes [McManus, 2003; Takamizawa et al., 2004]. Gene expression is regulated by miRNAs through complementary elements in the 3' untranslated regions (3'UTRs) of their target messenger RNAs (mRNAs) [Vella et al., 2004]. lethal-7 (let-7), a founding member of the miRNA family, is required for timing of cell fate determination in C. elegans [Reinhart, 2000]. In humans, various let-7 genes have been reported to map to regions that are deleted in human cancers [Calin, 2004]. In addition, let-7 is poorly expressed in lung cancers [Takamizawa, 2004], suggesting that let-7 miRNAs may be tumor suppressors. In support of this, overexpression of let-7 inhibited cell growth of a lung cancer cell line in vitro [Takamizawa, 2004].

Mature miRNAs are produced from primary miRNA transcripts (pri-miRNAs) through sequential cleavages by the Microprocessor complex, comprising the ribonuclease III Drosha component and the double-stranded RNA (dsRNA) binding protein DGCR8 [Gregory, 2004] and Dicer [Chendrimada et al., 2005]. This coordinated enzyme complex results in the release of pri-miRNA and mature miRNA species. Posttranscriptional control of miRNA expression has been reported to occur in a tissue-specific [Obernosterer et al., 2006] and developmentally regulated fashion [Viswanathan et al., 2008; Thomson et al., 2006]. In mouse embryonic stem (ES) cells and in mouse embryonal carcinoma (EC) cells, the magnitude of the Microprocessor processing block is greatest for members of the let-7 family of miRNAs; although it is quite possible that the processing of all miRNAs may be regulated at the Microprocessor step [Viswanathan et al., 2008; Thomson et al., 2006]. It has been recently discovered that in many cancers, the miRNA profile is altered when compared to normal tissue [Calin et al., 2006]. It is becoming increasingly recognized that most cancers have a stem-cell-like compartment that is responsible for inciting and sustaining tumorigenesis [Calin et al., 2006; Jones et al., 2007]. One might hypothesize that miRNA profiles are altered in cancer stem cells (CSCs) within a particular tumor. Moreover, it is quite possible that such alterations are key factors in the initiation of the CSC. Recent evidence suggests that several miRNAs may be responsible for maintaining stem-cell-like characteristics [Bussing et al., 2008; Hatfield et al., 2005].

Furthermore, miRNA profiling of human and mouse ES cells reveals high levels of miRNAs expression, previously associated with oncogenesis and cell-cycle control [Suh et al., 2004; Calabrese et al., 2007]. Moreover, lack of let-7 miRNA expression was observed as an indicator for "stemness" in epithelial progenitor cells. Recent studies have also demonstrated that let-7 expression is absent in certain tumor cell lines, and that re-introduction of let-7 into these cells causes differentiation and reduction in proliferation and tumor-forming ability [Giannakis et al., 2006; May et al., 2008; Dekaney et al., 2005]. The regulatory mechanisms that control the maturation process of miRNA are unclear and the regulatory factors that control let-7 miRNA levels, particularly in epithelial stem/progenitor cells, are completely unknown. The study of epithelial stem cell biology has been hampered by the lack of reliable stem cell markers that distinctly define and distinguish between stem and progenitor cell populations. There has been an accelerated interest, however, in defining these populations, as it is becoming increasingly clear that many important diseases including cancers are likely driven by effects on stem and/or progenitor cells.

Example 1 demonstrated that the novel putative intestinal stem cell marker DCAMKL-1, a microtubule associated kinase expressed in post mitotic neurons [Lin et al., 2000] and in the stomach [Giannakis et al., 2006], is expressed in the intestine, colon and Apc$^{Min/+}$ adenomas [May et al., 2008]. Given the importance of stem cells in mucosal regeneration and neoplasia, it was sought to determine whether DCAMKL-1 played a functional role in tumorigenesis and whether these effects were mediated through regulation of let-7α miRNA.

Materials and Methods of Example 4

Cell culture. HCT116, HCT116 p21$^{-/-}$ and SW480 human colon adenocarcinoma cell lines were obtained from the American Type Culture Collection (ATCC) and grown in Dulbecco's modified eagle's medium (DMEM) supplemented with 10% fetal bovine serum and 100 U/mL penicillin-streptomycin in a humidified chamber at 37° C. with 5% $CO_2$.

Silencer RNA. DCAMKL-1 siRNA (si-DCAMKL-1) sequence targeting the coding region of DCAMKL-1 (Accession #NM_004734 (SEQ ID NO:1)) (GGGAGUGAGAA-CAAUCUAC (SEQ ID NO:3)) and scrambled control siRNAs (si-Scr) not matching any of the human genes were obtained (Ambion Inc., Austin, Tex.) and transfected using Transfectol™ (Ambion Inc.).

Real-time reverse transcription-PCR analyses. Total RNA isolated either from cells or from human colon cancer cell tumor xenograft samples was subjected to reverse transcription with Superscript™ II RNase H-Reverse Transcriptase and random hexanucleotide primers (Invitrogen, Carlsbad, Calif.). The cDNA was subsequently used to perform Real-time PCR by SYBR chemistry (SYBR® Green I; Molecular Probes) for specific transcripts using gene specific primers and Jumpstart Taq DNA polymerase (Sigma-Aldrich, St. Louis, Mo.). The crossing threshold value assessed by Real-time PCR was noted for the transcripts and normalized with β-actin mRNA. The changes in mRNA were expressed as fold change relative to control with ±SEM value.

Human primers used are:

```
                                           (SEQ ID NO: 4)
β-actin:    Forward: 5'-GGTGATCCACATCTGCTGGAA-3'
                                           (SEQ ID NO: 5)
            Reverse: 5'-ATCATTGCTCCTCCTCAGGG-3'

(SEQ ID NO: 6)
DCAMKL-1:   Forward: 5'-AGTCTTCCGATTCCGAGTTGAG-3'
                                           (SEQ ID NO: 7)
            Reverse: 5'-CAGCAACCAGGAATGTATTGGA-3'

(SEQ ID NO: 8)
c-Myc:      Forward: 5'-CACACATCAGCACAACTACGCA-3'
                                           (SEQ ID NO: 9)
            Reverse: 5'-TTGACCCTCTTGGCAGCAG-3'
```

Mouse primers used are:

```
                                         (SEQ ID NO: 10)
DCAMKL-1:   Forward: 5'-CAGCCTGGACGAGCTGGTGG-3'
                                         (SEQ ID NO: 11)
            Reverse: 5'-TGACCAGTTGGGGTTCACAT-3'
``` miRNA analysis. Total miRNA was isolated using mirVana™ miRNA isolation kit (Ambion Inc.). Total miRNA isolated either from cells or from human colon cancer cell tumor xenograft samples were subjected to reverse transcription with Superscript™ II RNase H-Reverse Transcriptase and random hexanucleotide primers (Invitrogen, Carlsbad, Calif.). The cDNA was subsequently used to perform Real-time PCR by SYBR chemistry (SYBR® Green I; Molecular Probes) for pri-let-7α transcript using specific primers and Jumpstart Taq DNA polymerase (Sigma-Aldrich, St. Louis, Mo.). The crossing threshold value assessed by Real-time PCR was noted for pri-let-7α miRNA and normalized with U6 pri-miRNA. The changes in pri-miRNA were expressed as fold change relative to control with ±SEM value. Primers used are:

```
                                         (SEQ ID NO: 12)
pri-U6:     Forward: 5'-CTCGCTTCGGCAGCACA-3'
                                         (SEQ ID NO: 13)
            Reverse: 5'-AACGCTTCACGAATTTGCGT-3'

(SEQ ID NO: 14)
pri-let-7a: Forward: 5'-GAGGTAGTAGGTTGTATAGTTTAGAA-3'
                                         (SEQ ID NO: 15)
            Reverse: 5'-AAAGCTAGGAGGCTGTACA-3'
```

Western Blot analysis. HCT116 and SW480 cells were cultured in a 6 well plates to 40% confluency and were transfected with si-DCAMKL-1 or si-Scr for 72 h. Cells or the tumor xenograft samples were lysed and the concentration of protein was determined by BCA protein assay kit (Pierce Biotechnology Inc., Rockford, Ill.). Forty µg of the protein was size separated in a 7.5-15% SDS polyacrylamide gel and transferred onto a nitrocellulose membrane with a semidry transfer apparatus (Amersham-Pharmacia, Piscataway, N.J.). The membrane was blocked in 5% non-fat dry milk for 1 h and probed overnight with a rabbit anti-DCAMKL-1 antibody (Abcam Inc., Cambridge, Mass.) or with rabbit anti-c-Myc antibody (Santa Cruz). Subsequently, the membrane was incubated with anti-rabbit or anti-goat IgG horseradish peroxidase-conjugated antibodies (Amersham-Pharmacia) for 1 h at room temperature. The 82 kDa DCAMKL-1 and 49 kDa c-Myc proteins were detected using ECL™ Western Blotting detection reagents (Amersham-Pharmacia). Actin (43 kDa), used as loading control was identified using a goat polyclonal IgG (Santa Cruz Biotechnology Inc., Santa Cruz, Calif.).

Immunohistochemistry. Heat Induced Epitope Retrieval was performed on 4 µm formalin-fixed paraffin-embedded sections utilizing a pressurized Decloaking Chamber (Biocare Medical) in citrate buffer (pH 6.0) at 99° C. for 18 min. (a) Brightfield: Slides were incubated in 3% hydrogen peroxide, then normal serum and BSA at room temperature for 20 min. After incubation with primary antibody [DCAMKL-1 C-terminal (Abcam), anti-c-Myc (Santa Cruz Biotechnologies), L-FABP (Santa Cruz Biotechnologies)], the slides were incubated in peroxidase-conjugated EnVision™+ polymer detection kit (DAKO). Slides were developed with Diaminobenzidine (Sigma). (b) Fluorescence: Slides were first incubated in Image-iT FX signal enhancer (Invitrogen), followed by normal serum and BSA at room temperature for 20 min. After incubation with primary antibody [L-FABP (Santa Cruz Biotechnologies)], slides were incubated in appropriate Alexa Fluor® conjugated secondary [488 (green)].

Microscopic Examination. Slides were examined utilizing the Nikon 80i microscope and DXM1200C camera for brightfield. Fluorescent images were taken with PlanFluoro objectives, utilizing CoolSnap ES2 camera (Photometrics). Images were captured utilizing NIS-Elements software (Nikon).

Stem cell isolation. Based on protocols developed in intestinal stem cell biology [Dekaney et al., 2005; Grossmann et al., 2003], stem cells were isolated from mouse intestine. The intestine was chopped into small strips, washed and incubated with 1 mM DTT (Sigma) for 30 min at room temperature. It was further incubated with 30 mmol/L EDTA (Sigma) for 10 min at 37° C. The strips were shaken vigorously in fresh HBSS (Cellgro) and filtered through 400 µm mesh (Spectrum Labs) to separate the detached intestinal crypt epithelial cells from the tissue. The filtrate was passed through 80 µm mesh (BD Falcon) to retain the crypts and washed. The crypts were digested at 37° C. to create a single cell suspension.

FACS. The cells isolated from mouse intestine were incubated with 1:100 dilution of Alexa Fluor® 568 (Invitrogen) conjugated DCAMKL-1 antibody (Abcam) for 30 min. The cells were washed twice with HBSS containing 10% serum and sorted using Influx-V cell sorter (Cytopeia). DCAMKL-1 positively and negatively sorted cells were collected and subjected to total mRNA and miRNA isolation. mRNA was reverse transcribed and subjected to real-time RT-PCR for DCAMKL-1. Total miRNA was subjected to real-time RT-PCR for pri-let-7α miRNA.

Xenograft tumor model. (a) Liposomal preparation: siRNA was administered into the xenografts after incorporation into 1,2-Dioleoyl-sn-Glycero-3-Phosphocholine (DOPC) (Avanti Polar Lipids, Alabaster, Ala.). DOPC and siRNA were mixed in the presence of excess tertiary butanol at a ratio of 1:10 (w/w) (siRNA/DOPC). Tween 20 (Sigma-Aldrich) was added to the mixture at a ratio of 1:19 Tween 20:siRNA/DOPC. The mixture was vortexed and frozen in an acetone/dry ice bath and lyophilized. Before administration, the siRNA preparation was reconstituted in 0.9% sterile saline and injected at a dose of 50 µl (5 µM) per injection. (b) Tumor therapy: Female athymic nude mice (NCr-nu) were purchased from the National Cancer Institute-Frederick Cancer Research and Development Center (Frederick, Md.) and housed in specific pathogen-free conditions. They were cared for in accordance with guidelines set forth by the American Association for Accreditation of Laboratory Animal Care and the USPHS "Policy on Human Care and Use of Laboratory Animals," and all studies were approved and supervised by the Institutional Animal Care and Use Committee. HCT116 cells ($6 \times 10^6$) were injected subcutaneously into the flanks of 4-6 week-old female athymic nude mice (5 mice per group). Tumors were measured with calipers and the volume was calculated as (length×width$^2$)×0.5. The tumors reached 1000 mm$^3$ after 15 days of injection of cells. These tumors were injected with 50 µl (5 µM) of siRNA preparation on every third day from day 15 for a total of 5 doses.

Luciferase reporter gene assay. pLet7α-Luc reporter vector contains a let-7α miRNA specific binding site at the 3'UTR of the firefly (*Photinus pyralis*) luciferase gene obtained from Signosis Inc (FIG. 26). HCT116 and SW480 cells were transfected with the pLet7α-Luc reporter vector, *Renilla* luciferase expressing plasmid pRL-TK (Promega) along with DCAMKL-1 or scrambled siRNA using Transfectol™ (Ambion Inc.). Luciferase activity was determined as per the manufacturer's instructions (Dual-Luciferase Reporter Assay System; Promega) using a Monolight 2010 luminometer (Analytical Luminescence Laboratory, San Diego, Calif.) as described earlier [Stadler et al., 2008; Sossey-Alaoui et al., 1999]. The activity, normalized to *Renilla* Luciferase activity, is presented as relative luciferase units relative to control with ±SEM values. Assays were performed in triplicate wells and experiments were repeated 3 times.

Statistical analysis. All the experiments were performed in triplicate. The data was analyzed by Student's t-test. Where indicated, the data is presented as mean±SEM. A p value of <0.01 was considered statistically significant.

Results of Example 4

DCAMKL-1 is overexpressed in cancer. To determine whether DCAMKL-1 was expressed in human colorectal cancers, immunohistochemical analysis was performed on human cancer tissue microarrays (Tissue Array Network and National Cancer Institute—Tissue Array Research Program). Staining revealed increased DCAMKL-1 protein (FIG. 27A; brown—indicated by black arrows) in human colorectal cancers specimens, compared to normal colonic mucosa. In tumors, the staining pattern was particularly impressive in the stroma surrounding malignant crypts (brown—indicated by blue arrow heads). Representative images of normal mucosa and two different human colorectal cancer specimens are shown in FIG. 27A. Similarly, DCAMKL-1 expression was observed in a variety of human colon cancer cell lines (FIG. 27B). HCT116 and SW480 cells were transfected with DCAMKL-1 and scrambled siRNA; then total RNA was isolated and subjected to real-time RT-PCR. A >70% reduction in DCAMKL-1 mRNA expression was noted in DCAMKL-1 siRNA (si-DCAMKL-1) treated cells (FIGS. 27C and D). A reduction in DCAMKL-1 protein was also observed following si-DCAMKL-1 transfection (FIGS. 27C and D). Scrambled siRNA (si-Scr) did not affect the expression of DCAMKL-1 mRNA or protein (FIGS. 27C and D).

siRNA mediated knockdown of DCAMKL-1 leads to tumor growth arrest. Given the increased DCAMKL-1 expression in human colorectal tumors (FIG. 27A) and in Apc$^{Min/+}$ adenomas [May et al., 2008], the inventors wanted to determine its role in tumor progression. Tumor xenografts were generated by injecting HCT116 cells ($6\times10^6$) subcutaneously into the flanks of athymic nude mice. After 15 days, si-DCAMKL-1 and si-Scr were injected into the xenografts. Tumor volumes were measured using calipers at various time points before sacrifice and weights were determined after sacrifice [Sureban et al., 2008; Sureban et al., 2008A]. Administration of si-DCAMKL-1 resulted in a statistically significant reduction (p<0.01) in tumor size compared to the control or the si-Scr treated tumors (FIGS. 28A and B). Thus inhibition of DCAMKL-1 arrested HCT116 tumor xenograft growth. Total RNA isolated from these tumors was subjected to real-time RT-PCR and demonstrated a significant downregulation (55%) (p<0.01) of DCAMKL-1 mRNA expression in the si-DCAMKL-1-treated tumors compared to control and si-Scr treated tumors (FIG. 28C). This downregulation was associated with reduced expression of DCAMKL-1 protein in those tumors by Western blot analyses (FIG. 28D).

Knockdown of DCAMKL-1 induces pri-let-7α miRNA. To determine the role of DCAMKL-1 mediated regulation of pri-let-7α miRNA, control and siRNA treated HCT116 tumor xenografts were analyzed for pri-miRNA expression by real-time RT-PCR. Compared to control and si-Scr treated tumors, there was a >3-fold increase in pri-let-7α miRNA expression in DCAMKL-1 siRNA treated tumors (FIG. 29A). Next, the effects of siRNA-mediated knockdown of DCAMKL-1 on pri-let-7α miRNA expression were analyzed in HCT116 and SW480 cells. Real-time RT-PCR analysis revealed a 4-fold increase in pri-let-7α miRNA, compared to controls (FIGS. 29B and C). These data demonstrate that DCAMKL-1 negatively regulates pri-let-7α miRNA in human colon cancer cells.

DCAMKL-1 negatively regulates let-7α miRNA. As stated earlier, lack of let-7 miRNA is an indicator of "stemness" in epithelial progenitor cells [Ibarra et al., 2007; Yu et al., 2007; Stadler et al., 2008]. To determine whether pri-let-7α miRNA was expressed in stem cells, FACS based sorting was utilized to isolate DCAMKL-1 positive and negative cells, which were analyzed for pri-let-7α miRNA. The antibody used for FACS was directed against the c-terminal extracellular domain of DCAMKL-1 [Sossey-Alaoui et al., 1999; Kim et al., 2003] and conjugated to the Alexa Fluor® 568 fluorochrome. Following FACS, both sorted cell populations were examined by fluorescence microscopy. The positively sorted cells demonstrated the presence of DCAMKL-1 antibody staining, whereas the negatively sorted cells did not (FIGS. 30A and B). Furthermore, DCAMKL-1 positive cells did not express L-type fatty acid binding protein (L-FABP), a marker of enterocyte lineage known to be expressed in differentiated intestinal epithelia [Rizvi et al., 2005; Smith et al., 1996], indicating a less differentiated state (FIGS. 30C and E). In contrast, L-FABP was found to be expressed in DCAMKL-1 negative cells (FIGS. 30D and F), indicating that these cells are more differentiated compared to DCAMKL-1 positive cells.

Total miRNA isolated from DCAMKL-1 positive and DCAMKL-1 negative cells were subjected to pri-let-7α miRNA expression by real-time RT-PCR and normalized using pri-U6 miRNA. A 65% reduction in pri-let-7α miRNA was observed in DCAMKL-1 positive sorted "stem" cells relative to DCAMKL-1 negative cells (FIG. 31A). To confirm sorting specificity, total RNA isolated from the cells was subjected to real-time RT-PCR for DCAMKL-1 mRNA expression (FIG. 31B). These data demonstrate that DCAMKL-1 negatively regulates pri-let-7α miRNA in putative intestinal stem/progenitor cells.

To determine quantitatively the effect of siRNA-mediated knockdown of DCAMKL-1 on let-7α miRNA, a luciferase reporter gene assay was performed. HCT116 and SW480 cells were transfected with a plasmid containing firefly luciferase gene with a complementary let-7α binding site at the 3'UTR (FIG. 26). A dose dependent reduction in luciferase activity was observed following the knockdown of DCAMKL-1 (FIGS. 31C and D). This demonstrates that DCAMKL-1 may be a posttranscriptional regulator of let-7α miRNA downstream targets. However, other alternative mechanisms for DCAMKL-1, such as acting as a transcriptional regulator of let-7α or as a posttranscriptional regulator of let-7α maturation, cannot be ruled out.

Knockdown of DCAMKL-1 inhibits c-Myc. HCT116 tumor xenografts were evaluated for expression of the let-7α miRNA downstream oncogenic target c-Myc, following siRNA-mediated knockdown of DCAMKL-1 as described earlier. A 45% reduction in c-Myc mRNA was observed in si-DCAMKL-1 treated tumors compared to controls (FIG. 32A). An even more striking reduction of c-Myc protein was seen by Western blot and immunohistochemical analyses (FIGS. 32B and C) of siDCAMKL-1 treated tumors. A significant reduction in c-Myc mRNA and protein was also observed in siDCAMKL-1 treated HCT116 (FIGS. 32D and E) and SW480 cells (FIGS. 32D and F). These data suggest that knockdown of DCAMKL-1 results in a reduced expression of c-Myc by a let-7α dependent mechanism.

Discussion of Example 4 miRNAs play important gene-regulatory roles by pairing to the mRNAs of protein-coding genes to direct their post-transcriptional repression [Kumar et al., 2007]. The involvement of miRNAs in human cancer has been recently described [Calin et al., 2006], with several reports indicating that miRNAs might be used as future diagnostic and therapeutic targets [Tricoli et al., 2007]. Furthermore, characteristic miRNA expression signatures in various cancers that can profoundly affect cancer cell behavior have been reported [Calin et al., 2006]. miRNAs have been shown to play an important role in regulating stem cell self-renewal and differentiation by repressing the translation of selected mRNAs in stem cells and differentiating daughter cells. Let-7α is a tumor suppressor miRNA that is blocked posttranscriptionally in ES cells and in several human cancers [Thomson et al., 2006; Calin et al., 2006; Suh et al., 2004]. The regulatory factors that control miRNA expression, maturation and function in adult stem cells and cancers are just beginning to be explored.

This Example demonstrates that the novel putative intestinal stem cell marker DCAMKL-1 is a negative regulator of let-7α miRNA expression/function. Here it is demonstrated that DCAMKL-1 expression is increased in human colorectal cancers compared to normal uninvolved tissues. This is the first demonstration of DCAMKL-1 in human colorectal cancer. In addition to the increased epithelial expression of DCAMKL-1 seen within the colorectal tumors examined, strong staining was also observed in the stroma surrounding malignant crypts. Given the importance of epithelial-mesenchymal cell interactions in cancer [Arias, 2001] and the role of the niche in epithelial stem cell fate [Rizvi et al., 2005], it is speculated that stromal DCAMKL-1 may participate in tumor progression.

Using a tumor xenograft model generated from HCT116 human colorectal cancer cells, near complete tumor growth arrest was demonstrated following siRNA-mediated knockdown of DCAMKL-1. These data strongly implicate a functional role for DCAMKL-1 in the regulation of tumor growth. Given the potential roles of let-7α miRNA in the regulation of gene expression in stem cells and cancer, the tumor xenografts were assayed for pri-let-7α miRNA expression. A significant increase in pri-let-7α miRNA was found in the tumors following siRNA-mediated inhibition of DCAMKL-1. These data confirm that pri-let-7α miRNA is indeed a tumor suppressor miRNA, which is regulated by DCAMKL-1 in colorectal cancer cells.

Cellular transformation and tumorigenesis are driven by activation of oncogenes and/or inactivation of tumor suppressors. Oncogenic c-Myc overexpression is observed in many cancers along with enhanced cell proliferation [Smith et al., 1996]. Furthermore, transcripts encoding both c-Myc and Kras are known to contain target sites for the let-7 miRNA in their 3'UTR [Kumar et al., 2007]. Such findings led us to speculate that DCAMKL-1 may affect c-Myc expression in colon cancer via a let-7α dependent mechanism. Indeed, a 45% reduction in c-Myc mRNA was found, as well as a significant decrease in protein levels in the tumors following the inhibition of DCAMKL-1. These findings were confirmed in vitro in human colorectal cancer cell lines where knockdown of DCAMKL-1 resulted in increased pri-let-7α miRNA, which corresponded with a significant reduction of c-Myc. These data taken together strongly suggests that DCAMKL-1 negatively regulates the tumor suppressor miRNA let-7α resulting in reduced expression of its downstream target oncogene c-Myc.

In order to determine the effects of DCAMKL-1 knockdown on let-7α miRNA-dependent gene silencing of let-7α downstream targets, a luciferase gene reporter assay containing a specific let-7α miRNA binding site at its 3'UTR was performed. A significant dose-dependent reduction in luciferase activity was found following knockdown of DCAMKL-1. This provides an explanation and mechanism where inhibition of DCAMKL-1 results in decreased c-Myc and possibly other let-7α downstream targets.

In this Example, it has been demonstrated that DCAMKL-1, a protein expressed in both normal stem cells and in cancer, likely promotes tumorigenesis through the regulation of pri-let-7α miRNA and c-Myc. The presence of let-7α binding sites in the c-Myc 3'UTR leads us to speculate that DCAMKL-1 is regulating c-Myc posttranscriptionally. However, other alternatives cannot be ruled out, such as direct transcriptional regulation. Nevertheless, the knockdown of DCAMKL-1 resulted in a marked reduction in c-Myc mRNA and protein in vitro and in vivo. Moreover, several other oncogenes contain let-7α binding sites in their 3'UTRs, thus it is quite possible that DCAMKL-1 may have similar effects on other oncogenic targets including Kras.

miRNAs are known to contribute to the preservation of 'stemness' and associated with self-renewal and differentiation in ES cells [Shcherbata et al., 2006]. Previous studies have also shown an overall reduction in miRNA expression in embryonic and tissue stem cells [Croce et al., 2005]. Intestinal epithelial cells were analyzed following FACS based sorting using DCAMKL-1 for pri-let-7α miRNA. A marked reduction in pri-let-7α miRNA was observed in DCAMKL-1 positively sorted "stem" cells relative to DCAMKL-1 negative cells. These data demonstrate that intestinal stem cells, like ES cells, express low levels of let-7α.

The findings presented in this Example demonstrate that regulation of miRNAs represent an exciting new strategy to combat tumorigenesis, particularly in cancers originating from cancer stem cells.

Thus, in accordance with the present invention, there have been provided methods of identifying a gastrointestinal, pancreatic and/or cancer stem cell marker, and methods of use thereof, that fully satisfy the objectives and advantages set forth hereinabove. Although the invention has been described in conjunction with the specific drawings, experimentation, results and language set forth hereinabove, it is evident that many alternatives, modifications, and variations will be apparent to those skilled in the art. Accordingly, it is intended to embrace all such alternatives, modifications and variations that fall within the spirit and broad scope of the invention.

REFERENCES

The following references, to the extent that they provide exemplary procedural or other details supplementary to those set forth herein, are specifically incorporated herein by reference.

Abraham E J, Kodama S, Lin J C, et al. Human pancreatic islet-derived progenitor cell engraftment in immunocompetent mice. Am J Pathol 2004; 164:817-830.

Al-Hajj M, Wicha M S, Benito-Hernandez A, et al. Prospective identification of tumorigenic breast cancer cells. Proc Natl Acad Sci USA 2003; 100:3983-3988.

Arias A M. Epithelial mesenchymal interactions in cancer and development. Cell 2001; 105:425-31.

Bao S, Wu Q, McLendon R E, et al. Glioma stem cells promote radioresistance by preferential activation of the DNA damage response. Nature 2006; 444:756-760.

Bao S, Wu C, Sathornsumetee S, et al. Stem Cell-like Glioma Cells Promote Tumor Angiogenesis through Vascular Endothelial Growth Factor. Cancer Res 2006; 66:7843-7848.

Barker N, van Es J H, Kuipers J, et al. Identification of stem cells in small intestine and colon by marker gene Lgr5. Nature 2007; 449:1003-1007.

Bartel D P. MicroRNAs: genomics, biogenesis, mechanism, and function. Cell 2004; 116:281-97.

Becker L, Huang Q, Mashimo H. Immunostaining of Lgr5, an intestinal stem cell marker, in normal and premalignant human gastrointestinal tissue. Scientific World Journal. 2008; 8:1168-1176.

Bjerknes M, Cheng H. Clonal analysis of mouse intestinal epithelial progenitors. Gastroenterology. 1999; 116:7-14.

Bjerknes M, Cheng H. Gastrointestinal stem cells. II. Intestinal stem cells. Am J Physiol Gastrointest Liver Physiol 2005; 289:G381-387.

Bjerknes M, Cheng H. The stem-cell zone of the small intestinal epithelium. III. Evidence from columnar, enteroendocrine, and mucous cells in the adult mouse. The American journal of anatomy 1981; 160:77-91.

Bjerknes M, Cheng H. The stem-cell zone of the small intestinal epithelium. IV. Effects of resecting 30% of the small intestine. The American journal of anatomy. 1981; 160:93-103.

Bonnet D, Dick J E. Human acute myeloid leukemia is organized as a hierarchy that originates from a primitive hematopoietic cell. Nat Med 1997; 3:730-737.

Bussing I, Slack F J, Grosshans H. let-7 microRNAs in development, stem cells and cancer. Trends Mol Med 2008; 14:400-9.

Calabrese J M, Seila A C, Yeo G W, Sharp P A. RNA sequence analysis defines Dicer's role in mouse embryonic stem cells. Proc Natl Acad Sci USA 2007; 104:18097-102.

Calin G A, Croce C M. MicroRNA signatures in human cancers. Nat Rev Cancer 2006; 6:857-66.

Calin G A. Human microRNA genes are frequently located at fragile sites and genomic regions involved in cancers. Proc. Natl Acad. Sci. USA 2004; 101:2999-3004.

Chendrimada T P, Gregory R I, Kumaraswamy E, Norman J, Cooch N, Nishikura K, Shiekhattar R. TRBP recruits the Dicer complex to Ago2 for microRNA processing and gene silencing. Nature 2005; 436:740-4.

Cheng H, Leblond C P. Origin, differentiation and renewal of the four main epithelial cell types in the mouse small intestine. V. Unitarian Theory of the origin of the four epithelial cell types. The American journal of anatomy. 1974; 141: 537-561.

Cheng H, Leblond C P. Origin, differentiation and renewal of the four main epithelial cell types in the mouse small intestine. I. Columnar cell. The American journal of anatomy. 1974; 141:461-479.

Cheshier S H, Morrison S J, Liao X, et al. In vivo proliferation and cell cycle kinetics of long-term self-renewing hematopoietic stem cells. Proceedings of the National Academy of Sciences of the United States of America. 1999; 96:3120-3125.

Clarke A R. Wnt signalling in the mouse intestine. Oncogene 2006; 25:7512-7521.

Clevers H. Wnt breakers in colon cancer. Cancer Cell 2004; 5:5-6.

Clevers H. Wnt/beta-catenin signaling in development and disease. Cell 2006; 127:469-480.

Cohn S M, Schloemann S, Tessner T, et al. Crypt stem cell survival in the mouse intestinal Cohn S M, Simon T C, Roth K A, et al. Use of transgenic mice to map cis-acting elements in the intestinal fatty acid binding protein gene (Fabpi) that control its cell lineage-specific and regional patterns of expression along the duodenal-colonic and crypt-villus axes of the gut epithelium. The Journal of cell biology. 1992; 119:27-44.

Cohn S M, Schloemann S, Tessner T, et al. Crypt stem cell survival in the mouse intestinal epithelium is regulated by prostaglandins synthesized through cyclooxygenase-1. J Clin Invest 1997; 99:1367-1379.

Corpet D E, Pierre F. How good are rodent models of carcinogenesis in predicting efficacy in humans? A systematic review and meta-analysis of colon chemoprevention in rats, mice and men. Eur J Cancer 2005; 41:1911-1922.

Cotsarelis G, Sun T T, Lavker R M. Label-retaining cells reside in the bulge area of pilosebaceous unit: implications for follicular stem cells, hair cycle, and skin carcinogenesis. Cell. 1990; 61:1329-1337.

Croce C M, Calin G A. miRNAs, cancer, and stem cell division. Cell 2005; 122:6-7.

de Lau W, Barker N, Clevers H. WNT signaling in the normal intestine and colorectal cancer. Front Biosci 2007; 12:471-491.

Crossman M W, Hauft S M, Gordon J I. The mouse ileal lipid-binding protein gene: a model for studying axial patterning during gut morphogenesis. The Journal of cell biology. 1994; 126:1547-1564.

Dekaney C M, Rodriguez J M, Graul M C, et al. Isolation and characterization of a putative intestinal stem cell fraction from mouse jejunum. Gastroenterology. 2005; 129:1567-1580.

Diehn M, Clarke M F. Cancer stem cells and radiotherapy: new insights into tumor radioresistance. J Natl Cancer Inst 2006; 98:1755-1757.

Dontu G, Abdallah W M, Foley J M, et al. In vitro propagation and transcriptional profiling of human mammary stem/progenitor cells. Genes Dev 2003; 17:1253-1270.

Fearon E R, Vogelstein B. A genetic model for colorectal tumorigenesis. Cell. 1990; 61:759-767.

Frye M, Gardner C, Li E R, et al. Evidence that Myc activation depletes the epidermal stem cell compartment by modulating adhesive interactions with the local microenvironment. Development (Cambridge, England). 2003; 130:2793-2808.

Giannakis M, Chen S L, Karam S M, et al. *Helicobacter pylori* evolution during progression from chronic atrophic gastritis to gastric cancer and its impact on gastric stem cells. Proceedings of the National Academy of Sciences of the United States of America. 2008; 105:4358-4363.

Giannakis M, Stappenbeck T S, Mills J C, et al. Molecular properties of adult mouse gastric and intestinal epithelial progenitors in their niches. J Biol Chem 2006; 281:11292-11300.

Gordon J I, Hermiston M L. Differentiation and self-renewal in the mouse gastrointestinal epithelium. Curr Opin Cell Biol. 1994; 6:795-803.

Gregory R I. The Microprocessor complex mediates the genesis of microRNAs. Nature 2004; 432:235-240.

Grossmann J, Walther K, Artinger M, et al. Progress on isolation and short-term ex-vivo culture of highly purified non-apoptotic human intestinal epithelial cells (IEC). European journal of cell biology. 2003; 82:262-270.

Gu G, Dubauskaite J, Melton D A. Direct evidence for the pancreatic lineage: NGN3+ cells are islet progenitors and are distinct from duct progenitors. Development 2002; 129:2447-2457.

Guweidhi A, Kleeff J, Giese N, et al. Enhanced expression of 14-3-3sigma in pancreatic cancer and its role in cell cycle regulation and apoptosis. Carcinogenesis 2004; 25:1575-1585.

Hatfield S D, Shcherbata H R, Fischer K A, Nakahara K, Carthew R W, Ruohola-Baker H. Stem cell division is regulated by the microRNA pathway. Nature 2005; 435:974-8.

Hauft S M, Kim S H, Schmidt G H, et al. Expression of SV-40 T antigen in the small intestinal epithelium of transgenic mice results in proliferative changes in the crypt and reentry of villus-associated enterocytes into the cell cycle but has no apparent effect on cellular differentiation programs and does not cause neoplastic transformation. The Journal of cell biology. 1992; 117:825-839.

Hingorani S R, Tuveson D A. Targeting oncogene dependence and resistance. Cancer Cell 2003; 3:414-417.

Houchen C W, Stenson W F, Cohn S M. Disruption of cyclooxygenase-1 gene results in an impaired response to radiation injury. Am J Physiol Gastrointest Liver Physiol 2000; 279:G858-865.

Hoyer M, Roed H, Traberg Hansen A, et al. Phase II study on stereotactic body radiotherapy of colorectal metastases. Acta Oncol 2006; 45:823-830.

Humphries A, Wright N A. Colonic crypt organization and tumorigenesis. Nature reviews. 2008; 8:415-424.

Ibarra I, Erlich Y, Muthuswamy S K, Sachidanandam R, Hannon G J. A role for microRNAs in maintenance of mouse mammary epithelial progenitor cells. Genes Dev 2007; 21:3238-43.

Ishizuka S, Martin K, Booth C, et al. Poly(ADPribose) polymerase-1 is a survival factor for radiation exposed intestinal epithelial stem cells in vivo. Nucleic Acids Res 2003; 31:6198-6205.

Jackson E L, Willis N, Mercer K, et al. Analysis of lung tumor initiation and progression using conditional expression of oncogenic K-ras. Genes Dev 2001; 15:3243-3248.

Jensen J, Heller R S, Funder-Nielsen T, et al. Independent development of pancreatic alpha- and beta-cells from neurogenin3-expressing precursors: a role for the notch pathway in repression of premature differentiation. Diabetes 2000; 49:163-176.

Johansson K A, Dursun U, Jordan N, et al. Temporal control of neurogenin3 activity in pancreas progenitors reveals competence windows for the generation of different endocrine cell types. Dev Cell 2007; 12:457-465.

Jones P A, Baylin S B. The epigenomics of cancer. Cell 2007; 128:683-92.

Karam S M, Leblond C P. Dynamics of epithelial cells in the corpus of the mouse stomach. I. Identification of proliferative cell types and pinpointing of the stem cell. The Anatomical record 1993; 236:259-279.

Kayahara T, Sawada M, Takaishi S, et al. Candidate markers for stem and early progenitor cells, Musashi-1 and Hes1, are expressed in crypt base columnar cells of mouse small intestine. FEBS Lett 2003; 535:131-135.

Kim M H, Cierpicki T, Derewenda U, et al. The DCX-domain tandems of doublecortin and doublecortin-like kinase. Nat Struct Biol 2003; 10:324-333.

Kumar M S, Lu J, Mercer K L, Golub T R, Jacks T. Impaired microRNA processing enhances cellular transformation and tumorigenesis. Nat Genet. 2007; 39:673-7.

Lagos-Quintana M, Rauhut R, Lendeckel W, Tuschl T. Identification of novel genes coding for small expressed RNAs. Science 2001; 294:853-858.

Lechner A, Leech C A, Abraham E J, et al. Nestin-positive progenitor cells derived from adult human pancreatic islets of Langerhans contain side population (SP) cells defined by expression of the ABCG2 (BCRP1) ATP-binding cassette transporter. Biochem Biophys Res Commun 2002; 293:670-674.

Lee R C, Ambros V. An extensive class of small RNAs in *Caenorhabditis elegans*. Science 2001; 294:862-864.

Li C, Heidt D G, Dalerba P, et al. Identification of pancreatic cancer stem cells. Cancer Res 2007; 67:1030-1037.

Lin P T, Gleeson J G, Corbo J C, et al. DCAMKL1 encodes a protein kinase with homology to doublecortin that regulates microtubule polymerization. J Neurosci 2000; 20:9152-9161.

Logsdon C D, Simeone D M, Binkley C, et al. Molecular profiling of pancreatic adenocarcinoma and chronic pancreatitis identifies multiple genes differentially regulated in pancreatic cancer. Cancer Res 2003; 63:2649-2657.

Marshman E, Booth C, Potten C S. The intestinal epithelial stem cell. Bioessays. 2002; 24:91-98.

Masters S C, Yang H, Datta S R, et al. 14-3-3 inhibits Bad-induced cell death through interaction with serine-136. Mol Pharmacol 2001; 60:1325-1331.

May R, Riehl T E, Hunt C, et al. Identification of a novel putative gastrointestinal stem cell and adenoma stem cell marker, doublecortin and CaM kinase-like-1, following radiation injury and in adenomatous polyposis coli/multiple intestinal neoplasia mice. Stem Cells 2008; 26:630-637.

McClanahan T, Koseoglu S, Smith K, et al. Identification of overexpression of orphan G protein-coupled receptor GPR49 in human colon and ovarian primary tumors. Cancer biology & therapy. 2006; 5:419-426.

McManus M T. MicroRNAs and cancer. Semin Cancer Biol 2003; 13:253-8.

Merritt A J, Potten C S, Kemp C J, et al. The role of p53 in spontaneous and radiation-induced apoptosis in the gastrointestinal tract of normal and p53-deficient mice. Cancer Res 1994; 54:614-617.

Moll R, Divo M, Langbein L. The human keratins: biology and pathology. Histochem Cell Biol 2008; 129:705-733.

Niemeyer G P, Hudson J, Bridgman R, et al. Isolation and characterization of canine hematopoietic progenitor cells. Exp Hematol 2001; 29:686-693.

Obernosterer G, Leuschner P J, Alenius M, Martinez J. Post-transcriptional regulation of microRNA expression. Rna 2006; 12:1161-7.phenotypes. Diabetes 2001; 50:521-533.

Phillips T M, McBride W H, Pajonk F. The response of CD24(-/low)/CD44+ breast cancer-initiating cells to radiation. J Natl Cancer Inst 2006; 98:1777-1785.

Polakis P. Wnt signaling and cancer. Genes Dev 2000; 14:1837-1851.

Pollack P F, Wood J G, Solomon T. Effect of secretin on growth of stomach, small intestine, and pancreas of developing rats. Dig Dis Sci 1990; 35:749-758.

Poste G, Greig R. On the genesis and regulation of cellular heterogeneity in malignant tumors. Invasion Metastasis 1982; 2:137-176.

Potten C S, Booth C, Hargreaves D. The small intestine as a model for evaluating adult tissue stem cell drug targets. Cell Prolif 2003; 36:115-129.

Potten C S, Booth C, Pritchard D M. The intestinal epithelial stem cell: the mucosal governor. Int. J. Exp. Pathol. 1997; 78:219-243.

Potten C S, Booth C, Tudor G L, et al. Identification of a putative intestinal stem cell and early lineage marker; musashi-1. Differentiation 2003; 71:28-41.

Potten C S, Loeffler M. A comprehensive model of the crypts of the small intestine of the mouse provides insight into the mechanisms of cell migration and the proliferation hierarchy. Journal of theoretical biology. 1987; 127:381-391.

Potten C S, Loeffler M. Stem cells: attributes, cycles, spirals, pitfalls and uncertainties. Lessons for and from the crypt. Development (Cambridge, England). 1990; 110:1001-1020.

Potten C S, Merritt A, Hickman J, et al. Characterization of radiation-induced apoptosis in the small intestine and its biological implications. Int J Radiat Biol 1994; 65:71-78.

Potten C S, Owen G, Booth D. Intestinal stem cells protect their genome by selective segregation of template DNA strands. J Cell Sci 2002; 115:2381-2388.

Potten C S, Taylor Y, Hendry J H. The doubling time of regenerating clonogenic cells in the crypts of the irradiated mouse small intestine. International journal of radiation biology. 1988; 54:1041-1051.

Potten C S. A comprehensive study of the radiobiological response of the murine (BDF1) small intestine. Int J Radiat Biol 1990; 58:925-973.

Powell S M, Zilz N, Beazer-Barclay Y, et al. APC mutations occur early during colorectal tumorigenesis. Nature 1992; 359:235-237.

Purkis P E, Steel J B, Mackenzie I C, et al. Antibody markers of basal cells in complex epithelia. Journal of cell science. 1990; 97 (Pt 1):39-50.

Quante M, Wang T C. Inflammation and stem cells in gastrointestinal carcinogenesis. Physiology (Bethesda). 2008; 23:350-359.

Radford I R, Lobachevsky P N. An enteroendocrine cell-based model for a quiescent intestinal stem cell niche. Cell Prolif 2006; 39:403-414.

Radtke F, Clevers H. Self-renewal and cancer of the gut: two sides of a coin. Science 2005; 307:1904-1909.

Reinhart B. The 21 nucleotide let-7 RNA regulates C. elegans developmental timing. Nature 2000; 403:901-906.

Reya T, Morrison S J, Clarke M F, et al. Stem cells, cancer, and cancer stem cells. Nature 2001; 414:105-111.

Riehl T, Cohn S, Tessner T, et al. Lipopolysaccharide is radioprotective in the mouse intestine through a prostaglandin-mediated mechanism. Gastroenterology 2000; 118:1106-1116.

Rizvi A Z, Wong M H. Epithelial stem cells and their niche: there's no place like home. Stem Cells 2005; 23:150-65.

Rubin D C, Swietlicki E, Roth K A, et al. Use of fetal intestinal isografts from normal and transgenic mice to study the programming of positional information along the duodenal-to-colonic axis. The Journal of biological chemistry. 1992; 267:15122-15133.

Samuel S, Walsh R, Webb J, et al. Characterization of putative stem cells in isolated human colonic crypt epithelial cells and their interactions with myofibroblasts. Am J Physiol Cell Physiol. 2009; 296:C296-305.

Sancho E, Batile E, Clevers H. Live and let die in the intestinal epithelium. Curr Opin Cell Biol 2003; 15:763-770.

Sangiorgi E, Capecchi M R. Bmi1 is expressed in vivo in intestinal stem cells. Nat. Genet. 2008; 40:915-920.

Sansom O J, Reed K R, van de Wetering M, et al. Cyclin D1 is not an immediate target of beta-catenin following Apc loss in the intestine. J Biol Chem 2005; 280:28463-28467.

Schmidt G H, Wilkinson M M, Ponder B A. Cell migration pathway in the intestinal epithelium: an in situ marker system using mouse aggregation chimeras. Cell. 1985; 40:425-429.

Schwitzgebel V M, Scheel D W, Conners J R, et al. Expression of neurogenin3 reveals an islet cell precursor population in the pancreas. Development 2000; 127:3533-3542.

Shcherbata H R, Hatfield S, Ward E J, Reynolds S, Fischer K A, Ruohola-Baker H. The MicroRNA pathway plays a regulatory role in stem cell division. Cell Cycle 2006; 5:172-5.

Shroyer N F, Wallis D, Venken K J, et al. Gfi1 functions downstream of Math1 to control intestinal secretory cell subtype allocation and differentiation. Genes & development. 2005; 19:2412-2417.

Singh S K, Clarke I D, Hide T, et al. Cancer stem cells in nervous system tumors. Oncogene 2004; 23:7267-7273.

Singh S K, Clarke I D, Terasaki M, et al. Identification of a cancer stem cell in human brain tumors. Cancer Res 2003; 63:5821-5828.

Singh S K, Hawkins C, Clarke I D, et al. Identification of human brain tumour initiating cells. Nature 2004; 432: 396-401.

Smith D R, Goh H S. Overexpression of the c-myc proto-oncogene in colorectal carcinoma is associated with a reduced mortality that is abrogated by point mutation of the p53 tumor suppressor gene. Clin Cancer Res 1996; 2:1049-53.

Sossey-Alaoui K, Srivastava A K. DCAMKL1, a brain-specific transmembrane protein on 13q12.3 that is similar to doublecortin (DCX). Genomics 1999; 56:121-126.

Stadler B M, Ruohola-Baker H. Small RNAs: keeping stem cells in line. Cell 2008; 132:563-6.

Suh M R, Lee Y, Kim J Y, Kim S K, Moon S H, Lee J Y, Cha K Y, Chung H M, Yoon H S, Moon S Y, Kim V N, Kim K S. Human embryonic stem cells express a unique set of microRNAs. Dev Biol 2004; 270:488-98.

Sureban S M, May R, George R J, Dieckgraefe B K, McLeod H L, Ramalingam S, Bishnupuri K S, Natarajan G, Anant S, Houchen C W. Knockdown of RNA Binding Protein Musashi-1 Leads to Tumor Regression In Vivo. Gastroenterology 2008; 134:1448-1458.e1442.

Sureban S M, Ramalingam S, Natarajan G, May R, Subramaniam D, Bishnupuri K S, Morrison A R, Dieckgraefe B K, Brackett D J, Postier R G, Houchen C W, Anant S. Translation regulatory factor RBM3 is a proto-oncogene that prevents mitotic catastrophe. Oncogene 2008; 27:4544-4556.

Takamizawa J, Konishi H, Yanagisawa K, Tomida S, Osada H, Endoh H, Harano T, Yatabe Y, Nagino M, Nimura Y, Mitsudomi T, Takahashi T. Reduced expression of the let-7 microRNAs in human lung cancers in association with shortened postoperative survival. Cancer Res 2004; 64:3753-3756.

Tamaki S, Eckert K, He D, et al. Engraftment of sorted/expanded human central nervous system stem cells from fetal brain. J Neurosci Res 2002; 69:976-986.

Tang C, Ang B T, Pervaiz S. Cancer stem cell: target for anti-cancer therapy. Faseb J 2007.

Tessner T G, Cohn S M, Schloemann S, et al. Prostaglandins prevent decreased epithelial cell proliferation associated with dextran sodium sulfate injury in mice. Gastroenterology 1998; 115:874-882.

Theodosiou N A, Tabin C J. Wnt signaling during development of the gastrointestinal tract. Dev Biol 2003; 259:258-271.

Thomson J M, Newman M, Parker J S, Morin-Kensicki E M, Wright T, Hammond S M. Extensive post-transcriptional regulation of microRNAs and its implications for cancer. Genes Dev 2006; 20:2202-7.

Tricoli J V, Jacobson J W. MicroRNA: Potential for Cancer Detection, Diagnosis, and Prognosis. Cancer Res 2007; 67:4553-5.

Turley E A, Veiseh M, Radisky D C, et al. Mechanisms of disease: epithelial-mesenchymal transition—does cellular plasticity fuel neoplastic progression? Nat Clin Pract Oncol 2008; 5:280-290.

Vella M C, Choi E Y, Lin S Y, Reinert K, Slack F J. The *C. elegans* microRNA let-7 binds to imperfect let-7 complementary sites from the lin-41 3[prime] UTR. Genes Dev. 2004; 18:132-137.

Viswanathan S R, Daley G Q, Gregory R I. Selective blockade of microRNA processing by Lin28. Science 2008; 320:97-100.

Winton D J, Ponder B A. Stem-cell organization in mouse small intestine. Proc. Biol. Sci. 1990; 241:13-18.

Withers H R, Elkind M M. Microcolony survival assay for cells of mouse intestinal mucosa exposed to radiation. Int J Radiat Biol Relat Stud Phys Chem Med 1970; 17:261-267.

Wright N A. Epithelial stem cell repertoire in the gut: clues to the origin of cell lineages, proliferative units and cancer. Int J Exp Pathol 2000; 81:117-143.

Xu X, D'Hoker J, Stange G, et al. Beta cells can be generated from endogenous progenitors in injured adult mouse pancreas. Cell 2008; 132:197-207.

Yang Q, Bermingham N A, Finegold M J, et al. Requirement of Math1 for secretory cell lineage commitment in the mouse intestine. Science. 2001; 294:2155-2158.

Yu F, Yao H, Zhu P, Zhang X, Pan Q, Gong C, Huang Y, Hu X, Su F, Lieberman J, Song E. let-7 regulates self renewal and tumorigenicity of breast cancer cells. Cell 2007; 131:1109-23.

Zhang J, Niu C, Ye L, et al. Identification of the haematopoietic stem cell niche and control of the niche size. Nature. 2003; 425:836-841.

Zulewski H, Abraham E J, Gerlach M J, et al. Multipotential nestin-positive stem cells isolated from adult pancreatic islets differentiate ex vivo into pancreatic endocrine, exocrine, and hepatic phenotypes. Diabetes 2001; 50:521-533.

What is claimed is:

1. A short-interfering ribonucleic acid (siRNA) molecule effective at silencing doublecortin and $Ca^{2+}$/calmodulin-dependent kinase-like-1 (DCAMKL-1) expression, wherein said siRNA comprises a sense RNA strand and an antisense RNA strand, wherein the sense and antisense RNA strands form an RNA duplex, and wherein the sense RNA strand comprises SEQ ID NO:3.

2. A pharmaceutical composition comprising the siRNA of claim 1.

3. The pharmaceutical composition of claim 2, further comprising at least one additional chemotherapeutic agent.

4. The pharmaceutical composition of claim 2, further comprising a delivery agent.

5. The pharmaceutical composition of claim 4, wherein the delivery agent comprises a liposome.

6. A method of inhibiting expression of DCAMKL-1 protein, comprising the step of:
contacting a cell expressing DCAMKL-1 protein with a short-interfering ribonucleic acid (siRNA) comprising a sense RNA strand and an antisense RNA strand, wherein the sense and antisense RNA strands form an RNA duplex, and wherein the sense RNA strand comprises SEQ ID NO:3, thereby specifically inhibiting the expression of DCAMKL-1.

7. A method of inhibiting expression of DCAMKL-1 protein in a subject, comprising the step of:
administering to a subject an effective amount of pharmaceutical composition comprising a short-interfering ribonucleic acid (siRNA) comprising a sense RNA strand and an antisense RNA strand, wherein the sense and antisense RNA strands form an RNA duplex, and wherein the sense RNA strand comprises SEQ ID NO:3, thereby specifically inhibiting the expression of DCAMKL-1.

8. The method of claim 7, wherein the pharmaceutical composition further comprises a delivery agent.

9. The method of claim 8, wherein the delivery agent comprises a liposome.

10. A method of inhibiting tumor growth, comprising the step of:
contacting the tumor with a short-interfering ribonucleic acid (siRNA) comprising a sense RNA strand and an antisense RNA strand, wherein the sense and antisense RNA strands form an RNA duplex, and wherein the sense RNA strand comprises SEQ ID NO:3, thereby specifically inhibiting the expression of DCAMKL-1 in the tumor and thus inhibiting growth of the tumor.

11. The method of claim 10, wherein the step of contacting the tumor with the siRNA results in at least one of a decrease in cancer cell proliferation, apoptosis, $G_2/M$ arrest, mitotic catastrophe, a decrease in at least one of mRNA stability and mRNA translation for at least one of c-Myc, KRAS, and combinations thereof, and an increase in miRNA expression.

12. A method of inhibiting tumor growth in a subject, comprising the steps of:
administering an effective amount of a pharmaceutical composition to the subject, the pharmaceutical composition comprising a short-interfering ribonucleic acid (siRNA), the siRNA comprising a sense RNA strand and an antisense RNA strand, wherein the sense and antisense RNA strands form an RNA duplex, and wherein the sense RNA strand comprises SEQ ID NO:3, whereby the administration of the effective amount of the pharmaceutical composition specifically inhibits the expression of DCAMKL-1 in the tumor and thus inhibits growth of the tumor.

\* \* \* \* \*